(12) United States Patent
Nishimura et al.

(10) Patent No.: US 12,337,295 B2
(45) Date of Patent: Jun. 24, 2025

(54) WATER-ABSORBING RESIN AND MANUFACTURING METHOD FOR SAME

(71) Applicant: NIPPON SHOKUBAI CO., LTD., Osaka (JP)

(72) Inventors: Kimiaki Nishimura, Himeji (JP); Nobuya Tanaka, Himeji (JP); Tomoya Arai, Himeji (JP); Kazuki Kimura, Himeji (JP); Kazushi Horie, Himeji (JP); Kenji Tada, Himeji (JP)

(73) Assignee: NIPPON SHOKUBAI CO., LTD., Osaka (JP)

( * ) Notice: Subject to any disclaimer, the term of this patent is extended or adjusted under 35 U.S.C. 154(b) by 555 days.

(21) Appl. No.: 17/798,757

(22) PCT Filed: Feb. 12, 2021

(86) PCT No.: PCT/JP2021/005228
§ 371 (c)(1),
(2) Date: Aug. 10, 2022

(87) PCT Pub. No.: WO2021/162085
PCT Pub. Date: Aug. 19, 2021

(65) Prior Publication Data
US 2023/0102961 A1     Mar. 30, 2023

(30) Foreign Application Priority Data

Feb. 14, 2020   (JP) .................................. 2020-023472
Feb. 14, 2020   (JP) .................................. 2020-023473
Aug. 31, 2020   (JP) .................................. 2020-145970

(51) Int. Cl.
*B01J 20/26*       (2006.01)
*A61F 13/53*       (2006.01)
(Continued)

(52) U.S. Cl.
CPC ............. *B01J 20/267* (2013.01); *A61F 13/53* (2013.01); *B01J 20/28059* (2013.01);
(Continued)

(58) Field of Classification Search
CPC .......... A61F 13/53; A61F 2013/530481; B01J 20/267; B01J 20/28004; B01J 20/28011;
(Continued)

(56) References Cited

U.S. PATENT DOCUMENTS

2005/0209411 A1   9/2005   Nestler et al.
2006/0183828 A1   8/2006   Dairoku et al.
(Continued)

FOREIGN PATENT DOCUMENTS

CN   1993176 A     7/2007
CN   101031608 A   9/2007
(Continued)

OTHER PUBLICATIONS

Office Action from Chinese Application No. 202180014372.8 dated Dec. 27, 2024.
(Continued)

*Primary Examiner* — Brian A McCaig
(74) *Attorney, Agent, or Firm* — Harness Dickey & Pierce P.L.C.

(57) ABSTRACT

It is an object to provide a water-absorbing resin that while maintaining water-absorbing resin physical properties such as water absorption performance, has a sufficiently reduced odor produced during swelling. The object is attained by causing the water-absorbing resin to be a water-absorbing resin which is a surface-crosslinked water-absorbing resin, the water-absorbing resin having a volatile component concentration of 3.5 ppm or less as measured when the water-
(Continued)

absorbing resin is caused to stand still for 15 minutes under a condition that the water-absorbing resin has a swelling capacity of 1.0-fold.

19 Claims, 1 Drawing Sheet

(51) Int. Cl.
  *B01J 20/28* (2006.01)
  *B01J 20/32* (2006.01)
  *C08J 3/24* (2006.01)
(52) U.S. Cl.
  CPC .......... *B01J 20/3282* (2013.01); *C08J 3/245* (2013.01); *A61F 2013/530481* (2013.01); *B01J 2220/68* (2013.01); *C08J 2333/02* (2013.01)
(58) Field of Classification Search
  CPC ............ B01J 20/28038; B01J 20/28057; B01J 20/28059; B01J 20/3282; B01J 2220/68; C08F 6/008; C08J 3/075; C08J 3/12; C08J 3/245; Y02P 20/54
  See application file for complete search history.

(56) References Cited

U.S. PATENT DOCUMENTS

| 2008/0075937 | A1 | 3/2008 | Wada et al. |
| 2008/0125533 | A1 | 5/2008 | Riegel et al. |
| 2009/0036855 | A1 | 2/2009 | Wada et al. |
| 2009/0264845 | A1 | 10/2009 | Himori et al. |
| 2009/0275470 | A1 | 11/2009 | Nagasawa et al. |
| 2009/0326162 | A1 | 12/2009 | Hiromu et al. |
| 2010/0035757 | A1 | 2/2010 | Furno et al. |
| 2010/0062252 | A1 | 3/2010 | Kimura et al. |
| 2010/0331802 | A1 | 12/2010 | Yokoyama et al. |
| 2011/0207837 | A1 | 8/2011 | Luckert et al. |
| 2011/0208146 | A1 | 8/2011 | Michnacs et al. |
| 2011/0237739 | A1 | 9/2011 | Tada et al. |
| 2012/0083411 | A1 | 4/2012 | Ahmed et al. |
| 2013/0274088 | A1 | 10/2013 | Handa et al. |
| 2014/0094570 | A1 | 4/2014 | Yokoyama et al. |
| 2014/0107293 | A1 | 4/2014 | Kadonaga et al. |
| 2014/0193641 | A1 | 7/2014 | Torii et al. |
| 2015/0011388 | A1 | 1/2015 | Matsumoto et al. |
| 2019/0194367 | A1 | 6/2019 | Lee et al. |
| 2021/0115198 | A1 | 4/2021 | Yorino et al. |
| 2021/0147637 | A1 | 5/2021 | Matsumoto et al. |

FOREIGN PATENT DOCUMENTS

| JP | 2005-525445 A | 8/2005 |
| JP | 2006-063508 A | 3/2006 |
| JP | 2006-297373 A | 11/2006 |
| JP | 2009-515691 A | 4/2009 |
| JP | 2013-520244 A | 6/2013 |
| WO | WO-2006/033477 A1 | 3/2006 |
| WO | WO-2006/042704 A2 | 4/2006 |
| WO | WO-2009/025235 A1 | 2/2009 |
| WO | WO-2012/108253 A1 | 8/2012 |
| WO | WO-2013/002387 A1 | 1/2013 |
| WO | WO-2013/122246 A1 | 8/2013 |
| WO | 2014162843 A1 | 10/2014 |
| WO | WO-2019/022389 A1 | 1/2019 |
| WO | 2019221235 A1 | 11/2019 |

OTHER PUBLICATIONS

Written Opinion dated May 11, 2021 issued in corresponding international patent application No. PCT/JP2021/005228.
International Search Report dated May 11, 2021 issued in corresponding international patent application No. PCT/JP2021/005228.
Partial Supplementary European Search Report from European Application No. 21752922.1 dated Feb. 5, 2024.
Extended European Search Report for EP Application No. 21752922.1 dated Jun. 7, 2024.

WATER-ABSORBING RESIN AND MANUFACTURING METHOD FOR SAME

PRIORITY STATEMENT

This application is a national stage application under 35 U.S.C. § 371 of PCT International Application No. PCT/JP2021/005228, which has an international filing date of 12 Feb. 2021 and claims priority under 35 U.S.C. § 119 to Japanese Patent Application No. 2020-023472 filed on 14 Feb. 2020, Japanese Patent Application No. 2020-023473 filed on 14 Feb. 2020, and Japanese Patent Application No. 2020-145970 filed on 31 Aug. 2020. The contents of each application recited above are incorporated herein by reference in their entirety.

TECHNICAL FIELD

The present invention relates to a water-absorbing resin that has a reduced odor produced during swelling, and a method for producing the water-absorbing resin.

BACKGROUND ART

A superabsorbent polymer (SAP) is used as a water absorbing agent that is contained in hygienic materials (sanitary products or absorbent articles) such as a disposable diaper, a sanitary napkin, and a so-called incontinence pad. A surface-crosslinked water-absorbing resin is commonly used as the SAP.

It is commonly known that sensitivity to an odor varies depending on, for example, an individual's lifestyle and environment and even a slight odor changes pleasant-unpleasant impression. In recent years, in accordance with consumers' higher awareness of health and safety, a slight odor to which less attention has been conventionally paid has been attracting attention also in the field of hygienic materials (sanitary products or absorbent articles).

It is known that in a conventional hygienic material, an odor is produced during swelling due to slight amounts of various impurities contained in a raw material. It has been gradually understood that there are a certain proportion of users who find such an odor uncomfortable. Examples of an odor produced from such an aforementioned hygienic material that has absorbed urine etc. include not only an odor of the urine etc. but also an odor produced by absorption of and/or contact with moisture contained in the urine etc., and this odor is considered to be produced from chemical products such as nonwoven fabric, an adhesive agent, a glue, and a water-absorbing resin.

A surface-crosslinked water-absorbing resin contains only slight amounts of various impurities such as unreacted products derived from a reactive raw material, including a residual monomer and a residual cross-linking agent, and by-products that are by-produced from a raw material. Thus, a water-absorbing resin-derived odor is produced from a surface-crosslinked water-absorbing resin that gets swollen as the surface-crosslinked water-absorbing resin absorbs moisture (or urine water). This unfortunately gives an impression that is unpleasant to some of the consumers.

There has been conventionally developed a method for reducing an odor that is produced when a surface-crosslinked water-absorbing resin gets swollen.

For example, Patent Literature 1 discloses a method for preventing or reducing production of such an aforementioned odor in a surface-crosslinked water-absorbing resin by controlling a volatile alcohol-based substance content or a residual ethylene glycol content in a specific range.

Patent Literature 2 discloses a method in which sulfite or persulfate is added to a water-absorbing resin and the sulfite or the persulfate is reacted with a residual monomer so that a residual monomer amount in the water-absorbing resin is reduced.

Patent Literature 3 discloses a method in which an aggregation preventing agent and water are added to a surface-crosslinked water-absorbing resin and then the surface-crosslinked water-absorbing resin is dried so that an odor is removed together with the water.

Patent Literature 4 discloses a method in which an odor binder containing an aqueous cysteine-containing solution is added to a surface-crosslinked water-absorbing resin and then the surface-crosslinked water-absorbing resin is dried so that an odor is removed.

Patent Literature 5 discloses a method for removing an odor by using a post-crosslinking agent such as 2-oxazolidone to carry out a post-crosslinking reaction with respect to a water-absorbing resin.

Patent Literatures 6 to 7 each disclose a method for removing a dispersion medium-derived odor by subjecting a water-absorbing resin obtained through reversed phase suspension polymerization to a reduction in dispersion medium inside resin particles.

CITATION LIST

Patent Literatures

[Patent Literature 1]
WO2006/033477 (Japanese Patent Application Publication, Tokukai, No. 2006-116535)
[Patent Literature 2]
Japanese Patent Application Publication, Tokukai, No. 2006-297373
[Patent Literature 3]
WO2019/022389
[Patent Literature 4]
Published Japanese Translation of PCT International Application, Tokuhyo, No. 2009-515691
[Patent Literature 5]
WO2006/042704
[Patent Literature 6]
WO2012/108253
[Patent Literature 7]
WO2009/025235

SUMMARY OF INVENTION

Technical Problem

In recent years, the hygienic materials have been made thinner. Achievement of a thinner hygienic material causes the surface-crosslinked water-absorbing resin to be contained in the hygienic material in a larger amount, but causes a component different from the surface-crosslinked water-absorbing resin, such as pulp to be contained in the hygienic material in a smaller amount. Note here that pulp also has a deodorizing effect to adsorb an odor. Thus, pulp that is contained in a hygienic material in a smaller amount in accordance with achievement of a thinner hygienic material causes an odor derived from the water-absorbing resin to be produced in a larger amount. Furthermore, for example, in a case where a hygienic material is an incontinence pad, achievement of a thinner hygienic material causes pulp that adsorbs an odor to be contained in a smaller amount in the hygienic material. This allows users such as a caregiver and a wearer to more easily perceive the odor.

That is, since in recent years, achievement of a thinner hygienic material has caused the odor to be produced in a larger amount and has allowed the users to more easily perceive the odor, such a conventional technique as described earlier is insufficient to solve an odor-related problem.

Moreover, in recent years, achievement of a thinner hygienic material has made a required water absorption speed higher. A higher water absorption speed is ordinarily achieved by increasing a specific surface area of the surface-crosslinked water-absorbing resin. However, the surface-crosslinked water-absorbing resin that has a greater specific surface area allows such an aforementioned odor substance (a component volatilized from impurities contained in the water-absorbing resin) that is present inside the surface-crosslinked water-absorbing resin to be easily volatilized externally. This causes an odor derived from the surface-crosslinked water-absorbing resin to be produced in a larger amount.

An aspect of the present invention has an object to provide a water-absorbing resin that while maintaining water-absorbing resin physical properties such as water absorption performance, has a sufficiently reduced odor produced during swelling, and a method for producing the water-absorbing resin.

Solution to Problem

As a result of conducting diligent research in order to attain the object, the inventors of the present invention have finally accomplished the present invention by finding that, by causing a surface-crosslinked water-absorbing resin to have a volatile component concentration of a certain value or less during its low-rate swelling, it is possible to provide a water-absorbing resin that while maintaining water-absorbing resin physical properties such as water absorption performance, has a reduced odor produced during swelling, and a method for producing the water-absorbing resin.

That is, an embodiment of the present invention includes the following aspects.

A water-absorbing resin which is a surface-crosslinked water-absorbing resin, the water-absorbing resin having a volatile component concentration of 3.5 ppm or less as measured when the water-absorbing resin is caused to stand still for 15 minutes under a condition that the water-absorbing resin has a swelling capacity of 1.0-fold, where the volatile component concentration as measured when the water-absorbing resin is caused to stand still for 15 minutes under the condition that the water-absorbing resin has a swelling capacity of 1.0-fold is a numerical value obtained by adding together concentrations of all substances that are detected by a photoion detector (PID) of a 10.6 eV lamp and that are included in a volatile component which is present in a closed vessel when 10.0 g of a physiological saline at 23.5±0.5° C. is uniformly added, under room temperature and atmospheric pressure, to 10.0 g of the water-absorbing resin contained in a 2-liter closable glass vessel and the water-absorbing resin to which the physiological saline has been added is caused to stand still in a closed state for 15 minutes, the volatile component concentration being a value represented by a detection value in terms of isobutylene, which is a calibration gas.

A method for producing a water-absorbing resin, including the step of adding a water-based liquid in a droplet state to a surface-crosslinked water-absorbing resin so that the surface-crosslinked water-absorbing resin to which the water-based liquid has been added has a moisture content of 7.5 mass % or more, and then drying the surface-crosslinked water-absorbing resin, to which the water-based liquid has been added, so that the moisture content is reduced by an amount of 7.5 mass % or more within one hour.

A method for producing a water-absorbing resin, including the step of bringing the water-absorbing resin into contact with a supercritical solvent so as to remove a volatile component from the water-absorbing resin,
 the water-absorbing resin containing a polyacrylic acid (salt)-based resin as a main component,
 the water-absorbing resin being internally crosslinked, and
 the water-absorbing resin being surface-crosslinked.

Advantageous Effects of Invention

An aspect of the present invention makes it possible to provide a water-absorbing resin that while maintaining water-absorbing resin physical properties such as water absorption performance, has a reduced odor produced during swelling, and a method for producing the water-absorbing resin.

DESCRIPTION OF EMBODIMENTS

Figure 1:
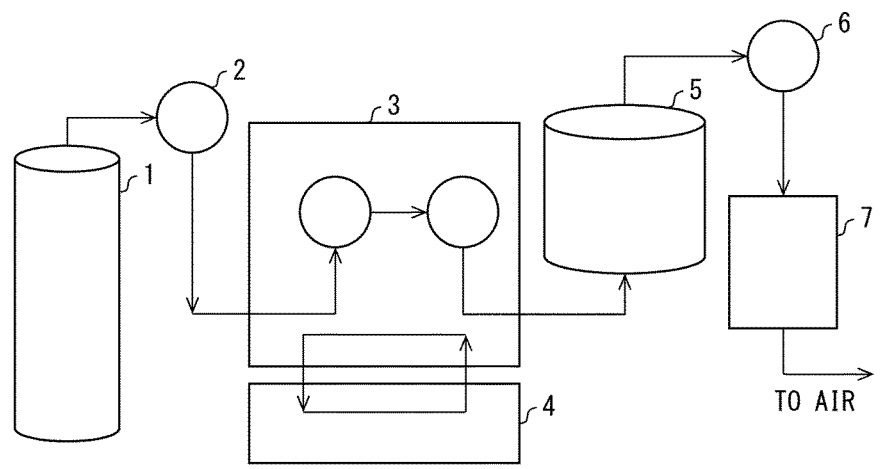
FIG. 1 is a view schematically illustrating an example configuration of a supercritical extraction apparatus that is used in a method for producing a water-absorbing resin according to Embodiment 2 of the present invention.

The following description will specifically discuss embodiments of the present invention. Note, however, that the present invention is not limited to the embodiments below, but can be altered within the disclosure set forth herein. The present invention also encompasses, in its technical scope, embodiments and examples derived from a proper combination of technical means disclosed in different embodiments and examples. Note that as used herein, numerical expressions such as "A to B" mean "not less than A and not more than B", and "ppm" means "mass ppm" or "weight ppm", unless otherwise specified. Note also that "(meth)acrylic" means "acrylic and/or methacrylic", and "mass" and "weight" are regarded as synonyms. Furthermore, a mass of, for example, a water-absorbing resin represents a numerical value on a solid content basis, unless otherwise stated.

[1] Definitions of Terms

[1-1] Water-Absorbing Resin

In the present specification, the term "water-absorbing resin" refers to a crosslinked polymer having a water-swelling property and a water-insolubility, and the water-absorbing resin is generally particulate. Further, the term "water-swelling property" refers to an absorption capacity without load (CRC) as defined in NWSP 241.0.R2 (15) of 5 g/g or more, and the term "water-insolubility" refers to a soluble content (Ext) as defined in NWSP 270.0.R2 (15) of 50 mass % or less.

The "water-absorbing resin" is preferably a hydrophilic crosslinked polymer that has been obtained by crosslinking and polymerizing unsaturated monomers each of which has a carboxyl group. Note, however, that the water-absorbing resin is not necessarily wholly (that is, 100 mass %) the hydrophilic crosslinked polymer, and can contain an additive and/or the like to the extent that the above-described required performance such as CRC and Ext is maintained. The unsaturated monomers each of which has a carboxyl group are preferably acrylic acid (salt)-based monomers.

In the present specification, in some cases, the term "water-absorbing resin" may refer to "a polymer which is crosslinked only internally, that is, a polymer in which an internal crosslinking density and a surface crosslinking density are substantially the same" or "a polymer whose inside and surface are both crosslinked, that is, a polymer in which a surface crosslinking density is higher relative to the internal crosslinking density thereof". In the present specification, the "polymer which is crosslinked only internally" and the "polymer whose inside and surface are both crosslinked" are not distinguished in principle, and are both expressed as "water-absorbing resin". Note, however, that if these polymers need to be clearly distinguished in terms of whether or not they have been surface-crosslinked, the "polymer which is crosslinked only internally", which is a polymer before being surface-crosslinked, is thus expressed as "water-absorbing resin before surface-crosslinking" or "base polymer", and the "polymer whose inside and surface are both crosslinked, that is, a polymer in which a surface crosslinking density is higher relative to the internal crosslinking density thereof", which is a polymer after having been surface-crosslinked, is thus expressed as "water-absorbing resin after surface-crosslinking" or "surface-crosslinked water-absorbing resin". Note that the phrase "before surface-crosslinking" means "before a surface-crosslinking agent is added" or "before a surface-crosslinking reaction caused by a heating treatment starts even after a surface-crosslinking agent has been added".

Further, the term "water-absorbing resin" may refer to only a resin component and may also refer to a resin containing a component other than the resin, such as an additive.

[1-2] "NWSP"

"NWSP" is an acronym for Non-Woven Standard Procedures—Edition 2015, which is methods standardized in Europe and the United States and co-published by European Disposables and Nonwovens Associations (EDANA) and Association of the Nonwoven Fabrics Industry (INDA) for evaluating nonwoven fabrics and products made of nonwoven fabrics. NWSP also indicates standard measurement methods for a water-absorbing resin. In the present specification, physical properties of a water-absorbing resin are measured in conformity with the NWSP master copy (2015).

In the present specification, measurement methods for various physical properties of a water-absorbing resin are carried out in accordance with measurement methods in Examples below, unless otherwise mentioned.

[2] Water-Absorbing Resin

A water-absorbing resin according to an embodiment of the present invention is a surface-crosslinked water-absorbing resin, the water-absorbing resin having a volatile component concentration of 3.5 ppm or less as measured when the water-absorbing resin is caused to stand still for 15 minutes under a condition that the water-absorbing resin has a swelling capacity of 1.0-fold.

While carrying out study in order to attain the object, the inventors of the present invention found that the intensity of an odor that is produced from a water-absorbing resin contained in a hygienic material varies depending on a place of an absorbent body constituting the hygienic material. Specifically, the inventors of the present invention found the following: In a case where a disposable diaper including an absorbent body containing, for example, a water-absorbing resin and a hydrophilic fiber is spread, odorless physiological saline or artificial urine is injected into a central part of the disposable diaper, and an odor emitted after a liquid is diffused and absorbed is smelled, the odor is weak at or near the center, and the odor is strong at a place at which the diffused liquid has arrived. As a result of detailed analysis of the absorbent body, the water-absorbing resin is greatly swollen at or near the center, and the water-absorbing resin at a place at which the diffused liquid has arrived is less swollen than at or near the central part. The inventors of the present invention found, from this result, that a variance in swelling capacity of the water-absorbing resin causes a difference in degree of an odor produced and that the water-absorbing resin which swells at a lower rate produces a stronger odor. The inventors of the present invention considered that the reason for such a difference in degree of the odor may be because odor substances (volatile components) are produced from various impurities contained in the surface-crosslinked water-absorbing resin, and amounts of the odor substances produced differ. A volatile component concentration was measured as a method for measuring the amounts of the odor substances (volatile components) produced. Unexpectedly, it was found that there is a correlation between the volatile component concentration and the degree of the odor (a higher volatile component concentration means a stronger odor). Then, the inventors of the present invention found that the water-absorbing resin that swells at a lower rate causes an increase in concentration of a volatile component produced. The inventors of the present invention also found that the water-absorbing resin which has a swelling capacity as low as 1.0-fold has the highest volatile component concentration and that an odor produced during swelling of the water-absorbing resin in actual use of an absorbent body, in which the water-absorbing resin is used, for a hygienic material can be considerably reduced by causing the volatile component concentration to be a predetermined value or less.

As in, for example, Patent Literatures 1 and 6, an odor produced during swelling of a water-absorbing resin has been conventionally subjected to measurement under a condition that is determined as appropriate, such as 5-fold swelling or 7.5-fold swelling. However, study carried out by the inventors of the present invention has made it clear that unexpectedly, a volatile component produced from the water-absorbing resin has the highest concentration under a swelling condition lower than a conventional measurement condition. Such a low swelling condition is a condition whose correlation with a degree of an odor in actual use of, for example, a hygienic material has not been studied at all. In the present invention, it has been found that in order to reduce an unpleasant odor of a hygienic material, it is the most important to measure, under a low swelling condition in which the unpleasant odor perceived from the hygienic material is highly correlated with a volatile component concentration, a concentration of a volatile component produced from a water-absorbing resin.

In the present invention, the term "swelling capacity" refers to a ratio of a mass of a water-based liquid absorbed by a water-absorbing resin after swelling to a mass of the water-absorbing resin before swelling. For example, the expression "the swelling capacity is 1.0-fold" means that the mass of the water-based liquid absorbed by the water-absorbing resin after swelling is 1.0-fold relative to the mass of the water-absorbing resin before swelling (the absorbed water-based liquid has a mass identical to the mass of the water-absorbing resin before swelling.). Note here that the water-absorbing resin before swelling refers to a water-absorbing resin that has not absorbed water, and also refers to a water-absorbing resin that has a moisture content of preferably 20 mass % or less, more preferably 15 mass % or less, and even more preferably 10 mass % or less, in other words, a water-absorbing resin that has a solid content of 80 mass % or more, more preferably 85 mass % or more, and even more preferably 90 mass % or more.

The expression "a volatile component concentration as measured when the water-absorbing resin is caused to stand still for 15 minutes under a condition that the water-absorbing resin has a swelling capacity of 1.0-fold (in the present specification, may be hereinafter referred to as "a volatile component concentration during 1.0-fold swelling") refers to a concentration of a substance that is detected by a photoionization detector (PID) of a 10.6 eV lamp and that is included in a volatile component (gaseous substance), which is present in a closed vessel when a physiological saline is uniformly added, under room temperature and atmospheric pressure, to the water-absorbing resin contained in a closable glass vessel, so that the water-absorbing resin has a swelling capacity of 1.0-fold, and the water-absorbing resin to which the physiological saline has been added is caused to stand still in a closed state for 15 minutes, and is specifically a value measured by a measurement method disclosed in Examples.

The volatile component concentration as used in the present invention refers to a numerical value obtained by adding together concentrations of all substances that are detected by a photoionization detector (PID) of a 10.6 eV lamp and that are included in a volatile component which is present in the closed vessel, and is a detected numerical value in terms of isobutylene, which is a calibration gas.

Examples of a substance that is detected by the photoionization detector and that is included in the volatile component include acetic acid, methyl acrylate, acrylic acid, methyl acrylate, ethyl acrylate, acetaldehyde, acetone, toluene, ethanol, isopropanol, butanol, ethyl ether, ethyl mercaptan, furfural, heptane, hexane, isobutylene, ammonia, hydrogen sulfide, carbon disulfide, and nitrogen dioxide. Examples of a substance that is not detected by the photoionization detector (PID) include water, oxygen, nitrogen, carbon dioxide, ozone, and hydrogen. In the present specification, the term "volatile component" refers to "a substance that is detected by the photoionization detector (PID) of the 10.6 eV lamp", unless otherwise specified.

In the present specification, a physiological saline is used as an aspect, which may be deionized water (dw) or artificial urine having a specific composition.

The volatile component concentration during 1.0-fold swelling is 3.5 ppm or less, more preferably 3.3 ppm or less, more preferably 3.0 ppm or less, more preferably 2.7 ppm or less, more preferably 2.5 ppm or less, more preferably 2.3 ppm or less, more preferably 1.9 ppm or less, more preferably 1.5 ppm or less, and more preferably 1.0 ppm or less.

In a case where the volatile component concentration during 1.0-fold swelling is 3.5 ppm or less, an odor that is produced during swelling can be considerably reduced in actual use of an absorbent body, in which the water-absorbing resin is used, for a hygienic material.

The water-absorbing resin according to an embodiment of the present invention is preferably configured such that a sum of volatile component concentrations as measured when the water-absorbing resin is caused to stand still for 15 minutes under conditions that the water-absorbing resin has respective swelling capacities of 0.0-fold, 0.5-fold, 1.0-fold, 2.5-fold, 5.0-fold, 10.0-fold, and 20.0-fold is 9.5 ppm or less.

As described earlier, the water-absorbing resin contained in a hygienic material varies in swelling capacity during absorption of urine etc. depending on where in an absorbent body the water-absorbing resin is provided, and volatile components produced at respective swelling capacities have different concentrations. Thus, not only the volatile component concentration at a swelling capacity of 1.0-fold, which is the highest volatile component concentration, but also the volatile component concentrations at the other swelling capacities are also desired to be low. The inventors of the present invention have made it clear that a sum of volatile component concentrations at the seven swelling capacities is preferably controlled to 9.5 ppm or less so that a concentration of a volatile component produced from a hygienic material is controlled at a low level.

Note here that the expression "a sum of volatile component concentrations as measured when the water-absorbing resin is caused to stand still for 15 minutes under conditions that the water-absorbing resin has respective swelling capacities of 0.0-fold, 0.5-fold, 1.0-fold, 2.5-fold, 5.0-fold, 10.0-fold, and 20.0-fold" (in the present specification, hereinafter may be referred to as "a volatile component accumulated value during swelling at respective swelling capacities") refers to a sum of volatile component concentrations at respective swelling capacities when a physiological saline is uniformly added, to the water-absorbing resin contained in a closable glass vessel, so that the water-absorbing resin has respective swelling capacities of 1.0-fold, 0.5-fold, 1.0-fold, 2.5-fold, 5.0-fold, 10.0-fold, and 20.0-fold, and the water-absorbing resin to which the physiological saline has been added is caused to stand still in a closed state for 15 minutes, and is specifically a value measured by a measurement method disclosed in Examples. The volatile component accumulated value during swelling at respective swelling capacities is preferably 9.5 ppm or less, more preferably 8.0 ppm or less, more preferably 7.5 ppm or less, more preferably 7.0 ppm or less, more preferably 6.5 ppm or less, more preferably 6.0 ppm or less, more preferably 5.0 ppm or less, even more preferably 4.0 ppm or less, and even more preferably 3.5 ppm or less.

In a case where the volatile component accumulated value during swelling at respective swelling capacities is 9.5 ppm or less, an odor that is produced during swelling can be considerably reduced during actual use of an absorbent body, in which the water-absorbing resin is used, for a hygienic material.

The water-absorbing resin according to an embodiment of the present invention is preferably configured such that a maximum value of volatile component concentrations measured every five seconds, under a condition that the water-absorbing resin has a swelling capacity of 5.0-fold, until 900 seconds have passed since initiation of swelling of the water-absorbing resin is 0.5 ppm or less.

The inventors of the present invention have also found that an unpleasant odor perceived from a hygienic material is weaker over time, and have also found that a concentration of a volatile component produced during swelling of a water-absorbing resin is correlated with a change over time immediately after swelling. Furthermore, the inventors of the present invention have also found that in order to make it difficult to perceive an unpleasant odor produced from a hygienic material, it is preferable to make it possible to prevent or reduce a maximum concentration in a temporal change in concentration of a volatile component produced from a water-absorbing resin.

Note here that the expression "a maximum value of volatile component concentrations measured every five seconds, under a condition that the water-absorbing resin has a swelling capacity of 5.0-fold, until 900 seconds have passed since initiation of swelling of the water-absorbing resin" (in the present specification, hereinafter may be referred to as "a maximum volatile component concentration during swelling over time") is a maximum value of volatile component concentrations measured every five seconds (180 times in total), in a closed state under a condition that a physiological saline is uniformly added, to the water-absorbing resin contained in a closable vessel, so that the water-absorbing resin has a swelling capacity of 5.0-fold, until 900 seconds have passed since addition of the physiological saline, and is specifically a value measured by a measurement method disclosed in Examples. The maximum volatile component concentration during swelling over time is preferably 0.5 ppm or less, more preferably 0.4 ppm or less, more preferably 0.3 ppm or less, and more preferably 0.2 ppm or less.

In a case where the maximum volatile component concentration during swelling over time is 0.5 ppm or less, an odor that is produced during swelling can be considerably reduced during actual use of an absorbent body, in which the water-absorbing resin is used, for a hygienic material.

The water-absorbing resin according to an embodiment of the present invention is preferably configured such that a sum of volatile component concentrations measured every five seconds, under a condition that the water-absorbing resin has a swelling capacity of 5.0-fold, until 900 seconds have passed since initiation of swelling of the water-absorbing resin is 50.0 ppm or less.

As described earlier, the water-absorbing resin contained in a hygienic material has a lower concentration of a produced volatile component over time. However, the inventors of the present invention have also found that an unpleasant odor perceived from a hygienic material is affected by not only a temporary volatile component concentration but also a total amount of volatile component concentrations from the time of initiation of swelling of the water-absorbing resin, and the total amount is preferably controllable at a low level.

Note here that the expression "a sum of volatile component concentrations measured every five seconds, under a condition that the water-absorbing resin has a swelling capacity of 5.0-fold, until 900 seconds have passed since initiation of swelling of the water-absorbing resin" (in the present specification, hereinafter may be referred to as "a volatile component accumulated value during swelling over time") is a sum of volatile component concentrations measured every five seconds (180 times in total), in a closed state under a condition that a physiological saline is uniformly added, to the water-absorbing resin contained in a closable vessel, so that the water-absorbing resin has a swelling capacity of 5.0-fold, until 900 seconds have passed since addition of the physiological saline, and is specifically a value measured by a measurement method disclosed in Examples. The volatile component accumulated value during swelling over time is preferably 50.0 ppm or less, more preferably 45.0 ppm or less, even more preferably 35.0 ppm or less, still more preferably 25.0 ppm or less, and particularly preferably 20.0 ppm or less.

In a case where the volatile component accumulated value during swelling over time is 50.0 ppm or less, an odor that is produced during swelling can be considerably reduced during actual use of an absorbent body, in which the water-absorbing resin is used, for a hygienic material.

[2-1] Polyacrylic Acid (Salt)-Based Water-Absorbing Resin

The water-absorbing resin according to an embodiment of the present invention is not limited to a polyacrylic acid (salt)-based water-absorbing resin, but preferably contains a polyacrylic acid (salt)-based water-absorbing resin as a main component. In the present specification, the polyacrylic acid (salt)-based water-absorbing resin refers to a hydrophilic crosslinked polymer obtained by crosslinking and polymerizing a monomer composition containing an acrylic acid (salt)-based monomer. In other words, the polyacrylic acid (salt)-based water-absorbing resin is a polymer that has a structural unit derived from acrylic acid (salt) and that has a graft component as an optional component.

In the present specification, the term "acrylic acid (salt)" means acrylic acid and/or a salt thereof, and the term "a monomer composition containing an acrylic acid (salt)-based monomer" means a monomer composition that contains acrylic acid (salt) in an amount of 50 mol % or more, relative to a total amount of monomer(s) excluding a crosslinking agent.

In other words, the polyacrylic acid (salt)-based water-absorbing resin is a crosslinked polymer that contains a structural unit derived from acrylic acid (salt) in an amount of 50 mol % or more, relative to a total amount of structural unit(s) constituting the polyacrylic acid (salt)-based water-absorbing resin, and is a crosslinked polymer that has a graft component as an optional component.

More preferably, the polyacrylic acid (salt)-based water-absorbing resin is a crosslinked polymer obtained by using, for a part, excluding an internal crosslinking agent, of monomer components involved in a polymerization reaction, preferably 50 mol % or more, more preferably 70 mol % or more, even more preferably 90 mol % or more, preferably 100 mol % or less, and particularly preferably substantially 100 mol % of acrylic acid (salt) as a raw material.

(Monomer)

A monomer is a raw material component (monomer) forming a water-absorbing resin (polymer) and includes an acrylic acid (salt)-based monomer, a monomer different from the acrylic acid (salt)-based monomer, and an internal crosslinking agent. A total amount of monomers forming a water-absorbing resin is a monomer composition. Examples of the acrylic acid (salt)-based monomer include (meth)acrylic acid and a salt thereof.

A monomer that may be contained in a monomer composition and that is different from the acrylic acid (salt)-based monomer is preferably an acid group-containing monomer among unsaturated double bond-containing monomers (ethylenically unsaturated monomers). Specific examples of the monomer include: anionic unsaturated monomers and/or salts thereof such as (anhydrous) maleic acid, fumaric acid, crotonic acid, itaconic acid, cinnamic acid, vinyl sulfonic acid, allyltoluene sulfonic acid, vinyltoluene sulfonic acid, styrene sulfonic acid, 2-(meth)acrylamide-2-methylpropane sulfonic acid, 2-(meth)acryloyl ethane sulfonic acid, 2-(meth)acryloyl propane sulfonic acid, and 2-hydroxyethyl(meth)acryloyl phosphate. One kind of monomer or two or more kinds of these monomers is/are used as appropriate.

Examples of the salts include an alkaline metal salt, an ammonium salt, and an amine salt. A sodium salt, a potassium salt, a lithium salt, and an ammonium salt are more preferable, and a sodium salt is particularly preferable.

The monomer composition containing an acrylic acid (salt)-based monomer is preferably neutralized in a range of 10 mol % to 90 mol %, more preferably neutralized in a range of 40 mol % to 80 mol %, and particularly preferably neutralized in a range of 60 mol % to 75 mol %.

Thus, the monomer composition containing an acrylic acid (salt)-based monomer is preferably neutralized with a neutralization solution containing a monovalent basic compound such as a hydroxide of alkali metal, such as sodium hydroxide, potassium hydroxide, or lithium hydroxide, a (hydrogen) carbonate such as sodium (hydrogen) carbonate or potassium (hydrogen) carbonate, or ammonia, and is particularly preferably neutralized with a neutralization solution containing sodium hydroxide.

The monomer composition may contain, as appropriate, a hydrophilic or hydrophobic unsaturated monomer(s) (hereinafter referred to as "other monomer(s)") other than the monomer(s) listed earlier. Examples of the other monomer(s) include mercaptan group-containing unsaturated monomers; phenolic hydroxyl group-containing unsaturated monomers; amide group-containing unsaturated monomers such as N-vinyl-2-pyrrolidone, N-vinylacetamide, (meth) acrylamide, N-isopropyl(meth)acrylamide, N-ethyl(meth) acrylamide, and N,N-dimethyl(meth)acrylamide; and amino group-containing unsaturated monomers such as N,N-dimethylaminoethyl(meth)acrylate, N,N-dimethylaminopropyl (meth)acrylate, and N,N-dimethylaminopropyl(meth)acrylamide. The other monomer(s) may be used in an amount in a degree that does not impair physical properties of a resultant water-absorbing resin. Specifically, the other monomer(s) may be used in an amount of 50 mol % or less, and more preferably 20 mol %, relative to a part, excluding an internal crosslinking agent, of the monomer composition.

(Internal Crosslinking Agent)

Examples of the internal crosslinking agent include N,N'-methylenebis(meth)acrylamide, (poly)ethylene glycol di(meth)acrylate, (poly)propylene glycol di(meth)acrylate, trimethylolpropane di(meth)acrylate, trimethylolpropane tri (meth)acrylate, glycerin tri(meth)acrylate, glycerin acrylate methacrylate, ethyleneoxide modified trimethylol propane tri(meth)acrylate, pentaerythritol tetra(meth)acrylate, dipentaerythritol hexa(meth)acrylate, triallyl cyanurate, triallyl isocyanurate, triallyl phosphate, triallylamine, poly(meth) allyloxy alkane, (poly)ethylene glycol diglycidyl ether, glycerol diglycidyl ether, ethylene glycol, polyethylene glycol, propylene glycol, glycerin, pentaerythritol, ethylenediamine, polyethyleneimine, and glycidyl (meth)acrylate. At least one internal crosslinking agent is selected from among these internal crosslinking agents, with consideration given to reactivity and the like.

In an embodiment of the present invention, from the viewpoint of water absorption performance and the like of the water-absorbing resin, the internal crosslinking agent is preferably an internal crosslinking agent having two or more polymerizable unsaturated groups, and more preferably an internal crosslinking agent having a (poly)alkylene glycol structure and two or more polymerizable unsaturated groups. Specific examples of the polymerizable unsaturated groups include an allyl group and a (meth)acrylate group.

Out of these examples, a (meth)acrylate group is preferable. Further, the internal crosslinking agent having a (poly) alkylene glycol structure and two or more polymerizable unsaturated groups includes polyethyleneglycol di(meth) acrylate. Note that the number (hereinafter expressed as "n") of alkylene glycol units is preferably 1 or more, more preferably 2 or more, even more preferably 4 or more, particularly preferably 6 or more, preferably 100 or less, more preferably 50 or less, even more preferably 20 or less, and particularly preferably 10 or less.

The amount of the internal crosslinking agent used is preferably 0.0001 mol % or more, more preferably 0.001 mol % or more, even more preferably 0.01 mol % or more, preferably 10 mol % or less, more preferably 5 mol % or less, and even more preferably 1 mol % or less, relative to the monomer composition excluding the internal crosslinking agent. Setting the amount of the internal crosslinking agent used to be within the above ranges makes it possible to obtain a water-absorbing resin having a desired water absorption performance. The amount of the internal crosslinking agent used falling outside the above ranges may cause a reduction in gel strength accompanied by an increase in water-soluble component and a reduction in absorption capacity.

(Trace Component)

In the present invention, the monomer composition may contain trace components such as a polymerization inhibitor, Fe, propionic acid, acetic acid, an acrylic acid dimer, and other impurities.

Examples of the polymerization inhibitor that may be contained in the monomer composition include an N-oxyxyl compound, a manganese compound, and a substituted phenolic compound that are shown as examples in International Publication No. WO 2008/096713. The polymerization inhibitor that may be contained in the monomer composition is preferably a substituted phenol, particularly a methoxyphenol (p-methoxyphenol). The polymerization inhibitor is contained in an amount of 5 ppm to 200 ppm, preferably 5 ppm to 160 ppm, more preferably 10 ppm to 160 ppm, even more preferably 10 ppm to 100 ppm, still more preferably 10 ppm to 80 ppm, and most preferably 10 ppm to 70 ppm, relative to the monomer composition.

An amount of iron (Fe) that may be contained in the monomer composition is preferably 2 ppm or less, more preferably 1.5 ppm or less, even more preferably 1.0 ppm or less, still more preferably 0.5 ppm or less, and particularly preferably 0.3 ppm or less, relative to the monomer composition. Note that a lower limit of the amount of Fe is 0.001 ppm or more, and preferably 0.01 ppm from the viewpoint of cost of purification of a base (particularly caustic soda).

Note that an iron content in the monomer composition can be quantitatively determined by, for example, ICP atomic emission spectroscopy described in JIS K1200-6. As a reference for a specific quantitative determination method, International Publication No. WO 2008/090961 can be referred to.

An amount of propionic acid that may be contained in the monomer composition is preferably 500 ppm or less, more preferably 400 ppm, and even more preferably 300 pm or less, relative to the monomer composition.

An amount of acetic acid that may be contained in the monomer composition is suitably 1 mass % or less, preferably 5000 ppm or less, and more preferably 3000 pm or less, relative to the monomer composition. The amount of acetic acid that may be contained in the monomer composition is even more preferably 2000 ppm or less, still more preferably 1000 ppm or less, and particularly preferably 500 ppm or less.

An amount of acrylic acid dimer that may be contained in the monomer composition is suitably 1000 ppm or less, preferably 500 ppm or less, more preferably 200 pm or less, and particularly preferably 100 ppm or less, relative to the monomer composition.

Examples of the other impurities that may be contained in the monomer composition include protoanemonin, allyl acrylate, allyl alcohol, an aldehyde component (particularly furfural), maleic acid, and benzoic acid. Regarding amounts of these six kinds of the other impurities contained in the monomer composition, preferably at least one kind of the other impurities is contained in an amount of 0 ppm to 20 ppm, and more preferably two or more kinds, even more preferably three or more kinds, still more preferably four or more kinds, particularly preferably five or more kinds, and most preferably all six kinds of the other impurities are each contained in an amount of 0 ppm to 20 ppm. An amount of each of the other impurities contained is preferably 0 ppm to 10 ppm, more preferably 0 ppm to 5 ppm, even more preferably 0 ppm to 3 ppm, particularly preferably 0 ppm to 1 ppm, and most preferably ND (detection limit). That is, the amount of all six kinds of the other impurities contained in the monomer composition is most preferably ND (detection limit). Furthermore, a total amount of the other impurities (a sum of weights of six kinds of the other impurities relative to the monomer composition) is preferably 100 ppm or less, more preferably 0 ppm to 20 ppm, and even more preferably 0 ppm to 10 ppm.

The trace components (and derivatives thereof) may be modified into a volatile component (odor) in, for example, a surface-crosslinking step (described later). It is therefore preferable to reduce the presence of these trace amounts from a raw material surface of the monomer composition. In other words, a reduction in amount of the trace components contained in the monomer composition makes it less likely for these trace components to be modified into a volatile component in, for example, the surface-crosslinking step (that is, reduces an odor derived from a volatile component). This makes it possible to reduce an odor from a surface-crosslinked water-absorbing resin.

(Surface-Crosslinking Agent)

The water-absorbing resin according to an embodiment of the present invention is surface-crosslinked. Examples of a surface-crosslinking agent used include the surface-crosslinking agents disclosed in U.S. Pat. No. 7,183,456. At least one surface-crosslinking agent is selected from among these surface-crosslinking agents, with consideration given to reactivity and the like. Furthermore, from the viewpoints of, for example, handleability of the surface-crosslinking agent and water absorption performance of the water-absorbing resin, preferably selected is a surface-crosslinking agent which: has two or more functional groups which react with a carboxyl group; and is an organic compound which forms covalent bonds.

Specific examples of the surface-crosslinking agent include: polyhydric alcohol compounds such as ethylene glycol, diethylene glycol, triethylene glycol, tetraethylene glycol, polyethylene glycol, propylene glycol, dipropylene glycol, polypropylene glycol, 1,3-propanediol, 1,2-butanediol, 1,3-butanediol, 1,4-butanediol, 2,3-butanediol, 1,2-pentanediol, 1,3-pentanediol, 1,4-pentanediol, 1,5-pentanediol, 2,3-pentanediol, 2,4-pentanediol, 1,2-hexanediol, 1,3-hexanediol, 1,4-hexanediol, 1,5-hexanediol, 1,6-hexanediol, 2,3-hexanediol, 2,4-hexanediol, glycerin, polyglycerin, diethanolamine, and triethanolamine; polyhydric amine compounds such as ethylenediamine, diethylenetriamine, triethylenetetramine, tetraethylenepentamine, pentaethylenehexamine, polyallylamine, and polyethylene imine; haloepoxy compounds; a condensate of any of the polyhydric amine compounds and any of the haloepoxy compounds; oxazoline compounds such as 1,2-ethylene bisoxazoline; oxazolidinone compounds; alkylene carbonate compounds such as 1,3-dioxolane-2-one (ethylene carbonate), 4-methyl-1,3-dioxolane-2-one, 4,5-dimethyl-1,3-dioxolane-2-one, 4,4-dimethyl-1,3-dioxolane-2-one, 4-ethyl-1,3-dioxolane-2-one, 4-hydroxymethyl-1,3-dioxolane-2-one, 1,3-dioxane-2-one, 4-methyl-1,3-dioxane-2-one, 4,6-dimethyl-1,3-dioxane-2-one, and 1,3-dioxopane-2-one; polyvalent glycidyl compounds such as ethylene glycol diglycidyl ether, polyethylene diglycidyl ether, propylene glycol diglycidyl ether, polypropylene glycol diglycidyl ether, glycerol polyglycidyl ether, diglycerol polyglycidyl ether, polyglycerol polyglycidyl ether, and glycidol; oxetane compounds; vinyl ether compounds; and cyclic urea compounds. These surface-crosslinking agents may be used alone or in combination of two or more.

[2-2] Volatile Component Reducing Agent

The water-absorbing resin according to an embodiment of the present invention may contain a volatile component reducing agent. The volatile component reducing agent is a substance that has a function to prevent a volatile component (at least one kind among volatile components detected by the photoionization detector), and is, for example, a substance that has a function to capture a volatile component and prevent volatilization of the volatile component. Examples of a mechanism for capturing a volatile component and preventing or reducing volatilization of the volatile component include chemical adsorption or physical adsorption of a volatile component. The volatile component reducing agent may contain at least one selected from a reducing agent, a surfactant, and an inorganic acid (salt).

(Reducing Agent)

The reducing agent is exemplified by, but not particularly limited to, a carboxyl group-containing reducing agent, an amino group-containing reducing agent, a phosphoric acid-based reducing agent, and a sulfuric acid-based reducing agent. Example compounds of the carboxyl group-containing reducing agent include L-ascorbic acid, thioglycolic acid, and mercaptopropionic acid. Example compounds of the amino group-containing reducing agent include hydrazide group-containing compounds such as dihydrazide sebacate, dihydrazide adipate, dihydrazide succinate, and dihydrazide malonate; amino acids such as L-cysteine and cysteamine; and compounds each containing a functional group represented by the following structural formula (1), such as aminooxy compounds such as hydroxylamine and hydroxylamine-O-sulfonic acid, aminooxyacetic acids, and analogous compounds thereof. The amino acids, the aminooxy compounds, the aminooxyacetic acids, and the compounds each containing a functional group represented by the following structural formula (1) may be in a state of hydrochloride (hemihydrochloride) so as to be stabilized.

   Formula (1)

A compound containing a functional group represented by the structural formula (1) is not particularly limited provided that the compound contains a functional group represented by Formula (1). Examples of the compound include compounds having structures represented by the following chemical formulae (2) to (6):

$$H_2N-O-R \qquad \text{Formula (2)}$$

where R is H, $CH_3$, $C_2H_5$, $C_6H_5CH_2$, or $SO_3H$.

$$H_2N-O-\underset{\underset{R}{|}}{CH}-Coor \qquad \text{Formula (3)}$$

where R is H, $CH_3$, n-$C_3H_7$, iso-$C_3H_7$, n-$C_4H_9$, n-$C_6H_{13}$, n-$C_{10}H_{21}$, or $C_6H_5CH_2$, and R may be identical to or different from each other.

$$H_2N-O-CH_2-CH_2-COOH \qquad \text{Formula (4)}$$

$$H_2N-O-CH_2-CH_2-\underset{\underset{NH_2}{|}}{CH}-COOH \qquad \text{Formula (5)}$$

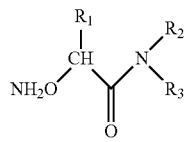

Formula (6)

where $R_1$, $R_2$, and $R_3$ are each H, $C_2H_5$, $C_6H_3C_{12}$, $CH_3$, or $C_2H_5$, and $R_1$, $R_2$, and $R_3$ may be identical to or different from each other.

Example compounds of the phosphoric acid-based reducing agent include hypophosphorous acid, sodium hypophosphite, phosphorous acid, and sodium phosphite. Examples of the sulfuric acid-based reducing agent include sodium sulfite and sodium hydrogen sulfite. Out of the reducing agents, the amino group-containing reducing agent is more preferable, and hydrazide group-containing compounds such as dihydrazide sebacate, dihydrazide adipate, dihydrazide succinate, and dihydrazide malonate; and L-cysteine, cysteamine, and aminooxyacetic acid (hemihydrochloride) are particularly preferable. One or two or more of the reducing agents is/are used as appropriate. In a case where a reducing agent contains a compound that reacts with a hydrazide group (resin or compound containing an active carbonyl group, such as a ketone group and/or an aldehyde group), the hydrazide group reacts and disappears. Due to a deterioration in function to prevent or reduce volatilization of an odor substance (volatile component), it is preferable not to use, in combination, the hydrazide group-containing compound and the compound that reacts with a hydrazide group.

In a case where the water-absorbing resin according to an embodiment of the present invention contains a reducing agent, the reducing agent is contained in an amount of preferably 0.001 mass % to 2.0 mass %, more preferably 0.005 mass % to 1.5 mass %, even more preferably 0.008 mass % to 1.2 mass %, and particularly preferably 0.01 mass % to 1.0 mass %, relative to a total amount of the water-absorbing resin containing, for example, an additive. The reducing agent that is contained in an amount of 0.001 mass % or more makes it possible to suitably remove an odor substance (volatile component). The reducing agent that is contained in an amount of 2.0 mass % or less makes it possible to suitably maintain physical properties of a resultant water-absorbing resin, such as water absorption performance (including whiteness, AAP, etc.). Embodiment 1 makes it possible to not only prevent or reduce an odor derived from a water-absorbing resin but also maintain whiteness. It is also possible to maintain water absorption physical properties (AAP).

(Surfactant)

Examples of the surfactant include anionic surfactants, nonionic surfactants, cationic surfactants, and amphoteric surfactants.

Examples of the anionic surfactants include fatty acid salts such as mixed fatty acid sodium soap, tack dry beef tallow fatty acid sodium soap, stearic acid sodium soap, oleic acid potassium soap, and castor oil potassium soap; alkyl sulfate ester salts such as sodium lauryl sulfate, higher alcohol sodium sulfate, sodium lauryl sulfate, and triethanolamine lauryl sulfate; alkyl benzene sulfonates such as sodium dodecylbenzenesulfonate; alkyl naphthalene sulfonates such as sodium alkylnaphthalenesulfonate; alkyl sulfosuccinates such as sodium dialkylsulfosuccinate and disodium polyoxyethylene dialkylsulfosuccinate; alkyl diphenyl ether disulfonates such as sodium alkyl diphenyl ether disulfonate; alkyl phosphates such as potassium alkyl phosphate; polyoxyethylene alkyl (or alkyl allyl) sulfates such as sodium polyoxyethylene lauryl ether sulfate, sodium polyoxyethylene alkyl ether sulfate, polyoxyethylene alkyl ether triethanolamine sulfate, and sodium polyoxyethylene alkyl phenyl ether sulfate; a special reaction type anionic surfactant; a special carboxylic acid type surfactant: naphthalene sulfonic acid formalin condensates such as a sodium salt of a β-naphthalenesulfonic acid formalin condensate and a sodium salt of a special aromatic sulfonic acid formalin condensate; a special polycarboxylic acid type polymer surfactant; and polyoxyethylene alkyl phosphate ester.

Example nonionic surfactants include polyoxyethylene alkyl ethers such as polyoxyethylene lauryl ether, polyoxyethylene cetyl ether, polyoxyethylene stearyl ether, polyoxyethylene oleyl ether, and polyoxyethylene higher alcohol ether; polyoxyethylene alkylaryl ethers such as polyoxyethylene nonyl phenyl ether; polyoxyethylene derivatives; sorbitan fatty acid esters such as sorbitan monolaurate, sorbitan monopalmitate, sorbitan monostearate, sorbitan tristearate, sorbitan monooleate, sorbitan trioleate, sorbitan sesquioleate, and sorbitan distearate; polyoxyethylene sorbitan fatty acid esters such as polyoxyethylene sorbitan monolaurate, polyoxyethylene sorbitan monolaurate, polyoxyethylene sorbitan monopalmitate, polyoxyethylene sorbitan monostearate, polyoxyethylene sorbitan tristearate, polyoxyethylene sorbitan monooleate, and polyoxyethylene sorbitan trioleate; polyoxyethylene sorbitol fatty acid ester such as polyoxyethylene sorbitol tetraoleate; glycerin fatty acid esters such as glycerol monostearate, glycerol monooleate, and self-emulsifying glycerol monostearate; polyoxyethylene fatty acid esters such as polyethylene glycol monolaurate, polyethylene glycol monostearate, polyethylene glycol distearate, and polyethylene glycol monooleate; polyoxyethylene alkylamine; polyoxyethylene hydrogenated castor oil; and alkyl alkanol amide.

Examples of the cationic surfactants and the amphoteric surfactants include alkyl amine salts such as coconut amine acetate and stearylamine acetate; quaternary ammonium salts such as lauryl trimethyl ammonium chloride, stearyl trimethyl ammonium chlorite, cetyl trimethyl ammonium chloride, distearyl dimethyl ammonium chloride, and alkyl benzyl dimethyl ammonium chloride; alkyl betaines such as lauryl betaine, stearyl betaine, and lauryl carboxymethyl hydroxyethyl imidazolinium betaine; and amine oxides such as lauryl dimethyl amine oxide.

The surfactant is further exemplified by a fluorine atom-containing surfactant. The fluorine atom-containing surfactant usable in an embodiment of the present invention is exemplified by various substances and is, for example, a substance that contains an alkyl group (perfluoroalkyl group) obtained by replacing hydrogen atoms of a hydrophobic group of a common surfactant with fluorine atoms and that has much higher surface activity. Alternatively, the fluorine atom-containing surfactant may be a surfactant that contains, instead of the perfluoroalkyl group, an alkyl group obtained by replacing some (e.g., one hydrogen atom) of the hydrogen atoms of the hydrophobic group with a fluorine atom(s). The fluorine atom-containing surfactant may alternatively be a composition containing a hydrocarbon-based surfactant and a fluorine atom-containing surfactant. For a fluorine atom-containing surfactant, even in a case where a fluorocarbon chain of the same structure is used as a hydrophobic group, changing a hydrophilic group can change the fluorine atom-containing surfactant into any of the following four surfactants: an anionic surfactant, a nonionic surfactant, a cationic surfactant, and an amphoteric surfactant. A carbon chain serving as a hydrophobic group may be a linear chain or be branched for use. Typical examples of the fluorine atom-containing surfactant include the following.

Fluoroalkyl (C2-C10) carboxylic acid, disodium N-perfluorooctanesulfonylglutamate, sodium 3-[fluoroalkyl (C6-C11) oxy]-1-alkyl (C3-C4) sulfonate, sodium 3-[co-fluoroalkanoyl (C6-C8)-N-ethylamino]-1-propanesulfonate, N-[3-(perfluorooctanesulfonamido) propyl]-N, N-dimethyl-N-carboxymethyleneammonium betaine, fluoroalkyl (C11-C20) carboxylic acid, perfluoroalkyl carboxylic acid (C7-C13), perfluorooctanesulfonic acid diethanolamide, perfluoroalkyl (C4-C12) sulfonate (Li, K, Na), N-propyl-N-(2-hydroxyethyl)perfluorooctanesulfonamide, perfluoroalkyl (C6-C10) alphonamidopropyl trimethyl ammonium salt, perfluoroalkyl (C6-C10)-N-ethylsulfonylglycine salt (K), bis(N-perfluorooctylsulfonyl-N-ethylaminoethyl) phosphate, monoperfluoroalkyl (C6-C16) ethyl phosphate, perfluoroalkyl quaternary ammonium iodide (trade name: Fluorad FC-135, cationic fluorine-based surfactant available from Sumitomo 3M Ltd.), perfluoroalkyl alkoxylate (trade name: Fluorad FC-171, nonionic surfactant available from Sumitomo 3M Ltd.), and a potassium salt of perfluoroalkylsulfonic acid (trade name: Fluorad FC-95 and FC-98, anionic surfactant available from Sumitomo 3M Ltd.). The number following each "C" refers to the number of carbon atoms. The expression "C2 to C10", for example, is intended to mean "having 2 to 10 carbon atoms".

An embodiment of the present invention can use an organometallic surfactant as well. An organometallic surfactant usable in an embodiment of the present invention is in the form of molecules each including a metal such as Si, Ti, Sn, Zr, or Ge in a main chain or side chain. The organometallic surfactant preferably is in the form of molecules each including Si in a main chain. The organometallic surfactant is more preferably a siloxane-based surfactant.

Typical examples of the organometallic surfactant include organometallic surfactants mentioned at page 34 of Yoshida, Kondo, Ogaki, and Yamanaka's "Shinpan: Kaimenkasseizai handobukku" (New edition: Surfactant Handbook) published by Kogaku Tosho in 1966. The organometallic surfactant may include a metal of, for example, Sn, Zr, or Ge instead of Si or Ti. The surfactant usable in an embodiment of the present invention is not limited to any of the above surfactants.

The surfactant is, among the above surfactants, preferably a nonionic surfactant, more preferably polyoxyethylene alkyl ether, polyoxyethylene alkylaryl ether, a polyoxyethylene derivative, sorbitan fatty acid ester, polyoxyethylene sorbitan fatty acid ester, or glycerin fatty acid ester among other nonionic surfactants, and particularly preferably sorbitan fatty acid ester or polyoxyethylene sorbitan fatty acid ester, in terms of safety.

In a case where the water-absorbing resin according to an embodiment of the present invention contains a surfactant, the surfactant is contained in an amount of preferably 0.001 mass % to 2.0 mass %, more preferably 0.005 mass % to 1.5 mass %, even more preferably 0.008 mass % to 1.2 mass %, and particularly preferably 0.01 mass % to 1.0 mass %, relative to a total amount of the water-absorbing resin containing, for example, an additive. The surfactant that is contained in an amount of 0.005% mass % or more makes it possible to suitably remove an odor substance (volatile component). The surfactant that is contained in an amount of 1.5 mass % or less makes it possible to suitably maintain physical properties of a resultant water-absorbing resin, such as water absorption performance (including whiteness, AAP, etc.).

(Inorganic Acid (Salt))

The inorganic acid (salt)) is a compound containing an inorganic acid and a salt thereof and is exemplified by carbonate, phosphate, and sulfate. Examples of the inorganic acid (salt)) exclude an inorganic acid (salt) acting as a reducing agent. Example compounds of the carbonate include sodium carbonate, sodium hydrogen carbonate, and sodium sesquicarbonate. Example compounds of the phosphate include disodium hydrogenphosphate, sodium dihydrogenphosphate, and trisodium phosphate.

In a case where the water-absorbing resin according to an embodiment of the present invention contains an inorganic acid (salt), the inorganic acid (salt) is contained in an amount of preferably 0.001 mass % to 2.0 mass %, more preferably 0.005 mass % to 1.5 mass %, even more preferably 0.008 mass % to 1.2 mass %, and particularly preferably 0.01 mass % to 1.0 mass %, relative to a total amount of the water-absorbing resin containing, for example, an additive. The inorganic acid (salt) that is contained in an amount of 0.005% mass % or more makes it possible to suitably remove an odor substance (volatile component). The inorganic acid (salt) that is contained in an amount of 1.5 mass % or less makes it possible to suitably maintain physical properties of a resultant water-absorbing resin, such as water absorption performance (including whiteness, AAP, etc.).

[2-3] Physical Properties of Water-Absorbing Resin

The water-absorbing resin composition according to an embodiment of the present invention has an absorption capacity without load (CRC) of preferably 23 g/g or more, more preferably 25 g/g or more, even more preferably 27 g/g or more, and particularly preferably 28 g/g or more. The CRC preferably has a high upper limit. However, from the viewpoint of balance with other physical properties, the upper limit of the CRC is preferably 50 g/g or less, more preferably 45 g/g or less, even more preferably 40 g/g or less, and particularly preferably 35 g/g or less.

The water-absorbing resin according to an embodiment of the present invention has an absorption capacity under load (AAP) of preferably 15 g/g or more, more preferably 17 g/g or more, even more preferably 20 g/g or more, particularly preferably 23 g/g or more, and most preferably 24 g/g or more. The AAP has an upper limit that is not particularly limited. However, the upper limit is preferably 50 g/g or less from the viewpoint of balance with other physical properties.

In a case where the AAP is 15 g/g or more, an amount of leakage of liquid from an absorbent body to which pressure is applied (generally, referred to as "Re-Wet") can be prevented or reduced. The water-absorbing resin that has an AAP of 15 g/g or more is therefore suitable for an absorbent body of a sanitary material such as a disposable diaper. Note that the AAP can be controlled on the basis of, for example, a particle size and/or a surface-crosslinking agent.

The water-absorbing resin according to an embodiment of the present invention has a saline flow conductivity (SFC) of preferably $1 \times 10^{-7}$ cm$^3$·sec/g or more, more preferably $10 \times 10^{-7}$ cm$^3$·sec/g or more, even more preferably $20 \times 10^{-7}$ cm$^3$·sec/g or more, and particularly preferably $30 \times 10^{-7}$ cm$^3$·sec/g or more. The SFC preferably has an upper limit that is as high as possible, and the upper limit is not particularly limited.

The water-absorbing resin according to an embodiment of the present invention has a water absorption speed, as measured by a Vortex method, of preferably 60 seconds or less, more preferably 45 seconds or less, even more preferably 35 seconds or less, particularly preferably 33 seconds or less, and most preferably 30 seconds or less. The water absorption speed preferably has a lower limit that is as low as possible, and the lower limit is not particularly limited.

The water-absorbing resin according to an embodiment of the present invention has a permeability dependent absorption under pressure (PDAUP) of preferably 10 g/g or more, more present invention 12 g/g or more, and even more preferably 15 g/g or more. The PDAUP preferably has an upper limit that is as high as possible, and the upper limit is not particularly limited.

The water-absorbing resin according to an embodiment of the present invention has a specific surface area of preferably 20 m$^2$/kg or more, more preferably 25 m$^2$/kg or more, more preferably 27 m$^2$/kg or more, even more preferably 30 m$^2$/kg or more, and still more preferably 32 m$^2$/kg or more. The water-absorbing resin that has a specific surface area of 20 m$^2$/kg or more makes it possible to maintain physical properties such as water absorption performance. That is, it is possible to produce a water-absorbing resin that has a higher water absorption speed.

The water-absorbing resin according to an embodiment of the present invention has a solid content of preferably 80 mass % or more, more preferably 85 mass % or more, even more preferably 90 mass % or more, particularly preferably 92 mass % or more, and most preferably 95 mass % or more. The solid content that is 80 mass % or more makes it possible to suitably maintain physical properties of a resultant water-absorbing resin, such as water absorption performance (including whiteness, AAP, etc.).

The water-absorbing resin according to an embodiment of the present invention preferably has a particulate shape. The water-absorbing resin that is particulate can have, for example, a non-uniformly pulverized shape (non-uniform shape), a spherical shape, a fibrous shape, a bar shape, a substantially spherical shape, or a flat shape. In consideration of use for a sanitary product such as a diaper for a child, the water-absorbing resin more preferably has a non-uniform shape out of the above-described particle shapes, in view of a diffusion property of a liquid (urine), difficulty of drop of the water-absorbing resin from pulp, and the like.

[2-4] Use of Water-Absorbing Resin

The water-absorbing resin according to an embodiment of the present invention is a water-absorbing resin that while maintaining water-absorbing resin physical properties such as water absorption performance, has a reduced odor produced during swelling. The water-absorbing resin according to an embodiment of the present invention is therefore suitably used for absorbent articles such as a disposable diaper, an incontinence pad, and a medical pad.

Thus, the present invention also encompasses an absorbent article containing the water-absorbing resin of an aspect of the present invention. An absorbent article according to an embodiment of the present invention includes, for example, an absorbent body containing the water-absorbing resin. The absorbent body can be, for example, a composite containing the water-absorbing resin and a hydrophilic fiber. In a case where the absorbent body is a composite containing the water-absorbing resin and a hydrophilic fiber, the water-absorbing resin is contained in an amount of preferably 60 mass % or more, more preferably 70 mass % or more, and even more preferably 80 mass % or more, relative to a total mass of the absorbent body. With this, while making it possible to achieve a thinner absorbent article, the water-absorbing resin of an aspect of the present invention has a reduced odor produced during swelling, even in a case where a contained amount of a hydrophilic fiber etc. that adsorbs an odor is reduced. This allows an amount of odor produced to be suitably reduced.

Specific examples of the absorbent article according to an embodiment of the present invention include a liquid-permeable top sheet to be so positioned as to be adjacent to the body of a wearer; a liquid-impermeable back sheet to be so positioned as to be far from the body of the wearer and adjacent to clothes worn by the wearer; and a water-absorbing body including the water-absorbing resin composition and positioned between the top sheet and the back sheet.

[3] Method for Producing Water-Absorbing Resin

A method for producing the water-absorbing resin according to an embodiment of the present invention is not particularly limited provided that the method makes it possible to obtain the water-absorbing resin (described earlier). The following description will specifically discuss embodiments of the method for producing the water-absorbing resin according to an aspect of the present invention.

[3-1] Embodiment 1

A method for producing a water-absorbing resin according to Embodiment 1 of the present invention is a method for producing a water-absorbing resin, including the step of adding a water-based liquid in a droplet state to a surface-crosslinked water-absorbing resin so that the surface-crosslinked water-absorbing resin to which the water-based liquid has been added has a moisture content of 7.5 mass % or more, and then drying the surface-crosslinked water-absorbing resin, to which the water-based liquid has been added, so that the moisture content is reduced by an amount of 7.5 mass % or more within one hour.

The method for producing the water-absorbing resin according to Embodiment 1 of the present invention is preferably a method for producing the water-absorbing resin, the method being a method for producing a water-absorbing resin, including one or more of the following steps i) to iii):
  i) adding a water-based liquid in a droplet state to the water-absorbing resin that has a specific surface area of 25 m$^2$/kg or more;

ii) adding a water-based liquid in a droplet state so that the water-absorbing resin has a moisture content of 10 mass % or more; and iii) adding a volatile component reducing agent.

The method for producing the water-absorbing resin according to Embodiment 1 of the present invention may be a method for producing the water-absorbing resin, including at least one of the following steps (A) and (B):

(A) adding a water-based liquid in a droplet state to the surface-crosslinked water-absorbing resin that has a specific surface area of 25 $m^2$/kg or more; and (B) successively including a polymerization step, a drying step of drying a hydrogel having been obtained in the polymerization step, and a surface-crosslinking step, and adding a volatile component reducing agent at or after an end of the polymerization step.

The method for producing the water-absorbing resin according to Embodiment 1 of the present invention preferably includes (A) adding a water-based liquid in a droplet state to the surface-crosslinked water-absorbing resin that has a specific surface area of 25 $m^2$/kg or more, and particularly preferably includes (A) adding a water-based liquid in a droplet state to the surface-crosslinked water-absorbing resin that has a specific surface area of 25 $m^2$/kg or more and (B) successively including a polymerization step, a drying step of drying a hydrogel having been obtained in the polymerization step, and a surface-crosslinking step, and adding a volatile component reducing agent at or after an end of the polymerization step.

The method for producing a water-absorbing resin according to Embodiment 1 of the present invention is particularly preferably a method for producing a water-absorbing resin, including the step of adding a water-based liquid in a droplet state to a surface-crosslinked water-absorbing resin having a specific surface area of 25 $m^2$/kg or more so that the surface-crosslinked water-absorbing resin to which the water-based liquid has been added has a moisture content of 7.5 mass % or more, and then drying the surface-crosslinked water-absorbing resin, to which the water-based liquid has been added, so that the moisture content is reduced by an amount of 7.5 mass % or more within one hour.

For convenience, in the following description, the step of "adding a water-based liquid in a droplet state to a water-absorbing resin so that the water-absorbing resin to which the water-based liquid has been added has a moisture content of 7.5 mass % or more" is expressed as a "water-based liquid adding step", and the step of "drying the surface-crosslinked water-absorbing resin, to which the water-based liquid has been added, so that the moisture content is reduced by an amount of 7.5 mass % or more within one hour" is expressed as "a drying step following addition of the water-based liquid".

In the present Embodiment 1, the volatile component reducing agent is as has been described in [Polyacrylic acid (salt)-based water-absorbing resin] (described earlier). The step of adding a volatile component reducing agent is as described in [3-3] Embodiment 3" (described later).

[3-1-1] Water-Based Liquid Adding Step

The water-based liquid adding step of the present Embodiment 1 is a step of adding a water-based liquid in a droplet state to a surface-crosslinked water-absorbing resin (preferably a water-absorbing resin having a specific surface area of 25 $m^2$/kg or more) so that the surface-crosslinked water-absorbing resin to which the water-based liquid has been added has a moisture content of 7.5 mass % or more. That is, this step is a step of allowing a surface-crosslinked water-absorbing resin to have a higher moisture content.

In an embodiment of the present invention, the water-based liquid is preferably water, and is more preferably an aqueous solution containing the volatile component reducing agent (described earlier). The water-based liquid that contains the volatile component reducing agent makes it possible to obtain a water-absorbing resin that has a lower volatile component concentration. Furthermore, the water-based liquid may contain impurities such as an organic component and an electrically conductive substance. Note, however, that the impurities may inhibit an effect of the present invention. Thus, the water-based liquid preferably contains small amounts of the impurities (in particular, impurities that may inhibit the effect of the present invention). Note that such impurities do not include the volatile component reducing agent.

In an embodiment of the present invention, in a case where the water-based liquid contains, as impurities, an organic component that may inhibit the effect of the present invention, the organic component may be contained in the water-based liquid at a concentration of 1000 ppm or less, preferably 500 ppm or less, even more preferably 200 ppm or less, and particularly preferably 100 ppm or less. In a case where the organic component is contained in the water-based liquid at a concentration in any of the above ranges, (i) there is no fear that presence of the organic component may inhibit the effect of the present invention. Furthermore, (ii) since a smaller amount of an organic component that is derived from impurities remains in a water-absorbing resin produced by a production method according to Embodiment 1 of the present invention, it is possible to further reduce production of an odor caused by the organic component.

Note here that examples of the organic component that may inhibit the effect of the present invention include aliphatic hydrocarbons (e.g., n-heptane and cyclohexane), aromatic hydrocarbons (e.g., benzene, toluene, and xylene), alcohols (e.g., ethanol and isopropanol), and carboxylic acid-based copolymers. The concentration of the organic component contained in the water-based liquid intends to mean a total amount of these organic components.

In an embodiment of the present invention, the water-based liquid that contains an electrically conductive substance may cause a decrease in water absorption performance of the water-absorbing resin produced by the production method according to Embodiment 1 of the present invention. This is because the electrically conductive substance that remains in the water-absorbing resin reduces osmotic pressure under which the water-absorbing resin absorbs urine etc. Furthermore, an electrically conductive substance contained in the water-based liquid may, depending on its kind, cause production of an odor (that is, may inhibit the effect of the present invention). Note here that an amount of an electrically conductive substance contained in a water-based liquid can be evaluated by an electric conductivity of the water-based liquid. A water-based liquid that contains an electrically conductive substance (e.g., ions) in a larger amount has a higher electric conductivity. Thus, the electric conductivity of the water-based liquid is not essential provided that the electric conductivity does not inhibit the effect of the present invention. The electric conductivity only needs to be 5 mS/cm or less, preferably 2 mS/cm or less, more preferably 1 mS/cm or less, and particularly preferably 500 µS/cm or less. The expression "a water-based liquid has an electric conductivity of 5 mS/cm or less" means that an amount in which an electrically conductive substance is contained in the water-based liquid is small (is so small as to cause no fear that the electrically conductive substance may inhibit the effect of the present invention). Thus, the electric conductivity that is preferably 5 mS/cm or less makes it possible to further reduce (i) a decrease in water absorption performance of a water-absorbing resin due to an electrically conductive substance remaining in the water-absorbing resin and (ii) production of an odor. Examples of an electrically conductive substance that may inhibit the effect of the present invention include magnesium ions, calcium ions, and aluminum ions.

Note that a physiological saline (0.9 mass % saline solution) has an electric conductivity of approximately 15.7 mS/cm, a 0.69 mass % saline solution for use in measurement of the saline flow conductivity (SFC) has an electric conductivity of approximately 12.5 mS/cm, tap water has an electric conductivity of 100 µS/cm to 200 µS/cm, and deionized water (dw) has an electric conductivity of approximately 1 µS/cm. The above electric conductivities are values measured at a liquid temperature of 25° C.

As described earlier, the water-based liquid is preferably water that contains small amounts of impurities such as an organic component and an electrically conductive substance, and is particularly preferably an aqueous solution that contains a volatile component reducing agent and that contains impurities such as an organic component and an electrically conductive substance in amounts so small as not to inhibit the effect of the present invention.

In the water-based liquid adding step, a water-based liquid in a droplet state is added to a water-absorbing resin so that the water-absorbing resin to which the water-based liquid has been added has a moisture content of 7.5 mass % or more, preferably 10 mass % or more, more preferably 15 mass % or more, and even more preferably 20 mass % or more. Addition of the water-based liquid in the droplet state makes it possible to uniformly add the water-based liquid to the water-absorbing resin. During and/or after addition of the water-based liquid in the droplet state, the water-absorbing resin is stirred as appropriate. In a case where the water-based liquid in the droplet state is added to the water-absorbing resin so that the water-absorbing resin to which the water-based liquid has been added has a moisture content of 7.5 mass % or more, a substance that causes an odor (hereinafter expressed as "an odor substance", which is intended to mean a volatile component) can be suitably removed in the drying step carried out later following addition of the water-based liquid. In the water-based liquid adding step, the water-based liquid in the droplet state is added to the water-absorbing resin so that the water-absorbing resin to which the water-based liquid has been added has a moisture content of 45 mass % or less, and more preferably 35 mass % or less. In the present invention, the term "moisture content" means a ratio of a mass (mass %) of a water-based liquid to a mass of the entire water-absorbing resin obtained by adding together a mass of a solid content and a mass of the water-based liquid.

In a case where the water-based liquid is excessively added in the water-based liquid adding step, an aggregate in which swollen water-absorbing resins have adhered to each other may be produced. Furthermore, in the drying step carried out later following addition of the water-based liquid, it takes a long time to remove a sufficient amount of the water-based liquid from a water-absorbing resin. This causes the water-absorbing resin to be present in a swollen state for a long time. Thus, an aggregate in which swollen water-absorbing resins have adhered to each other may be produced in the drying step following addition of the water-based liquid. In a case where the aggregate is produced, it may be impossible to sufficiently remove the water-based liquid inside the aggregate in the drying step following addition of the water-based liquid. That is, in a case where the aggregate is produced, a resultant water-absorbing resin may have lower physical properties such as water absorption performance. Furthermore, in a case where crushing is carried out so that the aggregate is adjusted so as to have a desired particle size distribution (described later), a surface-crosslinked layer of the water-absorbing resin may be destroyed, and the water-absorbing resin may also have lower physical properties. Moreover, in a case where the aggregate is produced and the water-absorbing resin to which the water-based liquid has been added is dried by stirring, a heavier load may be imposed on a stirring drying device for carrying out the stirring, and it may be impossible, depending on a condition, to carry out the stirring.

In the water-based liquid adding step, in a case where the water-absorbing resin to which the water-based liquid has been added has a moisture content in any of the above-described ranges, the swollen state of the water-absorbing resin can be reduced at an early stage in the drying step carried out later following addition of the water-based liquid. Thus, it is possible to suitably prevent production of the aggregate and consequently to maintain physical properties of a resultant water-absorbing resin, such as water absorption performance.

An amount of the water-based liquid that is added in the droplet state in the water-based liquid adding step can be easily set by calculation on the basis of the moisture content of the water-absorbing resin to which the water-based liquid has been added, i.e., a targeted moisture content. For example, in order to set, to 7.5 mass %, the moisture content of the water-absorbing resin to which the water-based liquid has been added, it is only necessary to add 7.5 parts by mass of the water-based liquid to 92.5 parts by mass of the water-absorbing resin (solid content) to which the water-based liquid has not been added.

In the water-based liquid adding step, a temperature of the water-absorbing resin (powder temperature) as measured immediately before the water-based liquid is added to the water-absorbing resin is controlled at preferably 90° C. to 160° C., and more preferably 90° C. to 140° C. Furthermore, the temperature of the water-absorbing resin (powder temperature) as measured immediately after the water-based liquid has been added to the water-absorbing resin is controlled at preferably 60° C. to 150° C., and more preferably 70° C. to 140° C. Moreover, the temperature of the water-absorbing resin to which the water-based liquid has been added (powder temperature) is controlled, preferably within 30 minutes, at 80° C. to 160° C., and more preferably 90° C. to 160° C. That is, the drying step following addition of the water-based liquid is carried out, preferably within 30 minutes, with respect to the water-absorbing resin to which the water-based liquid has been added.

In the water-based liquid adding step, a temperature of the water-based liquid as measured immediately before the water-based liquid is added is controlled at preferably 5° C. to 90° C., and more preferably 10° C. to 70° C. Note that the water-based liquid is preferably added to the water-absorbing resin in a shorter time.

In a case where the temperature of the water-absorbing resin to which the water-based liquid has not been added (powder temperature), the temperature of the water-absorbing resin to which the water-based liquid has been added (powder temperature), and the temperature of the water-based liquid to be added are controlled as described earlier, the water-based liquid added rapidly permeates into particles of the water-absorbing resin. This results in higher affinity between the water-based liquid and an odor substance (volatile component). Thus, in the drying step carried out later following addition of the water-based liquid, it is possible to suitably remove the odor substance (volatile component) together with the water-based liquid while maintaining water-absorbing resin physical properties such as water absorption performance.

[3-1-2] Drying Step Following Addition of Water-Based Liquid

In Embodiment 1, a drying step following addition of a water-based liquid is a step of drying a water-absorbing resin, to which a water-based liquid has been added, so that a moisture content of the water-absorbing resin is reduced by an amount of 7.5 mass % or more within one hour. That is, this step is a step of reducing a moisture content of a surface-crosslinked water-absorbing resin by 7.5 mass % or more within one hour.

For example, a device such as a stirring drying device may be used to carry out the water-based liquid adding step and the drying step following addition of the water-based liquid as continuous steps or separate steps. That is, the method for producing the water-absorbing resin according to Embodiment 1 of the present invention may be of a continuous type in which the water-based liquid adding step and the drying step following addition of the water-based liquid are carried out as continuous steps, or of a batch type in which the water-based liquid adding step and the drying step following addition of the water-based liquid are carried out as separate steps. In view of efficiency of producing the water-absorbing resin, the method for producing the water-absorbing resin is more preferably of a continuous type.

In the drying step following addition of the water-based liquid, the water-absorbing resin to which the water-based liquid has been added is dried so that the moisture content is reduced by an amount of 7.5 mass % or more, preferably 10.0 mass % or more, more preferably 15.0 mass % or more, and particularly preferably 20.0 mass % or more, within one hour. In a case where the water-based liquid is added in the water-based liquid adding step so that the water-absorbing resin has a moisture content of 27.5 mass % or more, the water-absorbing resin to which the water-based liquid has been added is preferably dried so that the water-absorbing resin has a moisture content of 20.0 mass % or less within one hour. This makes it possible to suitably remove, together with the water-based liquid, an odor substance (volatile component) contained in the water-absorbing resin. The moisture content that is reduced in a larger amount allows the odor substance (volatile component) to be removed in a larger amount together with the water-based liquid. This makes it possible to further reduce production of an odor caused by the odor substance (volatile component). Note here that the expression "within one hour" means in the present invention that one hour or less has elapsed since addition of the water-based liquid to the water-absorbing resin.

In the drying step following addition of the water-based liquid, unless the water-absorbing resin is dried so that the moisture content is reduced by an amount of 7.5 mass % or more (in a case where the moisture content is reduced by an amount of less than 7.5 mass %) within one hour, and, in the water-based liquid adding step, in a case where the water-based liquid is added to the water-absorbing resin so that the water-absorbing resin to which the water-based liquid has been added has a moisture content of 27.5 mass % or more and unless the water-absorbing resin to which the water-based liquid has been added is dried so as to have a moisture content of 20.0 mass % or less within one hour, the water-absorbing resin will be present in a swollen state for a long time. Thus, an aggregate in which swollen water-absorbing resins have adhered to each other may be produced. In a case where the aggregate is produced, it may be impossible to sufficiently remove the water-based liquid inside the aggregate in the drying step following addition of the water-based liquid. That is, in a case where the aggregate is produced, a resultant water-absorbing resin may have lower physical properties such as water absorption performance. Furthermore, in a case where crushing is carried out so that the aggregate is adjusted so as to have a desired particle size distribution (described later), a surface-crosslinked layer of the water-absorbing resin may be destroyed, and the water-absorbing resin may also have lower physical properties. Moreover, in a case where the aggregate is produced and the water-absorbing resin to which the water-based liquid has been added is dried by stirring, a heavier load may be imposed on a stirring drying device for carrying out the stirring, and it may be impossible, depending on a condition, to carry out the stirring.

The drying step following addition of the water-based liquid starts to be carried out after the water-based liquid adding step preferably within a shorter time, and more preferably within 30 minutes. The water-based liquid adding step and the drying step following addition of the water-based liquid are most preferably continuously carried out. This allows the water-absorbing resin to be in a swollen state for a short time.

In the drying step following addition of the water-based liquid, the water-absorbing resin to which the water-based liquid has been added is preferably dried under a stirring and/or air flow condition(s). This allows an efficient reduction in moisture content of the water-absorbing resin. A stirring drying device for carrying out the stirring may be a known stirring and drying device, and an air flow generating device for generating the air flow may be a known air flow generating device.

In the drying step following addition of the water-based liquid, the water-absorbing resin to which the water-based liquid has been added is dried at a pressure reduction level of 0.0 kPa to 10.0 kPa, and more preferably 0.1 kPa to 5.0 kPa. This allows an efficient reduction in moisture content of the water-absorbing resin. Examples of a method for controlling the pressure reduction level in any of the above ranges include a method in which a dryer is used to carry out the drying step following addition of the water-based liquid, and an exhaust blower, a vacuum pump, and/or the like is/are used to control a pressure inside the dryer in any of the above ranges. By controlling the pressure reduction level in any of the above ranges, it is possible to prevent or reduce scattering of the water-absorbing resin and fine particles thereof due to an air flow that occurs during pressure reduction. The pressure reduction level that is made excessively high is not preferable. This is because such a pressure reduction level makes the drying step complicated and requires large scale equipment to be used during the drying step.

In the drying step following addition of the water-based liquid, a device for reducing the moisture content of the water-absorbing resin has a temperature preferably 60° C. to 160° C., more preferably 80° C. to 160° C., and even more preferably 100° C. to 150° C. The temperature of the device for reducing the moisture content of the water-absorbing resin means a temperature of an inner wall of a dryer in a case where for example the dryer is used to carry out the drying step following addition of the water-based liquid, and means a temperature of an air flow in a case where for example the air flow is used to carry out the drying step following addition of the water-based liquid. In a case where a temperature in any of the above preferable ranges is applied as the temperature of the device for reducing the moisture content of the water-absorbing resin, it is possible to achieve a shorter drying time and consequently to achieve higher productivity of a water-absorbing resin. It is also possible to prevent or reduce a deterioration in water-absorbing resin at a high temperature and consequently to suitably remove an odor substance (volatile component) together with the water-based liquid from a resultant water-absorbing resin while maintaining physical properties of the water-absorbing resin, such as water absorption performance. In the following description, the temperature of the device for reducing the moisture content of the water-absorbing resin is also referred to as a "drying temperature".

In the drying step following addition of the water-based liquid, the water-absorbing resin to which the water-based liquid has been added is dried for a drying time of preferably 5 minutes to 1 hour, and more preferably 10 minutes to 50 minutes so that the moisture content is reduced by an amount of 7.5 mass % or more. In a case where drying is carried out within any of the above time periods, it is possible to achieve a shorter drying time, prevent or reduce a deterioration in water-absorbing resin due to drying at a high temperature, and prevent or reduce damage to the water-absorbing resin due to stirring or contact with an air flow for a longer time. Furthermore, in a case where drying is carried out so that the drying time is 5 minutes or longer, it is possible to efficiently remove an odor substance (volatile component).

As described earlier, the drying temperature and the drying time are set as appropriate so that the moisture content is reduced by a desired amount. However, in a case where drying is carried out at a low temperature for a long time, a crosslinked layer of a water-absorbing resin may be destroyed by mechanical damage occurring in a dryer, and the water-absorbing resin may have lower physical properties. In contrast, in a case where drying is carried out at a high temperature for a short time, destruction of a surface-crosslinked layer as mentioned above is prevented or reduced. However, it is feared that a water-absorbing resin may deteriorate due to the high temperature. The drying temperature and the drying time therefore preferably simultaneously satisfy the above respective ranges.

[3-1-3] Surface-Crosslinked Water-Absorbing Resin

The surface-crosslinked water-absorbing resin to be subjected to the water-based liquid adding step has a specific surface area of preferably 25 m$^2$/kg or more, more preferably 27 m$^2$/kg or more, even more preferably 30 m$^2$/kg or more, still more preferably 32 m$^2$/kg or more, and particularly preferably 35 m$^2$/kg or more. The specific surface area of the surface-crosslinked water-absorbing resin hardly changes even after the water-based liquid adding step and the drying step following addition of the water-based liquid are carried out. Thus, the surface-crosslinked water-absorbing resin, which has a specific surface area of 25 m$^2$/kg or more as measured after the water-based liquid adding step and the drying step following addition of the water-based liquid are carried out, can maintain physical properties such as water absorption performance. That is, even after the water-based liquid adding step and the drying step following addition of the water-based liquid are carried out with respect to a water-absorbing resin that has a higher water absorption speed, the water-absorbing resin can maintain the water absorption speed.

The surface-crosslinked water-absorbing resin to be subjected to the water-based liquid adding step has an absorption capacity without load (CRC) of preferably 23 g/g or more, more preferably 25 g/g or more, even more preferably 27 g/g or more, and particularly preferably 28 g/g or more. The CRC preferably has an upper limit that is as high as possible. However, from the viewpoint of balance with other physical properties, the upper limit of the CRC is preferably 50 g/g or less, more preferably 40 g/g or less, and even more preferably 35 g/g or less.

The surface-crosslinked water-absorbing resin to be subjected to the water-based liquid adding step has an absorption capacity under load (AAP) of preferably 15 g/g or more, more preferably 17 g/g or more, even more preferably 20 g/g or more, and particularly preferably 23 g/g or more. The AAP preferably has an upper limit that is as high as possible. However, from the viewpoint of balance with other physical properties, the upper limit of the AAP is preferably 50 g/g or less, more preferably 40 g/g or less, and even more preferably 30 g/g or less.

The surface-crosslinked water-absorbing resin to be subjected to the water-based liquid adding step has a water absorption speed, as measured by a Vortex method, of preferably 35 seconds or less, more preferably 33 seconds or less, and even more preferably 30 seconds or less. The water absorption speed preferably has a lower limit that is as low as possible, and the lower limit is not particularly limited.

The surface-crosslinked water-absorbing resin to be subjected to the water-based liquid adding step has a saline flow conductivity (SFC) of preferably $10 \times 10^{-7}$ cm$^3$·sec/g or more, more preferably $20 \times 10^{-7}$ cm$^3$·sec/g or more, and even more preferably $30 \times 10^{-7}$ cm$^3$·sec/g or more. The SFC preferably has an upper limit that is as high as possible, and the upper limit is not particularly limited.

The surface-crosslinked water-absorbing resin to be subjected to the water-based liquid adding step has a residual monomer amount of preferably 1000 ppm or less, more preferably 700 ppm or less, and even more preferably 500 ppm or less. The residual monomer amount preferably has a lower limit that is as low as possible, and the lower limit is not particularly limited.

In a case where physical property values of the surface-crosslinked water-absorbing resin to be subjected to the water-based liquid adding step are set preferably in the above respective ranges, a water-absorbing resin that has physical property values in respective suitable ranges can be obtained after the water-based liquid adding step and the drying step following addition of the water-based liquid are carried out.

[3-1-4] Method for Producing Surface-Crosslinked Water-Absorbing Resin

The surface-crosslinked water-absorbing resin to be subjected to the water-based liquid adding step can be produced by a known production method. Examples of the production method include a method shown below. Note, however, that a method for producing the surface-crosslinked water-absorbing resin does not need to include all steps shown below, and only need to include at least the polymerization step, the drying step, and the surface-crosslinking step. Furthermore, the method for producing the water-absorbing resin according to Embodiment 1 of the present invention can include the steps shown below, but does not need to include all the steps.

[3-1-4-1] Step of Preparing Aqueous Monomer Solution

This step is a step of preparing an aqueous solution of a monomer composition (hereinafter may be referred to as an "aqueous monomer solution") containing: a monomer containing an acrylic acid (salt)-based monomer (described earlier); and at least one internal crosslinking agent (described earlier). It is also possible to use a monomer slurry liquid. For convenience, however, the present specification will describe an aqueous monomer solution.
(Monomer)

A monomer used in this step is as has been described in [Polyacrylic acid (salt)-based water-absorbing resin].
(Neutralization with Basic Compound)

In an embodiment of the present invention, it is preferable that acrylic acid be partially neutralized with use of a basic compound. In other words, a water-absorbing resin in which acid groups of polyacrylic acid are partially neutralized is preferable in an embodiment of the present invention.

Examples of the basic compound include a carbonate or bicarbonate of an alkali metal, a hydroxide of an alkali metal, ammonia, and organic amine. Out of such examples, from the viewpoint of water absorption performance of the water-absorbing resin, a strongly basic compound is selected. From the viewpoint of handleability, the basic compound is preferably in the form of an aqueous solution.

A timing of the above-described neutralization is not limited. The neutralization can be carried out before, during, or after polymerization. The neutralization may be carried out at a plurality of timings or a plurality of number of times. From the viewpoint of efficiency of producing the water-absorbing resin, continuous type neutralization is preferable.

In a case where acrylic acid (salt) is to be used in an embodiment of the present invention, the neutralization rate of the acrylic acid (salt) is preferably 10 mol % or more, more preferably 40 mol % or more, even more preferably 50 mol % or more, particularly preferably 60 mol % or more, preferably 90 mol % or less, more preferably 85 mol % or less, even more preferably 80 mol % or less, and particularly preferably 75 mol % or less, relative to the acid groups of the monomer. Setting the neutralization rate to be within the above range makes it possible to prevent a decrease in the water absorption performance of the water-absorbing resin. The above neutralization rate is applied to neutralization carried out before the polymerization, neutralization carried out during the polymerization, and neutralization carried out after the polymerization. The above neutralization rate is applied similarly to a water-absorbing resin.

Note here that the neutralization rate of the polyacrylic acid (salt)-based resin refers to a ratio of the number of moles of acid groups that have been partially neutralized and that are included in acid groups included in the polyacrylic acid (salt)-based resin to the number of moles of the acid groups.
(Internal Crosslinking Agent)

An internal crosslinking agent used in this step and an amount of the internal crosslinking agent used are as has been described in [Polyacrylic acid (salt)-based water-absorbing resin] (described earlier).

In an embodiment of the present invention, a timing at which the internal crosslinking agent is added only needs to be a timing that allows a polymer to be uniformly crosslinked, and a method of adding the internal crosslinking agent to an aqueous monomer solution before polymerization and to a hydrogel polymer during or after polymerization is taken as an example. Particularly, a method of adding a predetermined amount of internal crosslinking agent to an aqueous monomer solution in advance is preferable.
(Substance(s) Added to Aqueous Monomer Solution)

In an embodiment of the present invention, from the viewpoint of improving physical properties of the water-absorbing resin, any of the below substances can be added to the aqueous monomer solution, the solution during the reaction, or the solution after the reaction at at least one of the following times: during preparation of the aqueous monomer solution; during the polymerization reaction; during the crosslinking reaction; after the polymerization reaction; and after the crosslinking reaction.

Specific examples of the substance which can be added include: a hydrophilic polymer such as starch, a starch derivative, cellulose, a cellulose derivative, polyvinyl alcohol (PVA), polyacrylic acid (salt), and crosslinked polyacrylic acid (salt); and a compound such as a carbonate, an azo compound, a foaming agent which generates any of various types of gas bubbles, a surfactant, a chelating agent, and a chain transfer agent.

The amount of the hydrophilic polymer added is preferably 50 mass % or less, more preferably 20 mass % or less, even more preferably 10 mass % or less, particularly preferably 5 mass % or less, preferably 0 mass % or more, and more preferably more than 0 mass %, relative to the aqueous monomer solution. The amount of the compound added is preferably 5 mass % or less, more preferably 1 mass % or less, even more preferably 0.5 mass % or less, preferably 0 mass % or more, and more preferably more than 0 mass %, relative to the aqueous monomer solution.

In a case where a water-soluble resin or a water-absorbing resin is used as the hydrophilic polymer, a graft polymer or a water-absorbing resin (for example, a copolymer produced from starch and acrylic acid (salt), or a copolymer produced from PVA and acrylic acid (salt)) can be obtained. These graft polymers and water-absorbing resin are also encompassed in the scope of the polyacrylic acid (salt)-based water-absorbing resin.
(Monomer Composition Concentration)

By variously selecting, in accordance with an objective, monomers as described above, internal crosslinking agents as described above, and other substances and components as described above (hereinafter referred to as "monomer components") and then mixing the selected monomers, internal crosslinking agents, and other substances and components together in respective amounts defined so as to fall within the above-described ranges, a mixture of the monomer components (monomer composition) is prepared, and an aqueous solution of the monomer composition (called an "aqueous monomer solution") is prepared by placing the mixture in water. Note that, in Embodiment 1 of the present invention, instead of employing an aqueous monomer solution, it is possible to employ a mixed monomer solution containing water and a hydrophilic solvent.

Further, from the viewpoint of the physical properties of the water-absorbing resin, the concentration of the total of the monomer composition is preferably 10 mass % or more, more preferably 20 mass % or more, even more preferably 30 mass % or more, preferably 80 mass % or less, more preferably 75 mass % or less, and even more preferably 70 mass % or less. The concentration of the monomer composition is calculated by use of the following Formula (A):

Monomer composition concentration (mass %)=
[(mass of monomer composition)/(mass of
aqueous monomer solution)]×100    Formula (A).

Note that in Formula (A), the "mass of the aqueous monomer solution" does not include a mass of a graft component, a mass of the water-absorbing resin, or a mass of a hydrophobic organic solvent used in reversed phase suspension polymerization.

[3-1-4-2] Polymerization Step

This step is a step of polymerizing an aqueous monomer solution so that a hydrogel polymer (crosslinked hydrogel polymer) is obtained. Preferably, this step is a step of polymerizing the aqueous monomer solution obtained in the step of preparing the aqueous monomer solution so that a crosslinked hydrogel polymer (hereinafter merely referred to as "hydrogel") is obtained, the aqueous monomer solution containing a monomer and at least one polymerizable internal crosslinking agent, the monomer containing acrylic acid (salt) as a main component.
(Polymerization Initiator)

As a polymerization initiator used in an embodiment of the present invention, one (or two or more) of the polymerization initiators used in an ordinary water-absorbing resin production can be selected and used in accordance with, for example, the type of monomer to be polymerized and polymerization conditions. Examples of the polymerization initiator include a pyrolysis-type initiator and a photolytic-type initiator.

Examples of the pyrolysis-type initiator include persulfates such as sodium persulfate, potassium persulfate, and ammonium persulfate; peroxides such as hydrogen peroxide, t-butyl peroxide, and methyl ethyl ketone peroxide; and azo compounds such as an azonitrile compound, an azoamidine compound, a cyclic azoamidine compound, an azoamide compound, an alkylazo compound, 2,2'-azobis(2-amidinopropane) dihydrochloride, and 2,2'-azobis[2-(2-imidazolin-2-yl) propane]dihydrochloride.

Examples of the photolytic-type initiator include benzoin derivatives, benzyl derivatives, acetophenone derivatives, benzophenone derivatives, and azo compounds.

Of these polymerization initiators, persulfates are preferable, in consideration of cost and an ability to reduce a residual monomer. Alternatively, an oxidizing polymerization initiator which is, for example, any of the above-listed persulfates or any of the above-listed peroxides and a reducing agent (for facilitating decomposition of the oxidizing polymerization initiator) can be used in combination to allow the combination to serve as a redox-type initiator. Examples of the reducing agent include a (bi)sulfurous acid (salt) such as sodium sulfite and sodium hydrogen sulfite, a reducing metal (salt) such as L-ascorbic acid (salt) and ferrous salt, and an amine.

The amount of the polymerization initiator used is preferably 0.001 mol % or more, more preferably 0.010 mol % or more, preferably 1.000 mol % or less, more preferably 0.500 mol % or less, and even more preferably 0.100 mol % or less, relative to the monomer composition excluding the internal crosslinking agent. Further, the amount of the reducing agent used is preferably 0.0001 mol % or more, more preferably 0.0005 mol % or more, preferably 0.0200 mol % or less, and more preferably 0.0150 mol % or less, relative to the monomers excluding the internal crosslinking agent. Setting the amounts of polymerization initiator and reducing agent used to be within the above ranges makes it possible to obtain a water-absorbing resin having a desired water absorption performance.

In an embodiment of the present invention, the polymerization reaction may be initiated by irradiation of an active energy ray such as a radiation ray, an electron ray, and/or an ultraviolet ray. It is also possible to combine irradiation of an active energy ray with the above-described polymerization initiator.
(Form of Polymerization)

Examples of forms of polymerization which can be applied to an embodiment of the present invention include aqueous solution polymerization, reversed phase suspension polymerization, spray polymerization, droplet polymerization, bulk polymerization, and precipitation polymerization. Out of these forms, from the viewpoints of ease of controlling polymerization and the water absorption performance of the water-absorbing resin, the form of polymerization is preferably aqueous solution polymerization or reversed phase suspension polymerization, and more preferably aqueous solution polymerization. Examples of the aqueous solution polymerization are disclosed in, for example, Japanese Patent Application Publication Tokukaihei No. 4-255701. Examples of the reversed phase suspension polymerization are disclosed in, for example, International Publication No. WO 2007/004529 and International Publication No. WO 2012/023433.

Examples of preferable forms of the aqueous solution polymerization include high-temperature-initiating polymerization, high-concentration polymerization, and foaming polymerization. The "high-temperature-initiating polymerization" means a form of polymerization in which a temperature of the aqueous monomer solution at the initiation of polymerization is preferably 35° C. or more, more preferably 40° C. or more, even more preferably 45° C. or more, particularly preferably 50° C. or more, and preferably a temperature that is equal to or lower than a boiling point of the aqueous monomer solution. Further, the "high-concentration polymerization" means a form of polymerization in which a monomer concentration at the initiation of polymerization is preferably 30 mass % or more, more preferably 35 mass % or more, even more preferably 40 mass % or more, particularly preferably 45 mass % or more, and preferably a concentration that is equal to or lower than a saturation concentration of the aqueous monomer solution. The "foaming polymerization" means a form of polymerization in which the aqueous monomer solution to be polymerized contains a foaming agent or gas bubbles. One of these forms of polymerization may be employed alone. Alternatively, two or more of these forms of polymerization may be employed in combination. The form of the aqueous solution polymerization may be of a continuous type or a batch type. Note, however, that the form of the aqueous solution polymerization is preferably of the continuous type from the viewpoint of production efficiency.

Furthermore, examples of the aqueous solution polymerization of the continuous type (described earlier) include: continuous belt polymerization as disclosed in, for example, U.S. Pat. Nos. 4,893,999, 6,906,159, 7,091,253, 7,741,400, 8,519,212, and Japanese Patent Application Publication Tokukai No. 2005-36100; and continuous kneader polymerization as disclosed in, for example, U.S. Pat. No. 6,987,151.

Examples of a method for dispersing gas bubbles in the foaming polymerization include: a method of dispersing gas bubbles by reducing the solubility of gas dissolved in the aqueous monomer solution; a method of introducing gas from an external source and dispersing the gas as gas bubbles; and a method of causing foaming by adding a foaming agent to the aqueous monomer solution. A combination of any of these methods for dispersing gas bubbles may be employed as appropriate in accordance with desired physical properties of the water-absorbing resin.

With regards to a case where a gas is introduced from the external source, examples of the gas include oxygen, air, nitrogen, carbonic acid gas, ozone, and the like, as well as a mixed gas constituted by a mixture of any of these gases. From the viewpoints of polymerizability and cost, preferably used is an inert gas(es) such as nitrogen and carbonic acid gas, and more preferably used is nitrogen.

Examples of the foaming agent that can be used include an azo compound and a solution of an organic or inorganic carbonate, dispersion liquid thereof, or powder thereof having particle diameter of 0.1 μm to 1000.0 μm. Out of these examples, the inorganic carbonate is preferable. Specific examples include a carbonate such as sodium carbonate, ammonium carbonate, and magnesium carbonate, and a bicarbonate.

Subjecting a foam-shaped hydrogel obtained by the foaming polymerization to gel-crushing facilitates drying. Further, a foam-shaped water-absorbing resin makes it possible to improve the water absorption speed of the water-absorbing resin. Whether or not the water-absorbing resin is a foam-shaped water-absorbing resin can be confirmed by observing the pores (for example, pores having a diameter of 1 μm to 100 μm) of the surface of the water-absorbing resin particles by use of an electron microscope. The number of pores per water-absorbing resin particle is preferably 1 or more, more preferably 10 or more, preferably 10,000 or less, and more preferably 1,000 or less, and can be controlled by the foaming polymerization.

[3-1-4-3] Gel-Crushing Step

This step is a step of crushing a hydrogel during and/or after the polymerization step. Specifically, the hydrogel may be crushed in the polymerization step, and alternatively, the hydrogel may be crushed after the polymerization step. In other words, this step is a step of gel-crushing the hydrogel so that a crosslinked particulate hydrogel polymer (hereinafter referred to as "particulate hydrogel") is obtained. This step is called "gel-crushing" to distinguish it from the "pulverization" of the later-described pulverizing step. Further, a target for gel-crushing is not only the hydrogel obtained in the polymerization step and may include a recycled granulated gel (described later), unless particularly mentioned otherwise. The same applies to the other steps, unless particularly mentioned otherwise.

The gel-crushing refers to adjusting the size of the hydrogel so as to be a predetermined size, with use of a kneader, a screw extruder such as a meat chopper, or a gel-crusher such as a cutter mill.

In a case where the hydrogel is to be gel-crushed, it is preferable that preferably hot water be added to a gel crusher. The addition of hot water is preferably carried out since a resulting particulate hydrogel has low tackiness and good air permeability and is thus easy to dry. The hot water has a temperature of preferably 40° C. or more, more preferably 50° C. or more, even more preferably 60° C. or more, and preferably 100° C. or less.

With regards to, for example, the form of the gel-crushing and the operating conditions, a method described in a document(s) describing continuous aqueous solution polymerization is employed in the aqueous solution polymerization. The disclosures of the pamphlet of International Publication No. 2011/126079 can be preferably applied to Embodiment 1 of the present invention. Note that in a case where the form of polymerization is kneader polymerization, the polymerization step and the gel-crushing step are carried out simultaneously. Undergoing the gel-crushing step in Embodiment 1 of the present invention makes it possible to obtain water-absorbing resin having a non-uniformly pulverized shape.

Further, a method for producing a water-absorbing resin in accordance with an embodiment of the present invention is more preferably such that a fine powder recycle step includes: a granulation step of mixing removed fine powder and a water-based liquid so that a granulated gel is obtained; and a granulated gel addition step of adding the granulated gel to a hydrogel in at least one step and/or between steps that is/are carried out after the end of the gel-crushing step until drying is completed in the drying step. In the gel-crushing carried out in the gel-crushing step in Embodiment 1 of the present invention, it is more preferable that gel-grinding energy be controlled appropriately. Even in a case where mixtures of (i) a particulate hydrogel obtained by performing gel-crushing with a predetermined gel-grinding energy described below and (ii) a granulated gel are disposed while being dried with use of a through-flow band-type dryer, the mixtures are less likely to be densely disposed. Thus, as compared with a case where a particulate hydrogel obtained by performing gel-crushing under an ordinary condition, the particulate hydrogel obtained by performing gel-crushing with a predetermined gel-grinding energy described below can be dried in an extremely short time. Furthermore, the particulate hydrogel obtained by performing gel-crushing with a predetermined gel-grinding energy described below is easily harmonized with a granulated gel (described later) and is easily uniformly dried. Moreover, a resultant water-absorbing resin is highly evaluated for its physical properties in terms of a water absorption speed (for example, FSR described in International Publication No. WO 2009/016055 and Vortex described in "Testing method for water absorption rate of super absorbent polymers" in JIS K7224 (1996)).

Here, the term "gel-grinding energy" as used in an embodiment of the present invention refers to mechanical energy per unit mass, the mechanical energy being necessary for a gel-crushing device to gel-crush a hydrogel (i.e., mechanical energy per unit mass of a hydrogel). The gel-grinding energy does not include energy with which to heat or cool a jacket, or energy of water or steam to be introduced. Note that "gel-grinding energy" is abbreviated as "GGE".

In a case where the gel-crushing device is driven by a three-phase alternating current power, GGE is calculated based on the following Formula (I).

$$GGE \text{ [J/g]} = \{\sqrt{3} \times \text{voltage} \times \text{electric current} \times \text{power factor} \times \text{motor efficiency}\}/\{\text{mass of hydrogel introduced into gel crusher per second}\} \quad \text{Formula (I)}$$

The "power factor" and the "motor efficiency" are each a value which is unique to the gel-crushing device and changes depending on, for example, an operation condition of the gel-crushing device and which ranges from 0 to 1. These values can be known by, for example, making inquiries to a manufacturer of the device or the like. In a case where the gel-crushing device is driven by a single-phase alternating current power, GGE can be calculated by replacing "$\sqrt{3}$" with "1" in Formula (I) above. Note that a unit of a voltage is [V], a unit of an electric current is [A], and a unit of mass of a hydrogel is [g/s].

The "power factor" and the "motor efficiency" during gel-crushing are applied to the GGE. Since the electric current value during idling is small, the values of the power factor and the motor efficiency during idling are defined approximately as in Formula (I) above. For example, in a case where a hydrogel is continuously fed by a quantitative feeder, the "mass of hydrogel introduced into gel crusher per second" [g/s] in Formula (I) above refers to a value obtained by conversion into [g/s]. Note, however, that the hydrogel may include a recycled granulated gel as described later.

The gel-grinding energy (GGE) for performing gel-crushing in an embodiment of the present invention is preferably 100 J/g or less, more preferably 80 J/g or less, even more preferably 60 J/g or less, preferably 20 J/g or more, more preferably 25 J/g or more, and even more preferably 30 J/g or more. By controlling the gel-grinding energy within any of the above ranges, it is possible to perform gel-crushing while applying adequate shearing and compressive forces to the hydrogel.

Note that, in a case where the gel-crushing is performed with the use of a plurality of crushers such as using a screw extruder after kneader polymerization or using a plurality of screw extruders, the sum of the energies consumed by the crushers is used as a gel-grinding energy (GGE).

Further, controlling the gel-grinding energy as described above can produce more excellent effect in combination with the addition of hot water having the above temperature. Further, after a normal gel-crushing, gel-crushing based on the gel-grinding energy may be performed.

The particulate hydrogel grain-refined through the gel-crushing step has a particle diameter in a range of preferably 0.1 mm to 10.0 mm, from the viewpoints of ease of drying and physical properties of a resulting water-absorbing resin. Further, the particulate hydrogel has a mass average particle diameter (D50) of preferably 0.1 mm to 5.0 mm, and more preferably 0.1 mm to 2.0 mm. A particulate hydrogel having a mass average particle diameter (D50) falling within the above ranges may be sufficiently dried. In Embodiment 1 of the present invention, a hydrogel to be subjected to the drying step preferably has a mass average particle diameter falling within any of the above ranges, and more preferably satisfies both the above-described particle diameter and the above-described mass average particle diameter.

As to the particle size of the particulate hydrogel, a logarithmic standard deviation ($\sigma\zeta$) of a particle size distribution of the particulate hydrogel is preferably 0.2 to 1.5, more preferably 0.2 to 1.3, and even more preferably 0.2 to 1.2. A logarithmic standard deviation ($\sigma\zeta$) of a particle size distribution indicates narrowness of the particle size distribution. A smaller value of the logarithmic standard deviation ($\sigma\zeta$) of the particle size distribution correlates to a more uniform particle diameter and offers the advantage of enabling uniform drying. However, a logarithmic standard deviation ($\sigma\zeta$) of a particle size distribution which is less than 0.2 requires a special operation such as particle size control during polymerization before gel-crushing or classification of the particulate hydrogel after gel-crushing. As such, a logarithmic standard deviation ($\sigma\zeta$) of a particle size distribution which is less than 0.2 is substantially difficult to employ from the viewpoint of productivity and cost.

Note that, in order to increase the later-described specific surface area of a water-absorbing resin, the gel-crushing method disclosed in the pamphlet of International Publication No. WO 2011/126079 is preferably used. Further, the gel-crushing method may be used in combination with the above-described foaming polymerization.

Further, to perform drying uniformly and efficiently, the particulate hydrogel has a moisture content of preferably 30 mass % or more, more preferably 45 mass % or more, preferably 70 mass % or less, and more preferably 55 mass % or less.

[3-1-4-4] Drying Step

This step is a step of drying a crushed hydrogel. Specifically, this step is a step of drying the particulate hydrogel (or, when a granulated gel is added, both the granulated gel and the particulate hydrogel) until a desired solid content is attained, so that a dried polymer is obtained. The solid content, i.e. a value obtained by subtracting a moisture content from 100 mass % of the gel, is preferably 80 mass % or more, more preferably 85 mass % or more, even more preferably 90 mass % or more, particularly preferably 92 mass % or more, preferably 99 mass % or less, even more preferably 98 mass % or less, and particularly preferably 97 mass % or less. Setting the solid content of the dried polymer to fall within any of the above ranges makes it possible to efficiently carry out pulverization, classification, and surface-crosslinking. Note that in the present specification, the phrase "drying is completed" means a state in which the solid content reaches 80 mass %. In this step, the dried polymer is in the form of a block, and the moisture content of the dried polymer can vary depending on which portion in the block of the following portions: an upper portion thereof, a lower portion thereof, a central portion thereof, and an end portion thereof the dried polymer is located in. In this case, dried polymers may be obtained appropriately from various positions of the block and crushed if necessary, and after that, moisture contents of the dried polymers may be measured and averaged.

In the present specification, a dried polymer with a solid content falling below the predetermined solid content can be referred to as an undried material. There may be a case where a "material to be dried" or a "particulate hydrogel" in the drying step includes both a particulate hydrogel and a granulated gel. Further, the drying step in Embodiment 1 of the present invention is a more effective condition particularly in a case where both the particulate hydrogel and the granulated gel are included in the drying step. Note that, in the other steps as well, there may be a case where a hydrogel and a treated material of the hydrogel include a granulated gel and a treated material of the granulated gel.

Examples of a drying method in the drying step include thermal drying, hot air drying, drying under reduced pressure, fluidized bed drying, infrared drying, microwave drying, drying by azeotropic dehydration with a hydrophobic organic solvent, high humidity drying by use of high temperature water vapor, and stirring drying. Of these drying methods, stirring drying and hot air drying are preferable from the viewpoint of drying efficiency. Stirring drying is preferably carried out by use of a stirring dryer such a paddle dryer or a rotatable drum type dryer. Further, hot air drying is preferably carried out by use of a through-flow batch-type dryer or a through-flow band-type dryer that carries out hot air drying on a through-flow belt. With use of the through-flow band-type dryer, efficient drying can be carried out while preventing, for example, the generation of fine powder due to physical breakage and friction of a dried polymer and a material to be dried of, for example, a particulate hydrogel in the process of being dried.

A drying temperature, i.e. a temperature of hot air, in an embodiment of the present invention is preferably 120° C. or more, more preferably 130° C. or more, even more preferably 150° C. or more, preferably 250° C. or less, more preferably 230° C. or less, and even more preferably 200° C. or less, in consideration of drying efficiency. Further, a drying time is preferably 10 minutes to 120 minutes, more preferably 20 minutes to 90 minutes, and even more preferably 30 minutes to 60 minutes. Setting the drying temperature and the drying time to be within these ranges makes it possible to obtain a water-absorbing resin whose physical properties are within a desired range. Note that other drying conditions can be set as appropriate in accordance with a moisture content of a particulate hydrogel to be dried and a granulated gel to be dried, total mass thereof, and a desired solid content. In the case of band drying, various conditions disclosed in, for example, the pamphlet of International Publication No. WO 2006/100300, the pamphlet of International Publication No. WO 2011/025012, the pamphlet of International Publication No. WO 2011/025013, and the pamphlet of International Publication No. WO 2011/111657 can be applied as necessary.

[3-1-4-5] Pulverizing Step and Classification Step

A pulverizing step is a step of pulverizing a polymer obtained after drying, and a classification step is a step of removing fine powder from a pulverized polymer. Specifically, this step is a step of pulverizing the dried polymer obtained through the drying step in the pulverizing step and adjusting the particle size of the pulverized polymer to a particle size within a desired range in the classification step so as to obtain a crosslinked polymer. Undergoing the pulverizing step after drying makes it possible to obtain a particulate crosslinked polymer (hereinafter also referred to merely as "crosslinked polymer").

Examples of a pulverizer which can be used in the pulverizing step include: a high-speed rotation pulverizer such as a roll mill, a hammer mill, a screw mill, or a pin mill; a vibration mill; a knuckle-type pulverizer; and a cylindrical mixer. Out of these examples, a roll mill is preferable from the viewpoint of efficiency of pulverization. It is also possible to employ a combination of a plurality of these pulverizers.

Examples of methods for adjusting the particle size in the classification step include sieve classification with use of a JIS standard sieve (JIS Z8801-1 (2000)), airflow classification, and the like. Out of these examples, sieve classification is preferable from the viewpoint of classification efficiency. Note that, from the viewpoint of ease of pulverization, the classification step may be additionally carried out before the pulverizing step.

The crosslinked polymer has a particle size distribution such that the mass average particle diameter (D50) is preferably 300 μm or more and 600 μm or less, and the proportion of particles having a particle diameter of less than 150 μm is 5 mass % or less. The mass average particle diameter (D50) has an upper limit that is more preferably 500 μm or less, even more preferably 450 μm or less, and particularly preferably 400 μm or less. Further, the proportion of the particles having a particle diameter of less than 150 μm is more preferably 4 mass % or less, even more preferably 3 mass % or less, and particularly preferably 2 mass % or less. Further, a logarithmic standard deviation ($\sigma\zeta$) of the particle size distribution is preferably 0.20 or more, more preferably 0.25 or more, even more preferably 0.27 or more, preferably 0.50 or less, more preferably 0.45 or less, and even more preferably 0.43 or less, particularly preferably 0.40 or less, and most preferably 0.35 or less. The logarithmic standard deviation ($\sigma\zeta$) of the particle size distribution indicates narrowness of the particle size distribution. A smaller value of the logarithmic standard deviation ($\sigma\zeta$) of the particle size distribution correlates to a more uniform particle diameter and offers the advantage of less particle segregation. Preferably, the mass average particle diameter (D50) and the proportion of the particles having a particle diameter of less than 150 μm are satisfied. More preferably, the mass average particle diameter (D50), the proportion of the particles having a particle diameter of less than 150 μm, and the logarithmic standard deviation are satisfied and can be combined as appropriate so as to be within the above-described ranges.

Note that the mass average particle diameter (D50) and the logarithmic mean standard deviation ($\sigma\zeta$) can be measured by a measurement method disclosed in "(3) Mass-Average Particle Diameter (D50) and Logarithmic Standard Deviation ($\sigma\zeta$) of Particle Diameter Distribution" of U.S. Pat. No. 7,638,570.

The above-described particle size is also applied to a base water-absorbing resin obtained after the pulverizing step and the classification step. Therefore, in a case where surface crosslinking is carried out, it is preferable to subject the water-absorbing resin to surface-crosslinking treatment in the surface-crosslinking step so that the particle size falling within the above-described range which has been adjusted for the crosslinked polymer is maintained, and it is more preferable to carry out particle size adjustment by carrying out a sizing step subsequent to the surface-crosslinking step. Thus, the water-absorbing resin according to an embodiment of the present invention is preferably configured such that the mass average particle diameter (D50) and the proportion of the particles having a particle diameter of less than 150 μm are satisfied so as to be within the above-described ranges. The water-absorbing resin according to an embodiment of the present invention is more preferably configured such that the mass average particle diameter (D50), the proportion of the particles having a particle diameter of less than 150 μm, and the logarithmic standard deviation ($\sigma\zeta$) of the particle size distribution are satisfied so as to be within the above-described ranges. The water-absorbing resin according to an embodiment of the present invention is even more preferably configured such that the water-absorbing resin has a mass average particle diameter (D50) of 300 μm to 600 μm, the proportion of particles having a particle diameter of less than 150 μm in the water-absorbing resin is 5 mass % or less, and the water-absorbing resin has a logarithmic standard deviation ($\sigma\zeta$) of a particle size distribution of 0.20 to 0.50.

[3-1-4-6] Surface-Crosslinking Step

This step is a step of providing, in a surface layer of a crosslinked polymer obtained through the above-described steps, a portion with a higher crosslinking density as necessary. The surface-crosslinking step includes, for example, a mixing step, a heat treatment step, and a cooling step. The surface-crosslinking step involves, for example, radical crosslinking on the surface of the crosslinked polymer, surface polymerization on the surface of the crosslinked polymer, and a crosslinking reaction with a surface-crosslinking agent so as to produce a base water-absorbing resin.

A peak temperature (powder temperature) of the crosslinked polymer during the surface-crosslinking step, that is, a peak temperature (powder temperature) of the crosslinked polymer during the heat treatment step is preferably 180° C. or more, and more preferably 190° C. or more.

[3-1-4-6-1] Mixing Step

This step is a step of mixing, in a mixing apparatus, a solution containing a surface-crosslinking agent (hereinafter referred to as a "surface-crosslinking agent solution") with the crosslinked polymer, so that a base water-absorbing resin is obtained.

(Surface-Crosslinking Agent)

In Embodiment 1 of the present invention, a surface-crosslinking agent is used at the time of surface crosslinking. The surface-crosslinking agent is as has been described in [Polyacrylic acid (salt)-based water-absorbing resin] (described earlier).

An amount of the surface-crosslinking agent used or a total amount in a case where more than one surface-crosslinking agent is used is preferably 0.01 parts by mass to 10.00 parts by mass, more preferably 0.01 parts by mass to 5.00 parts by mass, and even more preferably 0.01 parts by mass to 2.00 parts by mass, relative to 100 parts by mass of the crosslinked polymer. Setting the amount of surface-crosslinking agent used to be within any of the above ranges makes it possible to form an optimal crosslinked structure in the surface layer of the crosslinked polymer and thus makes it possible to obtain a water-absorbing resin with excellent physical properties.

The surface-crosslinking agent is preferably added in the form of an aqueous solution to the crosslinked polymer. In such a case, an amount of water used is preferably 0.1 parts by mass to 20.0 parts by mass, more preferably 0.3 parts by mass to 15.0 parts by mass, and even more preferably 0.5 parts by mass to 10 parts by mass, relative to 100 parts by mass of the crosslinked polymer. Setting the amount of water used to be within any of the above ranges improves the handleability of the surface-crosslinking agent solution and makes it possible to uniformly mix the surface-crosslinking agent with the crosslinked polymer.

Alternatively, the surface-crosslinking agent solution may contain, as necessary, a hydrophilic organic solvent in combination with the water. In such a case, an amount of the hydrophilic organic solvent used is preferably 5 parts by mass or less, more preferably 3 parts by mass or less, and even more preferably 1 part by mass or less, relative to 100 parts by mass of the crosslinked polymer. Specific examples of the hydrophilic organic solvent include: lower alcohols such as methyl alcohol; ketones such as acetone; ethers such as dioxane; amides such as N,N-dimethylformamide; sulfoxides such as dimethyl sulfoxide; and polyhydric alcohols such as ethylene glycol. However, the amount of these hydrophilic organic solvents used is preferably limited to a minimum amount.

Further, various additives to be added in "[3-1-4-7] Additives and step of adding additives" below can be each added to the surface-crosslinking agent solution in an amount in a range of 5 parts by mass or less. Alternatively, the additives can be added in the mixing step, separately from the surface-crosslinking agent solution.

(Method for Mixing and Conditions of Mixing)

A method for mixing the crosslinked polymer with the surface-crosslinking agent solution can be a method in which a surface-crosslinking agent solution is prepared in advance, and the surface-crosslinking agent solution is mixed with the crosslinked polymer preferably by spraying or dropping the surface-crosslinking agent solution onto the crosslinked polymer, more preferably by spraying the surface-crosslinking agent solution onto the crosslinked polymer.

A mixing apparatus for carrying out the mixing preferably has torque necessary to evenly and reliably mix the crosslinked polymer with the surface-crosslinking agent. The mixing apparatus is preferably a high-speed stirring mixer and more preferably a high-speed stirring continuous mixer. The high-speed stirring mixer has a rotation speed which is preferably 100 rpm or more, more preferably 300 rpm or more, preferably 10000 rpm or less, and more preferably 2000 rpm or less.

The crosslinked polymer supplied in this step has a temperature which is preferably 35° C. to 80° C., more preferably 35° C. to 70° C., and even more preferably 35° C. to 60° C., from the viewpoints of mixability with the surface-crosslinking agent solution and aggregability of the humidified mixture. Further, a mixing time is preferably 1 second or more, more preferably 5 seconds or more, preferably 1 hour or less, and more preferably 10 minutes or less.

[3-1-4-6-2] Heat Treatment Step

This step is a step of heating the base water-absorbing resin, which has been obtained in the mixing step, so as to cause a crosslinking reaction on a surface of the crosslinked polymer. The heat treatment of the base water-absorbing resin may involve heating the base water-absorbing resin in a still state or heating the base water-absorbing resin in a fluid state with use of motive power such as that of stirring or the like. However, it is preferable to heat the base water-absorbing resin while the base water-absorbing resin is stirred because such a method makes it possible to heat the entirety of the humidified mixture uniformly. From the above viewpoint, examples of a heat treatment apparatus for carrying out the heat treatment include a paddle dryer, a multi-fin processer, and a tower dryer.

A heating temperature in this step is preferably 150° C. to 250° C., more preferably 170° C. to 250° C., even more preferably 170° C. to 230° C., and still more preferably 180° C. to 230° C., from such viewpoints as type and amount of surface-crosslinking agent, and water absorption performance of the water-absorbing resin. A heating time is preferably at least 5 minutes and more preferably at least 7 minutes. Controlling the heating temperature and the heating time to be within the above ranges is preferable because doing so improves the water absorption performance of the water-absorbing resin to be obtained.

[3-1-4-6-3] Cooling Step

This step is an optional step which is provided after the heat treatment step and/or the drying step if needed. This step involves force-cooling the water-absorbing resin from its high temperature after the heat treatment step to a predetermined temperature and causing the surface-crosslinking reaction to finish quickly.

The cooling of the water-absorbing resin may involve cooling the water-absorbing resin in a still state or cooling the water-absorbing resin in a fluid state with use of motive power such as that of stirring or the like. However, it is preferable to cool the water-absorbing resin while the water-absorbing resin is stirred because such a method makes it possible to cool the entirety of the water-absorbing resin uniformly. From the above viewpoint, examples of a cooling apparatus for carrying out the cooling include a paddle dryer, a multi-fin processer, and a tower dryer. These cooling apparatuses can have similar specifications to the heat treatment apparatus used in the heat treatment step. This is because a heat treatment apparatus can be used as a cooling apparatus by changing a heating medium to a cooling medium.

A cooling temperature in this step may be set as appropriate in accordance with, for example, the heating temperature in the heat treatment step and the water absorption performance of the water-absorbing resin. The cooling temperature is preferably 40° C. to 100° C., more preferably 50° C. to 90° C., and even more preferably 50° C. to 70° C.

[3-1-4-7] Additive and Step of Adding Additive

[3-1-4-7-1] Surface-Modifying Agent

A surface-modifying agent is an additive that is added for the purpose of modifying the surface of particles of the water-absorbing resin. Specific examples include a liquid permeability improving agent, an anti-caking agent for a case where moisture has been absorbed, an agent for controlling powder fluidity, and a binder for the water-absorbing resin. Particularly, from the viewpoint of improving liquid permeability, at least one compound selected from the group consisting of a polyvalent metal salt, a cationic polymer, and inorganic fine particles can be used. If necessary, two or more compounds selected from the group can be used in combination. The amount of the surface-modifying agent added is set as appropriate in accordance with the compound(s) selected. For the purpose of modifying the surface of particles of the water-absorbing resin, a step of adding the surface-modifying agent is carried out preferably subsequent to the polymerization step, more preferably subsequent to the drying step, and even more preferably subsequent to the surface-crosslinking step. Further, the surface-modifying agent can be added in one or more steps.

(Polyvalent Metal Salt)

In a case where the polyvalent metal salt is used, a polyvalent metal cation of the polyvalent metal salt has a valence of preferably two or more, more preferably two or more, preferably four or less, and even more preferably three or four. Examples of polyvalent metals which can be used include aluminum and zirconium. As such, examples of polyvalent metal salts which can be used in this step include aluminum lactate, zirconium lactate, aluminum sulfate, and zirconium sulfate. Out of these examples, from the viewpoint of the effect of improving saline flow conductivity (SFC), the polyvalent metal salt is more preferably aluminum lactate or aluminum sulfate and even more preferably aluminum sulfate.

The amount of the polyvalent metal salt added is preferably 0 mol or more, preferably less than $5.0 \times 10^{-5}$ mol, more preferably less than $4.0 \times 10^{-5}$ mol, and even more preferably less than $3.0 \times 10^{-5}$ mol, relative to 1 g of the water-absorbing resin.

Further, a solution containing the polyvalent metal may further contain, as an agent for adjusting permeability of the polyvalent metal into the water-absorbing resin, a monovalent metal compound, such as sodium hydroxide, sodium carbonate, sodium hydrogen carbonate, sodium acetate, and sodium lactate.

(Cationic Polymer)

In a case where the cationic polymer is to be used, examples of the cationic polymer include the substances disclosed in U.S. Pat. No. 7,098,284. Out of these examples, a vinyl amine polymer is more preferable from the viewpoint of improving the liquid permeability. The cationic polymer has a mass average molecular weight of preferably 5000 to 1000000.

The cationic polymer can be added in an amount such that an amount of the cationic polymer is preferably 0 part by mass or more, preferably less than 5.0 parts by mass, more preferably less than 4.0 parts by mass, and even more preferably less than 3.0 parts by mass, relative to 100 parts by mass of the water-absorbing resin.

(Inorganic Fine Particles)

In a case where inorganic fine particles are to be used, examples of the inorganic fine particles include the substances disclosed in U.S. Pat. No. 7,638,570. Out of these examples, silicon dioxide is preferable from the viewpoint of improving the liquid permeability.

The inorganic fine particles have a primary particle diameter of preferably less than 100 nm, more preferably less than 80 nm, and even more preferably less than 50 nm. The inorganic fine particles may be in powder form or in the form of a solution in a suspended state. The inorganic fine particles can be added in an amount such that an amount of the inorganic fine particles is preferably 0 part by mass or more, preferably 5.0 parts by mass or more, more preferably less than 4.0 parts by mass, and even more preferably less than 3.0 parts by mass, relative to 100 parts by mass of the water-absorbing resin. An amount of the inorganic fine particles that are added, to the water-absorbing resin, in the form of a solution in a suspended state is calculated on the basis of a solid content of the inorganic fine particles in the solution in a suspended state.

[3-1-4-7-2] Another Additive

Examples of another additive include a chelating agent, a hydroxycarboxylic acid compound, a compound having a phosphorus atom, an oxidizer, an organic powder such as a metal soap, a deodorizing agent, an antibacterial agent, pulp, thermoplastic fibers, and aromatic substances such as terpene-based aromatic compounds and phenol-based aromatic compounds. One of these substances or two or more thereof can be used as the another additive. The another additive is preferably a chelating agent, and more preferably an amino polyvalent carboxylic acid or an amino polyvalent phosphoric acid. Specific examples of the another additive include chelating agents disclosed in, for example, Japanese Patent Application Publication Tokukaihei No. 11-060975, the pamphlet of International Publication No. WO 2007/004529, the pamphlet of International Publication No. WO 2011/126079, the pamphlet of International Publication No. WO 2012/023433, Published Japanese Translation of PCT International Application Tokuhyo No. 2009-509722, Japanese Patent Application Publication Tokukai No. 2005-097519, Japanese Patent Application Publication Tokukai No. 2011-074401, Japanese Patent Application Publication Tokukai No. 2013-076073, Japanese Patent Application Publication Tokukai No. 2013-213083, Japanese Patent Application Publication Tokukaisho No. 59-105448, Japanese Patent Application Publication Tokukaisho No. 60-158861, Japanese Patent Application Publication Tokukaihei No. 11-241030, and Japanese Patent Application Publication Tokukaihei No. 2-41155.

The amount of the another additive (preferably a chelating agent) added or contained is in a range of preferably 0.001 mass % to 1.000 mass % relative to a monomer or the water-absorbing resin.

The additive(s) can be added before, after, or during at least one step selected from among the aforementioned steps, i.e. the step of preparing an aqueous monomer solution, the polymerization step, the gel-crushing step, the drying step, the pulverizing step, the classification step, and the surface-crosslinking step. Preferably, the additive(s) is/are added before, after, or during any of the steps subsequent to the polymerization step.

[3-1-4-7-3] Step of Adding Additive

In a case where the additive(s) is/are each a liquid or a solution of an aqueous medium such as water, the addition of the additive(s) to the water-absorbing resin is carried out preferably by spraying the liquid or the solution onto the water-absorbing resin and evenly and reliably mixing the water-absorbing resin and the additive(s) by the application of sufficient torque. In a case where the additive(s) is/are each a solid in a powdery state or the like state, the additive(s) may be dry blended with the water-absorbing resin, and a water-based liquid such as water may be used as a binder.

Specific examples of an apparatus for use in the mixing include a stirring mixer, a cylindrical mixer, a double-wall conical mixer, a V-shaped mixer, a ribbon mixer, a screw mixer, a flow and rotary disk mixer, an airflow mixer, a twin-arm kneader, an internal mixer, a pulverizing kneader, a rotating mixer, and a screw extruder. In a case where a stirring mixer is to be used, a rotation speed of the stirring mixer is preferably 5 rpm or more, more preferably 10 rpm or more, preferably 10000 rpm or less, and more preferably 2000 rpm or less.

[3-1-4-8] Sizing Step

In an embodiment of the present invention, it is possible to carry out a sizing step as necessary, in addition to the above-described steps. The sizing step is a step of adjusting a water-absorbing resin after surface-crosslinking obtained through the surface-crosslinking step to a particle size within a desired range after the water-absorbing resin is subjected to the water-based liquid adding step and the drying step following addition of the water-based liquid, so as to obtain a water-absorbing resin, i.e., a water-absorbing agent ready to be shipped as an end product. Note, however, that in a case where the pulverizing step and the classification step are absent before the surface-crosslinking step, the later-described operation carried out after the surface-crosslinking step is assumed to be the pulverizing step and the classification step. As a method for adjusting the particle size in the sizing step, an adjusting method similar to the method employed in the classification step can be employed. Furthermore, if the water-absorbing resin has aggregated in the surface-crosslinking step or the step of adding the surface-modifying agent, crushing, e.g. light pulverization, may be carried out. Further, the particle size distribution after the particle size adjustment can be adjusted as appropriate according to an intended use, and is preferably the same degree of particle size distribution as in the classification step. Therefore, for example, classification with use of a sieve or the like can be carried out so as to satisfy a desired mass average particle diameter (D50), a desired ratio of the mass average particle diameter (D50), a desired logarithmic standard deviation, and the like.

[3-1-4-9] Fine Powder Recycle Step

This step is a step of, before the completion of drying in the drying step, recycling fine powder that has been removed in the classification step. More specifically, this step is a step of recycling the fine powder obtained in the water-absorbing resin production process, for use in the production process, preferably for use in a step before the drying step, so as to produce a water-absorbing resin. The fine powder to be recycled is a fine powder removed preferably in the classification step and more preferably in the classification step, the sizing step, and the like step. Note that the water-absorbing resin production process in which the fine powder is recycled for use does not necessarily have to be exactly the same as the water-absorbing resin production process in which the fine powder has been obtained. The fine powder may be recycled for use in another water-absorbing resin production process which differs to an extent that does not impair the gist of Embodiment 1 of the present invention. For example, the fine powder generated in one production line may be recycled for use in an adjacent production line. Alternatively, after the fine powder has been removed in the same production line, the polymerization conditions and the like may be changed before the fine powder is recycled.

[3-1-4-9-1] Granulation Step

This step is a step of mixing the removed fine powder and a water-based liquid to obtain a granulated gel. The granulated gel is a gel such that a plurality of individual particles are gathered and aggregated or fused into a large particle form when observed through an optical microscope, and is preferably a gel that is of such strength as not to be damaged by a classification operation or a conveying operation.

(Fine Powder)

Target fine powder in Embodiment 1 of the present invention is all fine powder obtained in the production of the water-absorbing resin, but is preferably fine powder removed in the classification step, and more preferably fine powder removed in the classification step and the sizing step. The fine powder, with the water-based liquid added thereto, is granulated. A mixing ratio (mass ratio) between the fine powder removed in the classification step and the fine powder removed in the sizing step is preferably 99:1 to 50:50, more preferably 98:2 to 60:40, and even more preferably 95:5 to 70:30. The fine powder removed in the sizing step has undergone the surface-crosslinking step or, in some cases, has undergone not only the surface-crosslinking step but also the step of adding a surface-modifying agent which has been described in the above-described "Surface-modifying agent". Thus, the inclusion of such fine powder in a predetermined ratio in the granulation step is advantageous in that it decreases aggregability of the granulated gel. Further, in Embodiment 1 of the present invention, for example, fine powder removed by a bag filter or the like in each step of the production process may be used for granulation. Alternatively, fine powder obtained through the removal in the separate steps and fine powder obtained through the removal in another production process (with use of another production apparatus) may be used in combination. Further, the fine powder may have a composition which is the same as a composition of the hydrogel to be dried together or may have a composition which differs from the composition of the hydrogel to be dried together. However, it is preferable to use fine powder having a composition which is the same as a composition derived from the hydrogel to be dried together.

A size of the fine powder used for granulation is preferably smaller than a size of the end product of the water-absorbing resin. For example, the fine powder has the mass average particle diameter (D50) defined by JIS standard sieve classification of preferably 150 µm or less, and more preferably 106 µm or less. The fine powder has a lower limit of D50 of preferably 38 µm or more, and more preferably 45 µm or more. Although the fine powder is targeted in this step, even an agglomerate of a size exceeding the size of the end product can be pulverized as appropriate and used as fine powder for granulation. It is desirable that preferably the fine powder contain particles having a particle diameter defined by JIS standard sieve classification of less than 150 µm in an amount such that an amount of the particles is preferably 50 mass % to 100 mass %, more preferably 70 mass % to 100 mass %, and even more preferably 90 mass % to 100 mass %. Further, from the aspect of granulation strength, the shape of the fine powder is preferably a non-uniform shape obtained by aqueous solution polymerization rather than a spherical shape obtained by reversed phase suspension polymerization. Further, as described above, the fine powder may be fine powder removed after the surface-crosslinking step, which is generally carried out in the production of a water-absorbing resin, may be fine powder removed before the surface-crosslinking step, or may be a mixture thereof.

A water-based liquid is added to the fine powder, preferably a mixture in which the fine powder is mixed in a predetermined ratio, so that a granulated gel is obtained. The granulated gel uses fine powder having various particle diameters obtained from the above-described single step or a plurality of steps. In the granulation step, in a case where a huge gel-like material beyond the above-described range is obtained by mixing the fine powder and the water-based liquid, the huge gel-like material is preferably removed by a classification means such as a sieve. The huge gel-like material thus removed can be, if necessary, dried and pulverized so as to be reused.

A temperature of the fine powder when mixed with the water-based liquid is preferably 40° C. to 120° C., more preferably 50° C. to 100° C., and even more preferably 60° C. to 90° C. Increasing the temperature of the fine powder improves mixability of the fine powder and the water-based liquid and makes it easy to obtain a desired granulated gel. However, setting the temperature of the fine powder to be excessively high increases a heating cost. The temperature of the fine powder can be adjusted as appropriate, if necessary, by heating the fine powder from the outside with hot air or the like, by keeping warm the fine powder after heated in the drying step, or by cooling the fine powder through, for example, blowing of a room-temperature air. Preferably, the fine powder is heated or kept warm in a vessel that has a heating means such as a steam trace.

(Water-Based Liquid)

Specific examples of the water-based liquid used for mixing with fine powder include an aqueous solution and the like containing water; lower alcohols such as methyl alcohol, ethyl alcohol, n-propyl alcohol, isopropyl alcohol, n-butyl alcohol, isobutyl alcohol, and t-butyl alcohol; ketones such as acetone; ethers such as dioxane and tetrahydrofuran; amides such as N,N-dimethylformamide; sulfoxides such as dimethyl sulfoxide; and the like. From the aspect of physical properties and granulation strength, the water-based liquid has a water content of preferably 90 mass % to 100 mass %, and more preferably 99 mass % to 100 mass %. Particularly preferably, the water-based liquid is composed of water only. In addition, the water-based liquid can further contain a small amount of additive, such as a cross-linking agent, a chelating agent, a surfactant, a polymerization initiator, an oxidizer, a reducing agent, and a hydrophilic polymer, to such an extent that the effects of Embodiment 1 of the present invention are not impaired. As the additive, one kind of additive or two or more kinds of additives may be added. In a case where two or more kinds of additives are added, they may be different from each other or may be the same. For example, using a water-based liquid in which the polymerization initiator and/or the reducing agent described in the polymerization step is/are added makes it possible to reduce residual monomers of a granulated gel and a hydrogel. A preferable polymerization initiator is persulfate, and a preferable reducing agent is (bi)sulfurous acid (salt). For example, using a water-based liquid in which an oxidizer is added can, in some cases, reduce deterioration of physical properties, such as fluid retention capacity, when the granulated gel has been dried. The oxidizer is preferably at least one oxidizer selected from chlorite, hypochlorite, and peroxide, and more preferably hydrogen peroxide. For example, using a water-based liquid in which a surfactant is added makes it possible to cause the surfactant to be contained in the granulated gel and makes it possible to effectively prevent the agglomeration of granulated gels. Further, using a water-based liquid in which a crosslinking agent and/or a hydrophilic polymer is/are added makes it possible to increase agglomeration strength of the granulated gel and prevent remicronization in a subsequent step. The crosslinking agent is selected from the above-described internal crosslinking agent and surface-crosslinking agent, and the hydrophilic polymer is selected from the above-described hydrophilic polymer added to the aqueous monomer solution.

The surfactant is exemplified by anionic surfactants, nonionic surfactants, cationic surfactants, and amphoteric surfactants.

Note that, in a case where the fine powder contains the above-described additive such as a crosslinking agent, a chelating agent, a surfactant, a polymerization initiator, an oxidizer, and a reducing agent, it is not necessary to add the additive to the water-based liquid, or alternatively, only an additive shortage may be added to the water-based liquid. It is particularly preferable that the fine powder contain a chelating agent, a surfactant, an oxidizer, a reducing agent, and the like described in the Step of adding additive section.

In a case where the granulation is carried out by mixing the fine powder and the water-based liquid, a preheated water-based liquid is preferably used. Using a heated water-based liquid allows the fine powder to be uniformly granulated in a short time and improves productivity. A temperature of the water-based liquid is preferably 40° C. or more, more preferably 50° C. or more, even more preferably 60° C. or more, particularly preferably 70° C. or more, preferably a temperature that is equal to or lower than a boiling point of the water-based liquid, and more preferably 100° C. or less. Note that the boiling point of the water-based liquid can be adjusted, for example, by addition of a salt and/or a solvent and/or by use of a pressure such as pressurization or depressurization. As an alternative method, a water vapor and a water-based liquid at room temperature may be added at the same time so that the water-based liquid is brought substantially to any of the above temperatures.

The amount of water-based liquid added is preferably less than 100 parts by mass, more preferably 80 parts by mass or less, even more preferably 50 parts by mass or less, preferably 10 parts by mass or more, more preferably 15 parts by mass or more, and even more preferably 20 parts by mass or more, relative to 100 parts by mass of the fine powder (on an as-is basis). The amount of water-based liquid added of 100 parts by mass or less makes it possible to minimize a drying load. The amount of water-based liquid added of 10 parts by mass or more may lead to a sufficient granulation strength and may make a granulated material less susceptible to damage due to uniform mixing of the fine powder.

(Mixing Apparatus)

In Embodiment 1 of the present invention, a mixing apparatus used for mixing the water-based liquid and the fine powder is not particularly limited. For example, in the case of a container-fixed type mixer, a mechanical stirring type mixer is preferable. Specifically, the mechanical stirring type mixer is exemplified by a Turbulizer (manufactured by Hosokawa Micron Corporation), a Loedige mixer (manufactured by Gebruder Loedige Maschinenbau GmbH), and a mortar mixer (manufactured by Nishinihonshikenki). Further, either one of a batch type mixer and a continuous type mixer may be used for mixing.

In Embodiment 1 of the present invention, preferably, a heated water-based liquid and heated fine powder are mixed by the mixing apparatus. In Embodiment 1 of the present invention, in addition to the heating of the water-based liquid and the fine powder, it is more preferable that the inside of the mixing apparatus, specifically, a wall surface of the mixing apparatus and/or a stirring means such as a stirring blade, be heated. When the mixing was carried out in a state in which the inside of the mixing apparatus, the water-based liquid, and the fine powder are all heated to a predetermined temperature in this way, it is possible to, while preventing or reducing generation of the huge gel-like material, easily obtain a granulated gel having a desired particle diameter more efficiently. In Embodiment 1 of the present invention, such an effect can be obtained even if any of the fine powder, the water-based liquid, and the mixing apparatus is not heated. However, with preferably at least one of them, more preferably two of them, and even more preferably all of them being heated to a predetermined temperature, a more excellent effect is brought about.

A heating temperature of the inside of the mixing apparatus, preferably an inner wall surface of the mixing apparatus and/or the stirring means, during the mixing is preferably 50° C. to 120° C., more preferably 55° C. to 100° C., still more preferably 60° C. to 90° C., particularly preferably 65° C. to 90° C., most preferably 70° C. to 90° C. Heating the mixing apparatus, preferably any of the inner wall surface and the stirring means, more preferably both the inner wall surface and the stirring means, allows the fine powder to be uniformly granulated in a short time and improves productivity. The temperature of the inside of the mixing apparatus can be adjusted as appropriate, for example, by supply of a heated gas and/or by conduction of heat.

In Embodiment 1 of the present invention, mixing of the fine powder and the water-based liquid for the granulation is preferably high-speed mixing. Carrying out high-speed mixing prevents generation of a huge gel-like material. This eliminates the need for a huge amount of mixing force that is needed in a case where a huge gel-like material is generated, and makes it possible to circumvent a problem that a gel-like mass in a kneaded state causes, for example, breakage and entanglement of a main chain and results in deterioration of a water-absorbing resin.

The above-described high-speed mixing means that a time from a point in time when contact between the fine powder and the water-based liquid, which are raw materials, occurs in the mixing apparatus to the generation of a granulated gel is short. In other words, the high-speed mixing means that a time from when the raw materials are introduced into the mixing apparatus to when the granulated gel is taken out is short. A mixing time is preferably 3 minutes or less, more preferably 1 minute or less, preferably 1 second or more, and more preferably 5 seconds or more. The mixing time that is 5 seconds or more allows the water-based liquid and the fine powder to be uniformly mixed. This causes no fear of generation of a huge gel-like material into which the water-based liquid and the fine powder are integrated. Further, the mixing time that is 3 minutes or less causes no fear of performance deterioration of a resulting water-absorbing resin, such as an increase in water-soluble component of the water-absorbing resin and a decrease in fluid retention capacity under pressure of the water-absorbing resin.

Therefore, as a means for achieving the high-speed mixing, it is desirable to introduce the raw materials into the mixing apparatus in a short time. The longer a time of the introduction of one or both of the raw materials by, for example, gradual addition carried out by a method such as spraying of the water-based liquid, the longer the mixing time will become. This may cause the fine powder to become a large agglomerate or may deteriorate a water-absorbing resin due to prolonged kneading. The fine powder and the water-based liquid may be introduced into the mixing apparatus at the same time or at different timings that are timings such that one of the fine powder and the water-based liquid is introduced, and the other one thereof is then introduced. Therefore, a time from the start of the introduction of both of the raw materials when the raw materials are introduced at the same time or the material to be introduced later when the raw materials are introduced at different timings to the end of the introduction, is preferably 60 seconds or less, more preferably 30 seconds or less, and still more preferably 10 seconds or less.

To achieve higher speed mixing, a high-speed stirring paddle mixer is preferably used. At this time, a rotation speed of a paddle is preferably 100 rpm or more, more preferably 200 rpm or more, even more preferably 300 rpm or more, preferably 5000 rpm or less, more preferably 4000 rpm or less, and even more preferably 3000 rpm or less. A direction of a rotation shaft of the paddle is not limited, but may be a vertical direction or a horizontal direction.

[3-1-4-9-2] Granulated Gel Addition Step

This step is a step of adding a granulated gel to a hydrogel in at least one step of the steps, from the polymerization step to the drying step, carried out until drying is completed in the drying step and/or in between any steps of the steps, from the polymerization step to the drying step, carried out until drying is completed in the drying step. Specifically, it is preferable that the granulated gel be added to the hydrogel in at least one step selected from the group consisting of during the polymerization step, a step carried out after the polymerization step but before the gel-crushing step, during the gel-crushing step, a step carried out after the gel-crushing step but before the drying step, and during the drying step. Note that, since the hydrogel is obtained even during the polymerization step, the granulated gel may be added during the polymerization step. In the drying step, a polymer having a solid content of less than 80 mass % can generally be regarded as a hydrogel. That is, since the hydrogel exists until some midpoint in the drying step, the granulated gel may be added during the drying step. The granulated gel is added to the hydrogel preferably after the gel-crushing step but before the drying step or during the drying step and more preferably after the gel-crushing step but before the drying step. Thus, the addition of the granulated gel to the hydrogel after the crushing allows the granulated gel and the hydrogel to be easily mixed due to a small difference in particle size between the granulated gel and the hydrogel and is less likely to cause non-uniform dryness. Particularly, carrying out crushing at controlled gel-grinding energy allows the hydrogel to have a granulation shape and thus makes it possible to further prevent non-uniform dryness. In contrast, the addition of the granulated gel added before the gel-crushing step or during the gel-crushing step may impose a load on a gel-crusher and make gel-crushing unstable, so that it may be impossible to control a gel particle diameter. Note that "before . . . step" and "after . . . step" include all steps before a step concerned and after the step concerned.

In the granulated gel addition step, the granulated gel has a solid content of 50 mass % or more and 90 mass % or less.

(Solid Content)

In an embodiment of the present invention, it is further preferable that the solid content of the granulated gel and the solid content of the hydrogel be controlled appropriately in the step of re-adding the granulated gel to the hydrogel. That is, if the solid content of the granulated gel and the solid content of the hydrogel are too low, dryness becomes partially incomplete, and agglomerates are more likely to be generated. The solid content that is too high tends to cause an increase in amount of residual monomer. In an embodiment of the present invention, it is desirable that the solid content of the granulated gel and/or the solid content of the hydrogel be within an appropriate range(s). The solid content of the hydrogel is preferably 30 mass % to 70 mass %, more preferably 45 mass % to 55 mass %, and even more preferably 45 mass % to 50 mass %. The solid content of the granulated gel is preferably 50 mass % to 90 mass %, more preferably 55 mass % to 85 mass %, and even more preferably 60 mass % to 80 mass %. The solid content of the granulated gel during the re-addition step is preferably in any of the above-described ranges, the solid content of the granulated gel is preferably in any of the above-described ranges, and the temperature of the granulated gel and the hydrogel is even more preferably in any of the above-described ranges.

In Embodiment 1 of the present invention, a ratio between the granulated gel and the hydrogel may be determined as appropriate in accordance with the amount of fine powder separated and the setting of the solid content of the granulated gel. From the viewpoint of physical properties of a water-absorbing resin, the granulated gel is added in an amount such that an amount of the granulated gel is normally 10 parts by mass to 50 parts by mass, more preferably 15 parts by mass to 40 parts by mass, and even more preferably 20 parts by mass to 30 parts by mass, relative to 100 parts by mass of the hydrogel (on an as-is basis). According to a method of Embodiment 1 of the present invention, it is possible to prevent non-uniform dryness even when the proportion of the granulated gel is 10 parts by mass or more. Note that, if the proportion of the granulated gel is too high, final quality and physical properties of a water-absorbing resin as an end product are significantly affected by the recycled fine powder, that is, the granulated gel.

The hydrogel to which the granulated gel is added is treated in the drying step. Since various conditions and the like of a mixed gel are the same as those of the above-described drying step, the description thereof will be omitted. Further, a pulverizing step and a classification step carried out after the drying step are the same as the above-described pulverizing step and the above-described classification step, and the surface-crosslinking step, the sizing step, and the like are performed as necessary, so that a water-absorbing resin to be a product is obtained. Further, the fine powder obtained in the classification step and other step(s) may also be treated in the above-described recycle step.

[3-2] Embodiment 2

A method for producing a water-absorbing resin according to Embodiment 2 of the present invention includes the step of bringing the water-absorbing resin into contact with a supercritical solvent so as to remove impurities from the water-absorbing resin (in the present specification, the step of bringing the water-absorbing resin into contact with a supercritical solvent so as to remove impurities from the water-absorbing resin may be hereinafter referred to as an "impurity removing step"), the water-absorbing resin containing a polyacrylic acid (salt)-based resin as a main component, the water-absorbing resin being internally crosslinked, and the water-absorbing resin being surface-crosslinked.

Note that the impurities are not particularly limited and are preferably organic compounds having two or more carbon atoms. Examples of such organic compounds include unreacted products derived from a reactive raw material, such as the residual acrylic acid (salt) monomer and a residual crosslinked product, impurities contained in a raw material, and low-molecular-weight compounds such as a by-product derived from a raw material.

[3-2-1] Impurity Removing Step

In the impurity removing step, a method for bringing a base water-absorbing resin into contact with a supercritical solvent is not particularly limited provided that the method allows the base water-absorbing resin to be brought into contact with the supercritical solvent. Examples of the method include a method in which a base water-absorbing resin is contained, in an extraction tank, as a fixed bed or a fluidized bed so that the base water-absorbing resin is brought into contact with a supercritical solvent in the extraction tank. The base water-absorbing resin can be brought into contact with the supercritical solvent in a continuous mode or in a batch mode. Furthermore, in a case where a process for producing a water-absorbing resin is carried out in a continuous mode, the step of bringing the base water-absorbing resin into contact with the supercritical solvent may be continuously carried out by, for example, placing a plurality of extraction tanks in parallel with each other.

A compound to be used in the supercritical solvent is not particularly limited. In order to achieve smaller-scale energy consumption and a smaller-scale device, it is preferable to select a compound that reaches a supercritical state preferably at a temperature as low as possible and a pressure as low as possible. A temperature at which a compound to be selected reaches a supercritical state is preferably 150° C. or less, more preferably 120° C. or less, and even more preferably 100° C. or less. A pressure at which a compound to be selected reaches a supercritical state is preferably 100 MPa or less, more preferably 50 MPa or less, and even more preferably 30 MPa or less.

Examples of a substance to be used in the supercritical solvent that is selected in the above temperature range and the above pressure range include ethylene, carbon dioxide, ethane, nitrous oxide, propylene, chlorodifluoromethane, propane, dichlorodifluoromethane, and ammonia. Above all, the supercritical solvent is preferably supercritical carbon dioxide from the viewpoints of handleability and an easy condition for obtaining a supercritical state.

As an example of the method for bringing a base water-absorbing resin into contact with a supercritical solvent, the following description will discuss an impurity removing step that is carried out by using supercritical carbon dioxide as the supercritical solvent and using the supercritical extraction apparatus having a configuration illustrated in FIG. 1.

As illustrated in FIG. 1, the supercritical extraction apparatus includes a carbon dioxide cylinder 1, a pressure regulating valve 2, a high pressure liquid feed pump 3, a cooling device 4, a pressure-resistant extraction tank 5, a pressure reducing valve 6, and a flowmeter 7. Note that arrows in FIG. 1 indicate directions in which carbon dioxide gas and supercritical carbon dioxide flow.

First, a base water-absorbing resin is placed inside the pressure-resistant extraction tank 5 and set. Subsequently, carbon dioxide (carbon dioxide gas) in a gaseous state is released from the carbon dioxide cylinder 1 into the high pressure liquid feed pump 3. In so doing, the pressure regulating valve 2 and the cooling device 4 are used to regulate temperature and pressure of the carbon dioxide inside the high pressure liquid feed pump 3 so as to cause the carbon dioxide to be in a supercritical state. In this way, supercritical carbon dioxide is prepared inside the high pressure liquid feed pump 3. Thereafter, the high pressure liquid feed pump 3 is used to introduce the supercritical carbon dioxide into the pressure-resistant extraction tank 5 so as to bring the base water-absorbing resin into contact with the supercritical carbon dioxide. In so doing, temperature and pressure inside the pressure-resistant extraction tank 5 are controlled so that a supercritical state of carbon dioxide in the supercritical carbon dioxide is maintained. Thereafter, in the pressure-resistant extraction tank 5, the pressure reducing valve 6 is used to reduce pressure of the supercritical carbon dioxide, which has been brought into contact with the water-absorbing resin, so as to convert the supercritical carbon dioxide into a state of carbon dioxide gas and release the carbon dioxide gas from the pressure-resistant extraction tank 5 into outside air.

A supercritical solvent of an embodiment of the present invention means a substance that in a supercritical state exceeding a critical temperature and a critical pressure, has a density close to that of a liquid and a viscosity so low as that of gas and is in an intermediate state of liquid and gas. Note here that Table 1 shows temperatures and pressures at which typical compounds reach a supercritical state. Carbon dioxide that is particularly preferably used has a critical temperature of approximately 31° C. (31.1° C.) and a critical pressure of 7.4 MPa (7.38 MPa).

TABLE 1

| Compound | Critical temperature [° C.] | Critical pressure [Mpa] |
| --- | --- | --- |
| Ethylene | 9.2 | 5.03 |
| Carbon dioxide | 31.0 | 7.38 |
| Ethane | 32.2 | 4.88 |
| Nitrous oxide | 36.5 | 7.23 |
| Propylene | 91.8 | 4.62 |
| Chlorodifluoromethane (Freon-22) | 96.1 | 4.97 |
| Propane | 96.6 | 4.24 |
| Dichlorodifluoromethane (Freon-12) | 111.7 | 3.99 |
| Ammonia | 132.4 | 11.27 |

In an embodiment of the present invention, it is preferable to prepare a supercritical solvent by storing, in a state of gas, a compound constituting a supercritical solvent, and controlling temperature and pressure of the gas in ranges beyond a critical temperature and a critical pressure immediately before the impurity removing step, and to bring the supercritical solvent thus prepared into contact with a water-absorbing resin.

The supercritical solvent is in the above-described intermediate state of liquid and gas, and the compound constituting the supercritical solvent has small molecules. Thus, the supercritical solvent can enter fine gaps that are present inside the water-absorbing resin. The supercritical solvent has polarity similar to that of typical organic solvents such as hexane and toluene.

Here, it is known that for example, unreacted products derived from a reactive raw material, such as a residual monomer and a residual crosslinked product, which are the impurities contained in the base water-absorbing resin, impurities contained in a raw material, and by-products derived from a raw material commonly consist of low-molecular-weight organic compounds or contain a lot of low-molecular-weight organic compounds.

It is also known that the low-molecular-weight organic compounds have polarity similar to that of the typical organic solvents. That is, the low-molecular-weight organic compounds and the supercritical solvent have approximately the same polarity and thus have high affinity with each other.

Thus, in the impurity removing step of an embodiment of the present invention, a contact between the base water-absorbing resin and the supercritical solvent causes the supercritical solvent to enter fine gaps that are present inside the base water-absorbing resin. This makes it possible to extract, from the base water-absorbing resin, the low-molecular-weight organic compounds constituting the impurities that are present inside the base water-absorbing resin. As a result, in the impurity removing step of Embodiment 2 of the present invention, the impurities per se can be removed from the base water-absorbing resin.

The base water-absorbing resin is insoluble in the supercritical solvent. Thus, there is no fear that the base water-absorbing resin may deteriorate due to the supercritical solvent. Furthermore, in Embodiment 2 of the present invention, the supercritical solvent is volatilized in the form of gas from the base water-absorbing resin after the impurity removing step. Thus, no compound that constituted the supercritical solvent remains in the water-absorbing resin that has been treated. There is therefore no fear that a compound derived from the supercritical solvent and remaining in the water-absorbing resin that has been treated may cause a deterioration in physical properties of the water-absorbing resin, such as water absorption performance.

Thus, the impurity removing step of an embodiment of the present invention brings about an effect of while maintaining physical properties of a water-absorbing resin, such as water absorption performance, removing the impurities contained in the water-absorbing resin.

In the impurity removing step of an embodiment of the present invention, a contact time during which the base water-absorbing resin is to be brought into contact with the supercritical solvent is preferably 1 second to 1000 minutes, more preferably 1 minute to 900 minutes, and even more preferably 2 minutes to 800 minutes. By controlling the contact time in any of the above ranges, it is possible to suitably dissolve, in the supercritical solvent, impurities contained in the base water-absorbing resin, and consequently to suitably remove the impurities from the base water-absorbing resin.

In the impurity removing step of an embodiment of the present invention, the supercritical solvent to be brought into contact with the base water-absorbing resin has a volume of preferably 0.1 mL to 1000 L, more preferably 1 mL to 500 L, and even more preferably 10 mL to 250 L, per 1 g of the base water-absorbing resin. By controlling, in any of the above ranges, the volume of the supercritical solvent to be brought into contact with 1 g of the base water-absorbing resin, it is possible to suitably dissolve, in the supercritical solvent, impurities contained in the base water-absorbing resin, and consequently to suitably remove the impurities from the base water-absorbing resin. Note here that the expression "per 1 g of water-absorbing resin" means "per 1 g of water-absorbing resin to be introduced into an extraction tank".

In the impurity removing step of an embodiment of the present invention, while the base water-absorbing resin is brought into contact with the supercritical solvent, a compound constituting the supercritical solvent preferably maintains a supercritical state because the compound that maintains the supercritical state makes it possible to suitably remove the impurities from the base water-absorbing resin.

From the viewpoints described earlier, in the impurity removing step of an embodiment of the present invention, a temperature at which the supercritical solvent is to be brought into contact with the base water-absorbing resin is preferably 30° C. or more, more preferably 35° C. or more, and even more preferably 40° C. or more. In the impurity removing step of an embodiment of the present invention, a pressure at which the base water-absorbing resin is to be brought into contact with the supercritical solvent is preferably 4.2 MPa or more, more preferably 7.0 MPa or more, and even more preferably 10.0 MPa or more.

In the impurity removing step of an embodiment of the present invention, in a case where the base water-absorbing resin is brought into contact with the supercritical solvent at an excessively high temperature and an excessively high pressure, physical properties of the water-absorbing resin, such as water absorption performance may deteriorate by a change in structure of part of the water-absorbing resin and/or a change in internal structure of the water-absorbing resin. Furthermore, such a case, which results in application of industrially excessive energy and is uneconomic, is not preferable in cost terms.

From the viewpoint of avoiding a deterioration in physical properties of the water-absorbing resin and an increase in cost, in the impurity removing step of Embodiment 2 of the present invention, a temperature at which the base water-absorbing resin is to be in contact with the supercritical solvent is preferably 200° C. or less, and more preferably 150° C. or less. In the impurity removing step of Embodiment 2 of the present invention, a pressure at which the base water-absorbing resin is to be brought into contact with the supercritical solvent is preferably 200 MPa or less, and more preferably 150 MPa or less.

In consideration of impurities to be removed from a water-absorbing resin and affinity with the water-absorbing resin, polarity of the supercritical solvent may be changed by addition of water and/or an organic solvent. Examples of the organic solvent include a low-molecular-weight organic solvent, and ethanol, methanol, isopropyl alcohol, acetone, or the like is preferably selected. The water and/or an organic solvent, together with the supercritical solvent, may be supplied, as a single or mixed solution, in the impurity removing step. Alternatively, a water-absorbing resin to which a small amount of water has been added in advance so that the water-absorbing resin is made swollen may be brought into contact with a mixture of the supercritical solvent and the low-molecular-weight organic solvent in the impurity removing step.

[3-2-2] Physical Properties of Pretreatment Water-Absorbing Resin

In an embodiment of the present invention, a water-absorbing resin to be subjected to the impurity removing step (hereinafter also referred to as a "pretreatment water-absorbing resin") is not particularly limited provided that the water-absorbing resin contains a polyacrylic acid (salt)-based resin as a main component, is internally crosslinked, and is surface-crosslinked.

Note that a method for measuring physical properties of the pretreatment water-absorbing resin (described later) may also be applied to measurement of physical properties of a water-absorbing resin obtained by a "method for treating a water-absorbing resin" according to an embodiment of the present invention (hereinafter also referred to as a "posttreatment water-absorbing resin"), a water-absorbing resin produced by a "method for producing a water-absorbing resin" according to an embodiment of the present invention, and a "water-absorbing resin" according to an embodiment of the present invention.

In an embodiment of the present invention, the pretreatment water-absorbing resin is a water-absorbing resin that contains preferably 90 mass % or more, more preferably 93 mass % or more, and even more preferably 95 mass % or more of a particulate water-absorbing resin having a particle diameter of 45 μm or more and 850 μm or less.

In an embodiment of the present invention, by regulating, in the above range, the particle diameter of the particulate water-absorbing resin that accounts for 90 mass % or more of the pretreatment water-absorbing resin, during use of the posttreatment water-absorbing resin as a water-absorbing agent of a sanitary material such as a disposable diaper, it is possible to reduce discomfort (e.g., a sense of ruggedness) given to a wearer of the sanitary material due to such a large-particle-diameter water-absorbing resin having a large particle diameter. By regulating, in the above range, the particle diameter of the particulate water-absorbing resin that accounts for 90 mass % or more of the pretreatment water-absorbing resin, it is possible to prevent or reduce occurrence of a dust problem that is caused in a case where a small-particle-diameter water-absorbing resin having a small particle diameter and included in the particulate water-absorbing resin that accounts for 90 mass % or more of the pretreatment water-absorbing resin is scattered during handling of the water-absorbing resin in a sanitary material manufacturing plant. Furthermore, by regulating, in the above range, the particle diameter of the particulate water-absorbing resin that accounts for 90 mass % or more of the pretreatment water-absorbing resin, it is also possible to expect the size of a gap inside the pretreatment water-absorbing resin to be controlled to the size that makes it easy for the supercritical solvent to enter the gap. In a case where the size of the gap is controlled to the size that makes it easy for the supercritical solvent to enter the gap, it is considered that the impurities can be suitably removed by the supercritical solvent that has entered the gap.

The particle diameter of the particulate water-absorbing resin that accounts for 90 mass % or more of the pretreatment water-absorbing resin can be regulated in the above range by a publicly-known method for regulating a particle diameter of a water-absorbing resin.

A proportion of the particulate water-absorbing resin in which the pretreatment water-absorbing resin has a particle diameter of 45 μm or more and 850 μm or less can be measured by a measurement method disclosed in "(3) Mass-Average Particle Diameter (D50) and Logarithmic Standard Deviation (σζ) of Particle Diameter Distribution" of U.S. Pat. No. 7,638,570.

Specifically, 10.0 g of a water-absorbing resin is placed, at a room temperature (20° C. to 25° C.) and a humidity of 50 RH %, in a set of JIS standard sieves (THE IIDA TESTING SIEVE, diameter: 8 cm) serving as a saucer and having respective mesh sizes of 850 μm, 710 μm, 600 μm, 500 μm, 300 μm, 150 μm, and 45 μm, and a vibration classifier (IIDA SIEVE SHAKER, Type: ES-65, Ser. No. 0501) was used to carry out classification for 5 minutes. Thereafter, a mass of the water-absorbing resin remaining on each of the sieves is measured. By calculating, on the basis of the result of the measurement, a residual percentage R, which is a ratio of the mass of the water-absorbing resin remaining on each of the sieves to the mass (10.0 g) of the water-absorbing resin that has not been classified, it is possible to obtain the proportion of the particulate water-absorbing resin in which the pretreatment water-absorbing resin has a particle diameter of 45 μm or more and 850 μm or less.

The pretreatment water-absorbing resin of an embodiment of the present invention has an absorption capacity without load (CRC) of preferably 20 g/g or more, more preferably 22 g/g or more, and even more preferably 25 g/g or more. The CRC preferably has an upper limit that is as high as possible. However, from the viewpoint of balance with other physical properties, the upper limit of the CRC is preferably 50 g/g or less, more preferably 48 g/g or less, and even more preferably 45 g/g or less.

The pretreatment water-absorbing resin of an embodiment of the present invention has an absorption capacity under load (AAP) of preferably 5 g/g or more, more preferably 7 g/g or more, and even more preferably 10 g/g or more. The AAP preferably has an upper limit that is as high as possible. However, from the viewpoint of balance with other physical properties, the upper limit of the CRC is preferably 40 g/g or less, more preferably 38 g/g or less, and even more preferably 35 g/g or less.

The pretreatment water-absorbing resin of an embodiment of the present invention has a moisture content of preferably 20 mass % or less, more preferably 18 mass % or less, and even more preferably 15 mass % or less.

The pretreatment water-absorbing resin of an embodiment of the present invention has a water absorption speed, as measured by a Vortex method, of preferably 10 seconds or more, more preferably 15 seconds or more, and even more preferably 20 seconds or more. The water absorption speed preferably has an upper limit that is as high as possible. However, from the viewpoint of balance with other physical properties, the upper limit of the water absorption speed is preferably 100 seconds or less, more preferably 90 seconds or less, and even more preferably 80 seconds or less.

The pretreatment water-absorbing resin of an embodiment of the present invention has a saline flow conductivity (SFC) of preferably $1 \times 10^{-7}$ cm$^3$·sec/g or more, more preferably $2 \times 10^{-7}$ cm$^3$·sec/g or more, and even more preferably $5 \times 10^{-7}$ cm$^3$·sec/g or more. The SFC preferably has an upper limit that is as high as possible. However, from the viewpoint of balance with other physical properties, the upper limit of the CRC is preferably $200 \times 10^{-7}$ cm$^3$·sec/g or less, more preferably $150 \times 10^{-7}$ cm$^3$·sec/g or less, and even more preferably $100 \times 10^{-7}$ cm$^3$·sec/g or less.

The pretreatment water-absorbing resin of an embodiment of the present invention preferably has the aforementioned physical property values in the respective aforementioned ranges so that a water-absorbing resin that is obtainable by the method for treating a water-absorbing resin according to an embodiment of the present invention also has excellent physical properties.

[3-2-3] Method for Producing Pretreatment Water-Absorbing Resin

The pretreatment water-absorbing resin of an embodiment of the present invention can be produced by a known method. Examples of the method include a method similar to the method for producing a surface-crosslinked water-absorbing resin to be subjected to the water-based liquid adding step in the production method according to Embodiment 1. Furthermore, the method for producing a water-absorbing resin according to Embodiment 2 of the present invention can include the steps described in the production method Embodiment 1, but does not need to include all the steps.

[3-2-4] Physical Properties of Posttreatment Water-Absorbing Resin

After having been subjected to the impurity treatment step, the water-absorbing resin of an embodiment of the present invention contains impurities in an amount of preferably 2 mass % or less, more preferably 1 mass % or less, and even more preferably 0.5 mass % or less, relative to 100 mass % as a total mass of the water-absorbing resin.

In the impurity removing step carried out in a method for treating a base water-absorbing resin of an embodiment of the present invention, an amount of the impurities contained in the base water-absorbing resin is reduced by preferably 30 mass % or more, and more preferably 50 mass % or more assuming that an amount of the impurities that the base water-absorbing resin contains before being treated is 100 mass %.

The impurities can be ordinary impurities contained in an internally-crosslinked and surface-crosslinked water-absorbing resin. Examples of the impurities include unreacted products derived from a reactive raw material, such as a residual monomer and a residual cross-linking agent, impurities contained in a raw material, and by-products that are by-produced from a raw material. There is a case where some impurities or by-products are unknown substances and thus cannot be determined by various analysis methods. However, even in such a case, a change in peak intensity observed in, for example, a chromatograph can be used to identify the impurities or by-products.

[3-3] Embodiment 3

A method for producing a water-absorbing resin according to Embodiment 3 of the present invention is a method for producing a surface-crosslinked water-absorbing resin, including a step of successively including a polymerization step, a drying step of drying a hydrogel having been obtained in the polymerization step, and a surface-crosslinking step, and adding a volatile component reducing agent at or after an end of the polymerization step.

[3-3-1] Step of Adding Volatile Component Reducing Agent

The method for producing a water-absorbing resin according to Embodiment 3 of the present invention only needs to include, at or after the end of the polymerization step, a step of adding a volatile component reducing agent. Note, however, that the method more preferably includes, at or after the end of the drying step of drying a hydrogel having been obtained in the polymerization step, the step of adding a volatile component reducing agent, and even more preferably includes, at or after the end of the surface-crosslinking step, the step of adding a volatile component reducing agent.

The volatile component reducing agent is as has been described in [Polyacrylic acid (salt)-based water-absorbing resin] (described earlier). The volatile component reducing agent only needs to contain at least one selected from a reducing agent, a surfactant, and an inorganic acid (salt). Note, however, that the volatile component reducing agent preferably contains a reducing agent, more preferably contains an amino group-containing reducing agent, and more preferably contains an amino acid (hydrochloride), an aminooxy compound (hydrochloride), an aminooxyacetic acid (hydrochloride), and a functional group-containing compound represented by the structural formula (1) (hydrochloride), and a hydrazide group-containing compound. An amino acid (hydrochloride), an aminooxy compound (hydrochloride), an aminooxyacetic acid (hydrochloride), and a compound containing a functional group represented by the structural formula (1) are particularly preferable.

In a case where the volatile component reducing agent is added to the water-absorbing resin, a method for adding the volatile component reducing agent is not particularly limited. For example, the volatile component reducing agent can be prepared in the form of an aqueous solution in which the volatile component reducing agent is dissolved in an aqueous medium such as water, or a dispersion in which the volatile component reducing agent is suspended in the aqueous medium, and the solution or dispersion can be added to the water-absorbing resin so as to be mixed with the water-absorbing resin. Alternatively, in a case where the volatile component reducing agent is a solid in a powdery state or the like state, the volatile component reducing agent may be dry blended with the water-absorbing resin, and a water-based liquid such as water may be used as a binder. Above all, the volatile component reducing agent is more preferably added in the form of an aqueous solution to the water-absorbing resin.

Specific examples of an apparatus for use in the mixing include a stirring mixer, a cylindrical mixer, a double-wall conical mixer, a V-shaped mixer, a ribbon mixer, a screw mixer, a flow and rotary disk mixer, an airflow mixer, a twin-arm kneader, an internal mixer, a pulverizing kneader, a rotating mixer, and a screw extruder. In a case where a stirring mixer is to be used, a rotation speed of the stirring mixer is not particularly limited but preferably 5 rpm or more, more preferably 10 rpm or more, even more preferably 10000 rpm or less, and still more preferably 2000 rpm or less.

The volatile component reducing agent only needs to contain at least one selected from a reducing agent, a surfactant, and an inorganic acid (salt). The reducing agent is added to the water-absorbing resin so as to be contained in a predetermined amount relative to a total amount of the water-absorbing resin containing, for example, an additive. The surfactant is also added to the water-absorbing resin so as to be contained in a predetermined amount relative to a total amount of the water-absorbing resin containing, for example, an additive. The inorganic acid (salt) is also added to the water-absorbing resin so as to be contained in a predetermined amount relative to a total amount of the water-absorbing resin containing, for example, an additive. Respective predetermined contained amounts of the reducing agent, the surfactant, and the inorganic acid (salt) are similar to the contained amounts described in "Reducing agent", "Surfactant", and "Inorganic acid (salt)" each described earlier.

In an embodiment of the present invention, in a case where the volatile component reducing agent is prepared in the form of an aqueous medium solution or dispersion, and the solution or dispersion is added to the water-absorbing resin, or a water-based liquid such as water is used as a binder, addition of the solution or dispersion and the water-based liquid as the binder, and drying of the water-absorbing resin to which the water-based liquid has been added are preferably carried out as in the case of the "water-based liquid adding step" described in Embodiment 1 (described earlier) (described in the section [3-1-1], the step of adding a water-based liquid to a surface-crosslinked water-absorbing resin) and the drying step "following addition of the water-based liquid" (described in the section [3-1-2], the step of drying the water-absorbing resin to which the water-based liquid has been added). More specific examples of a method according to an embodiment of the present invention of addition of the solution or dispersion and the water-based liquid as the binder, and drying of the water-absorbing resin to which the water-based liquid has been added include a method in which in the "water-based liquid adding step" (described in the section [3-1-1]) described in Embodiment 1, preferably an aqueous solution containing a volatile component reducing agent as a water-based liquid, and more preferably an aqueous solution containing an amino group-containing reducing agent is added, and the water-absorbing resin is dried in the drying step "following addition of the water-based liquid" (described in the section [3-1-2]) described in Embodiment 1. A more preferable embodiment is such that in a case where an aqueous solution containing an amino group-containing reducing agent is added, in a droplet state, to a surface-crosslinked water-absorbing resin having a specific surface area of 25 $m^2$/kg or more so that the surface-crosslinked water-absorbing resin has a moisture content of 27.5% or more, the surface-crosslinked water-absorbing resin is dried so as to have a moisture content of 20 mass % or less within one hour.

Furthermore, in a case where the volatile component reducing agent is added at or after the end of the surface-crosslinking step, physical properties of the surface-crosslinked water-absorbing resin to be subjected to a step of the addition are preferably similar to physical properties described in the "surface-crosslinked water-absorbing resin" described in Embodiment 1.

[3-3-2] Method for Producing Pretreatment Water-Absorbing Resin

A water-absorbing resin to be subjected to a step of an embodiment of the present invention of adding a volatile component reducing agent can be produced by a known method.

In a case where a production method according to an embodiment of the present invention includes, at or after the end of the polymerization step of polymerizing an acrylic acid (salt)-based monomer-containing monomer composition so as to obtain a crosslinked hydrogel polymer (polymerization step), the step of adding a volatile component reducing agent, examples of a method for producing a pretreatment water-absorbing resin include a production method including at least the polymerization step included in the production method according to Embodiment 1.

In a case where the production method according to an embodiment of the present invention includes, at or after the end of the drying step of drying a hydrogel having been obtained in the polymerization step, the step of adding a volatile component reducing agent, examples of a method for producing a pretreatment water-absorbing resin include a production method including at least the polymerization step and the drying step of drying a hydrogel having been obtained in the polymerization step, the polymerization step and the drying step each included in the production method according to Embodiment 1.

In a case where the production method according to an embodiment of the present invention includes, at or after the end of the surface-crosslinking step, the step of adding a volatile component reducing agent, examples of a method for producing a pretreatment water-absorbing resin include a production method including at least the polymerization step, the drying step of drying a hydrogel having been obtained in the polymerization step, and the surface-crosslinking step, the polymerization step, the drying step, and the surface-crosslinking step each included in the production method according to Embodiment 1.

The method for producing a water-absorbing resin according to Embodiment 3 of the present invention only needs to further include a step of successively including a polymerization step, a drying step of drying a hydrogel having been obtained in the polymerization step, and a surface-crosslinking step, and adding a volatile component reducing agent (preferably an amino group-containing reducing agent), and can further include the steps described in the production method according to Embodiment 1, but does not need to include all the steps.

Examples of the production method according to an embodiment of the present invention include a production method including the step of adding a water-based liquid to a surface-crosslinked water-absorbing resin (described in the section [3-1-1], water-based liquid adding step), the step of drying the water-absorbing resin to which the water-based liquid has been added (described in the section [3-1-2], drying step following addition of the water-based liquid), and further including a step of adding, instead of a water-based liquid used in the water-based liquid adding step, an aqueous solution containing a volatile component reducing agent (in particular, an amino group-containing reducing agent).

According to a conventional technique, in a case where a sanitary product (absorbent article) containing a water-absorbing resin is used, mixing of an odor caused by a substance volatilized from a surface-crosslinked water-absorbing resin (surface-crosslinked water-absorbing resin-derived volatile component) with an odor (urinous odor) from urine absorbed by the water-absorbing resin produces an unpleasant odor. Thus, an absorbent article that produces such an unpleasant odor is sometimes disliked by a user of the absorbent article. Since Embodiment 3 prevents or reduces an odor caused by a surface-crosslinked water-absorbing resin-derived volatile component, it is possible to prevent or reduce the aforementioned unpleasant odor. It has been particularly necessary to prevent or reduce the aforementioned unpleasant odor with respect to a water-absorbing resin surface-crosslinked at 150° C. or more (examples of a surface cross-linking agent include a polyhydric alcohol and an alkylene carbonate compound). Note, however, that Embodiment 3 makes it possible to prevent or reduce the unpleasant odor.

An embodiment of the present invention may also be configured as below.

[1] A water-absorbing resin which is a surface-crosslinked water-absorbing resin, the water-absorbing resin having a volatile component concentration of 3.5 ppm or less as measured when the water-absorbing resin is caused to stand still for 15 minutes under a condition that the water-absorbing resin has a swelling capacity of 1.0-fold, where the volatile component concentration as measured when the water-absorbing resin is caused to stand still for 15 minutes under the condition that the water-absorbing resin has a swelling capacity of 1.0-fold is a numerical value obtained by adding together concentrations of all substances that are detected by a photoion detector (PID) of a 10.6 eV lamp and that are included in a volatile component which is present in a closed vessel when 10.0 g of a physiological saline at 23.5±0.5° C. is uniformly added, under room temperature and atmospheric pressure, to 10.0 g of the water-absorbing resin contained in a 2-liter closable glass vessel and the water-absorbing resin to which the physiological saline has been added is caused to stand still in a closed state for 15 minutes, the volatile component concentration being a value represented by a detection value in terms of isobutylene, which is a calibration gas.

[2] The water-absorbing resin recited in [1], wherein a sum of volatile component concentrations as measured when the water-absorbing resin is caused to stand still for 15 minutes under conditions that the water-absorbing resin has respective swelling capacities of 0.0-fold, 0.5-fold, 1.0-fold, 2.5-fold, 5.0-fold, 10.0-fold, and 20.0-fold is 9.5 ppm or less.

[3] The water-absorbing resin recited in [1] or [2], wherein a maximum value of volatile component concentrations measured every five seconds, under a condition that the water-absorbing resin has a swelling capacity of 5.0-fold, until 900 seconds have passed since initiation of swelling of the water-absorbing resin is 0.4 ppm or less.

[4] The water-absorbing resin recited in any one of [1] to [3], wherein a sum of volatile component concentrations measured every five seconds, under a condition that the water-absorbing resin has a swelling capacity of 5.0-fold, until 900 seconds have passed since initiation of swelling of the water-absorbing resin is 50.0 ppm or less.

[5] The water-absorbing resin recited in any one of [1] to [4], wherein the water-absorbing resin has an absorption capacity without load (CRC) of 23 g/g or more and an absorption capacity under load (AAP) of 15 g/g or more.

[6] The water-absorbing resin recited in any one of [1] to [5], wherein the water-absorbing resin has a mass average particle diameter (D50) of 300 μm to 600 μm, a proportion of particles having a particle diameter of less than 150 μm in the water-absorbing resin is 5 mass % or less, and the water-absorbing resin has a logarithmic standard deviation (σζ) of a particle size distribution of 0.20 to 0.50.

[7] The water-absorbing resin recited in any one of [1] to [6], wherein the water-absorbing resin contains a volatile component reducing agent.

[8] The water-absorbing resin recited in any one of [1] to [7], wherein the water-absorbing resin has a specific surface area of 25 m²/kg or more.

[9] An absorbent article containing a water-absorbing resin recited in any one of [1] to [8].

[10] The absorbent article recited in [9], wherein the absorbent article includes an absorbent body, which is a composite containing the water-absorbing resin and a hydrophilic fiber, and the water-absorbing resin is contained in an amount of 60 mass % or more relative to a total mass of the absorbent body.

[11] A method for producing a water-absorbing resin recited in any one of [1] to [8], successively including: a polymerization step of polymerizing an acrylic acid (salt)-based monomer-containing monomer composition so as to obtain a crosslinked hydrogel polymer; a drying step of drying the crosslinked hydrogel polymer that has been obtained in the polymerization step; and a surface-crosslinking step, the method further including, at or after an end of the polymerization step, the step of adding an amino group-containing reducing agent.

[12] The method recited in [11], wherein the method includes, at or after an end of the surface-crosslinking step, the step of adding the amino group-containing reducing agent.

[13] The method recited in [11] or [12], wherein the method includes the step of adding the amino group-containing reducing agent as an aqueous solution.

[14] The method recited in any one of [11] to [13], wherein the amino group-containing reducing agent contains a hydrazide group-containing compound.

[15] A method for producing a water-absorbing resin, including the step of adding a water-based liquid in a droplet state to a surface-crosslinked water-absorbing resin so that the surface-crosslinked water-absorbing resin to which the water-based liquid has been added has a moisture content of 7.5 mass % or more, and then drying the surface-crosslinked water-absorbing resin, to which the water-based liquid has been added, so that the moisture content is reduced by an amount of 7.5 mass % or more within one hour.

[16] A method recited in [15], further including at least one of the following steps (A) and (B):
(A) adding a water-based liquid in a droplet state to the surface-crosslinked water-absorbing resin that has a specific surface area of 25 m²/kg or more; and
(B) successively including a polymerization step, a drying step of drying a hydrogel having been obtained in the polymerization step, and a surface-crosslinking step, and adding a volatile component reducing agent at or after an end of the polymerization step.

[17] The method recited in [16], wherein the method includes the step (A) of adding a water-based liquid in a droplet state to the surface-crosslinked water-absorbing resin that has a specific surface area of 25 m²/kg or more, and in a case where the water-based liquid is added so that the surface-crosslinked water-absorbing resin to which the water-based liquid has been added has a moisture content of 27.5 mass % or more, the surface-crosslinked water-absorbing resin, to which the water-based liquid has been added, is dried so that the surface-crosslinked water-absorbing resin has a moisture content of 20 mass % or less within one hour.

[18] The method recited in [16] or [17], wherein the method includes the step (B) of successively including a polymerization step, a drying step of drying a hydrogel having been obtained in the polymerization step, and a surface-crosslinking step, and adding a volatile component reducing agent at or after an end of the polymerization step.

[19] A method for producing a water-absorbing resin, including the step of bringing the water-absorbing resin into contact with a supercritical solvent so as to remove a volatile component from the water-absorbing resin, the water-absorbing resin containing a polyacrylic acid (salt)-based resin as a main component, the water-absorbing resin being internally crosslinked, and the water-absorbing resin being surface-crosslinked.

[20] The method recited in [11], wherein the method includes, at or after an end of the drying step of drying the hydrogel having been obtained in the polymerization step, the step of adding the amino group-containing reducing agent.

The present invention is not limited to the embodiments, but can be altered by a skilled person in the art within the scope of the claims. The present invention also encompasses, in its technical scope, any embodiment derived by combining technical means disclosed in differing embodiments.

EXAMPLES

The following description will discuss the present invention more concretely with reference to Examples and Comparative Examples shown below. Note, however, that the present invention is not limited to these Examples and Comparative Examples, and that any Example derived from a proper combination of technical means disclosed in respective different Examples is also encompassed in the technical scope of the present invention.

<Measurement and Evaluation of Physical Property Value Etc. of Water-Absorbing Resin>

The following description will discuss a method for measuring a water-absorbing resin (including a water-absorbing agent). A water-absorbing resin (including a water-absorbing agent) that is stored for a long period of time or removed from an absorbent body or a hygienic material such as a disposable diaper may absorb moisture and have a moisture content of more than 10 mass % (or a solid content of less than 90 mass %). Also in such a case, a volatile component concentration of the water-absorbing resin is measured while the water-absorbing resin has a moisture content of more than 10 mass %. CRC, AAP, SFC, an absorption speed, PDAUP, a mass average particle diameter, and a specific surface area of the water-absorbing resin may also be measured while the water-absorbing resin has a moisture content of more than 10 mass %. Note, however, that these physical property values are preferably measured after the moisture content of the water-absorbing resin is adjusted to 10 mass % or less. Examples of a method for adjusting the moisture content of the water-absorbing resin to 10 mass % or less include a method for drying the water-absorbing resin at 80° C. and under reduced pressure (10.0 kPa or less) for 24 hours.

Physical property values etc. of water-absorbing resins (including water-absorbing agents) obtained in Examples 1 to 12 (described later) and Comparative Examples 1 to 14 (described later) were measured and evaluated by the following method.

[Measurement of Volatile Component Concentration]

MiniRAE Lite Portable VOC Monitor PGM-7300 (manufactured by RAE Systems, Inc.) was used to measure the volatile component concentration of a water-absorbing resin. A 10.6 eV ultraviolet lamp was used for a PID detector of the device. A 100-ppm isobutylene standard gas was used to calibrate the device so as to measure an isobutylene-equivalent volatile component concentration.

A "volatile component concentration during 1.0-fold swelling", a "volatile component accumulated value during swelling at respective swelling capacities", a "maximum volatile component concentration during swelling over time", and a "volatile component accumulated value during swelling over time" of the water-absorbing resin were measured by the following method.

(a) "Volatile Component Concentration During 1.0-Fold Swelling"

A lid 9 (made of polyethylene and provided with a cap 10 having a diameter of 2.2 cm) of a glass bottle 8 (Mamemaru-kun (2 L), low storage bottle manufactured by ISHIZUKA GLASS CO., LTD.) with an internal capacity of 2 L (see FIG. 2) was opened, and 10.0 g of each of the water-absorbing resins obtained in Examples (described later) and Comparative Examples (described later) was uniformly dispersed in the glass bottle 8. After a water-absorbing resin was dispersed, 10.0 g of a physiological saline at a temperature of 23.5° C.±0.5° C. was uniformly poured into the glass bottle 8 with use of a 10.0 mL syringe (manufactured by NIPRO CORPORATION). After the physiological saline was poured into the glass bottle 8, the lid 9 was quickly closed so that the glass bottle 8 was sealed and allowed to stand in a room at a room temperature of 24° C.

After the elapse of 15 minutes since the sealing of the glass bottle 8, the cap 10 was opened so that a nozzle of the VOC Monitor PGM-7300 was inserted into the glass bottle 8. In this case, the nozzle was inserted into the glass bottle 8 until a tip of the nozzle reached a 1 cm to 2 cm position from a bottom of the glass bottle 8. Measurement with use of the volatile component monitor was carried out for 1 minute, and a maximum value of the volatile component concentration displayed on the monitor during 1 minute was regarded as a "volatile component concentration during 1.0-fold swelling".

(b) "Sum of Volatile Component Concentrations"

The "volatile component accumulated value during swelling at respective swelling capacities" was calculated by totaling respective numerical values of a "volatile component concentration during 0-fold swelling" (described below), a "volatile component concentration during 0.5-fold swelling" (described below), the "volatile component concentration during 1.0-fold swelling", a "volatile component concentration during 2.5-fold swelling" (described below), a "volatile component concentration during 5.0-fold swelling" (described below), a "volatile component concentration during 10.0-fold swelling" (described below), and a "volatile component concentration during 20.0-fold swelling" (described below).

The "volatile component concentration during 0-fold swelling", the "volatile component concentration during 0.5-fold swelling", the "volatile component concentration during 2.5-fold swelling", the "volatile component concentration during 5.0-fold swelling", the "volatile component concentration during 10.0-fold swelling", and the "volatile component concentration during 20.0-fold swelling" were measured as below.

(b-1) "Volatile Component Concentration During 0-Fold Swelling"

The lid 9 (made of polyethylene and provided with the cap 10 having a diameter of 2.2 cm) of the glass bottle 8 (Mamemaru-kun (2 L), low storage bottle manufactured by ISHIZUKA GLASS CO., LTD.) with an internal capacity of 2 L (see FIG. 2) was opened, and 10.0 g of each of the water-absorbing resins obtained in Examples (described later) and Comparative Examples (described later) was uniformly dispersed in the glass bottle 8. After a water-absorbing resin was dispersed, the lid 9 was quickly closed so that the glass bottle 8 was sealed and allowed to stand in a room at a room temperature of 24° C. for 15 minutes.

Thereafter, the cap 10 was opened so that a nozzle of the volatile component monitor PGM-7300 was inserted into the glass bottle 8. In this case, the nozzle was inserted into the glass bottle 8 until the tip of the nozzle reached a 1 cm to 2 cm position from the bottom of the glass bottle 8. Measurement with use of the VOC monitor was carried out for 1 minute, and a maximum value of the volatile component concentration displayed on the monitor during 1 minute was regarded as the "volatile component concentration during 0-fold swelling".

(b-2) "Volatile Component Concentration During 0.5-Fold Swelling"

The "volatile component concentration during 0.5-fold swelling" was measured as in the case of the measurement of the "volatile component concentration during 1.0-fold swelling" (described in (a) above) except that instead of 10.0 g of the physiological saline at a temperature of 23.5° C.±0.5° C., 5.0 g of the physiological saline at a temperature of 23.5° C.±0.5° C. was uniformly poured into the glass bottle 8 with use of the 10.0 mL syringe (manufactured by NIPRO CORPORATION).

(b-3) "Volatile Component Concentration During 2.5-Fold Swelling"

The "volatile component concentration during 2.5-fold swelling" was measured as in the case of the measurement of the "volatile component concentration during 1.0-fold swelling" (described in (a) above) except that instead of 10.0 g of the physiological saline at a temperature of 23.5° C.±0.5° C., 25 g of the physiological saline at a temperature of 23.5° C.±0.5° C. was uniformly poured into the glass bottle 8 with use of a 50 mL glass beaker.

(b-4) "Volatile Component Concentration During 5.0-Fold Swelling"

The "volatile component concentration during 5.0-fold swelling" was measured as in the case of the measurement of the "volatile component concentration during 1.0-fold swelling" (described in (a) above) except that instead of 10.0 g of the physiological saline at a temperature of 23.5° C.±0.5° C., 50 g of the physiological saline at a temperature of 23.5° C.±0.5° C. was uniformly poured into the glass bottle 8 with use of a 100 mL glass beaker.

(b-5) "Volatile Component Concentration During 10.0-Fold Swelling"

The "volatile component concentration during 10.0-fold swelling" was measured as in the case of the measurement of the "volatile component concentration during 1.0-fold swelling" (described in (a) above) except that instead of 10.0 g of the physiological saline at a temperature of 23.5° C.±0.5° C., 100 g of the physiological saline at a temperature of 23.5° C.±0.5° C. was uniformly poured into the glass bottle 8 with use of a 200 mL glass beaker.

(b-6) "Volatile Component Concentration During 20.0-Fold Swelling"

The "volatile component concentration during 20.0-fold swelling" was measured as in the case of the measurement of the "volatile component concentration during 1.0-fold swelling" (described in (a) above) except that instead of 10.0 g of the physiological saline at a temperature of 23.5° C.±0.5° C., 200 g of the physiological saline at a temperature of 23.5° C.±0.5° C. was uniformly poured into the glass bottle 8 with use of the 200 mL glass beaker.

(c) "Maximum Volatile Component Concentration During Swelling Over Time" and (d) "Volatile Component Accumulated Value During Swelling Over Time"

The lid 9 (made of polyethylene and provided with the cap 10 having a diameter of 2.2 cm) of the glass bottle 8 (Mamemaru-kun (2 L), low storage bottle manufactured by ISHIZUKA GLASS CO., LTD.) with an internal capacity of 2 L (see FIG. 2) was opened, and 10.0 g of each of the water-absorbing resins obtained in Examples (described later) and Comparative Examples (described later) was uniformly dispersed in the glass bottle 8. After a water-absorbing resin was dispersed, 50.0 g of the physiological saline at a temperature of 23.5° C.±0.5° C. was uniformly poured into the glass bottle 8 with use of a 100 mL beaker. After the physiological saline was poured into the glass bottle 8, the lid 9 was quickly closed so that the glass bottle 8 was sealed, and the cap 10 was opened so that a nozzle of the volatile component monitor PGM-7300 was inserted into the glass bottle 8. In this case, the nozzle was inserted into the glass bottle 8 until the tip of the nozzle reached a 1 cm to 2 cm position from the bottom of the glass bottle 8. Numerical values displayed on the volatile component monitor were recorded at intervals of 5 seconds from a point in time when the physiological saline was poured into the glass bottle 8. Measurement was carried out until the elapse of 900 seconds since the pouring of the physiological saline, so that volatile component concentrations at respective 180 points in total were recorded. A highest volatile component concentration of the volatile component concentrations at the respective 180 points was regarded as the "maximum volatile component concentration during swelling over time". A total sum of the volatile component concentrations at the respective 180 points was regarded as the "volatile component accumulated value during swelling over time". A working environment had a temperature of 24° C.

According to the measurement method, there is a case where a volatile component may be detected even if a similar operation is carried out without use of any water-absorbing resin. In such a case, a volatile component concentration detected from inside the glass bottle 8 in which no water-absorbing resin had been placed was subtracted so that correction was carried out.

[Absorption Capacity without Load (CRC)]

The CRC of a water-absorbing resin was measured in conformity with NWSP 241.0.R2 (15). Specifically, the absorption capacity without load (CRC) (unit: g/g) was measured after 0.2 g of the water-absorbing resin contained in a nonwoven fabric bag was immersed in a large excess of a 0.9 mass % aqueous sodium chloride solution for 30 minutes so as to be allowed to freely swell, and then the water-absorbing resin was dehydrated for 3 minutes with use of a centrifuge (250 G).

[Absorption Capacity Under Load (AAP)]

The AAP of a water-absorbing resin was measured in conformity with NWSP 242.0.R2 (15). Note, however, that in the present invention, a load under which the measurement was carried out was changed to 4.83 kPa (49 g/cm$^2$, 0.7 psi). Specifically, the AAP (absorption capacity under load) (unit: g/g) was measured after 0.9 g of the water-absorbing resin was allowed to swell for 1 hour under a load of 4.83 kPa (49 g/cm$^2$, 0.7 psi) with use of a large excess of a 0.9 mass % aqueous sodium chloride solution. That is, in the present specification, all AAP (absorption capacity under load) measurements are values measured under a load of 4.83 kPa.

[Saline Flow Conductivity (SFC)]

The saline flow conductivity (SFC) (unit: ×10$^{-7}$ cm$^3$·sec/g) of a water-absorbing resin was measured in conformity with a measurement method disclosed in U.S. Pat. No. 5,669,894.

Specifically, after 0.900 g of the water-absorbing resin was uniformly placed in a container, the water-absorbing resin was immersed in artificial urine so as to be allowed to swell under a load of 2.07 kPa. The artificial urine was prepared by mixing 0.25 g of calcium chloride dihydrate, 2.0 g of potassium chloride, 0.50 g of magnesium chloride hexahydrate, 2.0 g of sodium sulfate, 0.85 g of ammonium dihydrogen phosphate, 0.15 g of diammonium hydrogen phosphate, and 994.25 g of deionized water.

After the elapse of 60 minutes since application of the load, a height (cm) of a gel layer, which is a swollen water-absorbing resin, was recorded. Then, a 0.69 mass % saline solution was passed through the gel layer under a load of 2.07 kPa. In this case, a room temperature was adjusted to 20° C. to 25° C. Then, a balance and a computer were used to record, at intervals of 20 seconds, an amount of the saline solution passed through the gel layer so as to measure a flow rate Fs (T) of the passed saline solution. The flow rate Fs (T) was measured by dividing, by a passage time (s), a mass (g) of the passed saline solution which increases at intervals of 20 seconds. A time at which the saline solution reached a constant hydrostatic pressure, so that a stable flow rate was obtained was regarded as Ts, and data measured during 10 minutes from the Ts was used to calculate the flow rate Fs (T=0). That is, Fs (T) was plotted with respect to time so that Fs (T=0) was calculated based on a result obtained by a method of least squares. Fs (T=0) represents an initial flow rate (g/s) of the saline solution passed through the gel layer. Then, the saline flow conductivity (SFC) was calculated by the following Formula (7).

$$SFC=\{Fs(T=0)\times L0\}/(\rho \times A \times \Delta P) \qquad \text{Formula (7)}$$

In Formula (7), L0 is the height (cm) of the gel layer, p is a density (g/cm$^3$) of the saline solution, A is a cross section (cm$^2$) of the gel layer, and ΔP is a hydrostatic pressure (dyne/cm$^2$) applied to the gel layer.

[Water Absorption Speed Measured by Vortex Method]

The water absorption speed (unit: second) of a water-absorbing resin as measured by a Vortex method was measured in conformity with JIS K 7224 (1996) through the procedure below.

Specifically, 0.02 parts by weight of food blue No. 1 (CAS No. 3844-45-9) as a food additive was added to 1000 parts by mass of physiological saline so that the physiological saline was colored blue. Then, the temperature of the physiological saline was adjusted to 30° C. This was used as a test liquid.

Next, 50 mL of the test liquid was measured and put in a 100 mL capacity beaker, a cylindrical stirrer (stirrer tip) having a length of 40 mm and a diameter of 8 mm was placed in the beaker, and the test liquid started to be stirred at 600 rpm. Subsequently, 2.0 g of the water-absorbing resin was placed in the test liquid that was being stirred, a time until the cylindrical stirrer was covered with the gelated test liquid was measured, and the time until the cylindrical stirrer was covered with the gelated test liquid was regarded as a water absorption speed as measured by the Vortex method. In the following description, the water absorption speed as measured by the Vortex method is also merely expressed as a "Vortex method water absorption speed".

[Permeability Dependent Absorption Under Pressure (PDAUP)]

The PDAUP of a water-absorbing resin was measured in conformity with NWSP 243.0.R2 (15). Specifically, 5.00 g of the water-absorbing resin was weighed, and a 0.9 mass % aqueous sodium chloride solution was used to measure a fluid retention capacity (PDAUP) (unit: g/g) obtained after the water-absorbing resin was allowed to swell under a load of 4.83 kPa (49 g/cm$^2$, 0.7 psi) for 1 hour.

[Mass Average Particle Diameter and Logarithmic Standard Deviation]

The mass average particle diameter (D50, unit: µm) of a water-absorbing resin and the logarithmic standard deviation (σζ) indicative of narrowness of a particle size distribution of water-absorbing resin particles were measured in conformity with a measurement method described in "(3) Mass-Average Particle Diameter (D50) and Logarithmic Standard Deviation (σζ) of Particle Diameter Distribution", which is disclosed in U.S. Pat. No. 7,638,570.

[Proportion of Particles with Particle Diameter of 150 µm]

A JIS standard sieve (JISZ8801-1(2000)) having a mesh size of 150 µm or a sieve corresponding to a JIS standard sieve was used to classify 10 g of a water-absorbing resin. Regarding a classification condition, a vibration classifier (IIDA SIEVE SHAKER, Type: ES-65, SER. No. 0501) was used to carry out classification for 5 minutes. After classification was carried out, a mass of particles having a particle diameter of less than 150 µm was used to measure a proportion of the particles having a particle diameter of less than 150 µm [mass %] based on the following formula:

Proportion of particles having a particle diameter of less than 150 µm [mass %]={mass [g] of particles passed through mesh size of 150 µm/ (mass [g] of water-absorbing resin)}×100

[D50 (Mass Average Particle Diameter) of Particulate Hydrogel]

The mass average particle diameter of a crosslinked particulate hydrogel polymer was measured in accordance with the following method.

That is, 20 g of the pulverized particulate hydrogel (solid content: a mass %) having a temperature of 20° C. to 25° C. was added to 500 g of a 20 mass % aqueous sodium chloride solution (hereinafter referred to as "EMAL aqueous solution") containing a 0.08 mass % EMAL 20C (surfactant; manufactured by Kao Corporation), so that a dispersion liquid was obtained. The dispersion liquid was then stirred with use of a stirrer tip having a length of 50 mm and a diameter of 7 mm at 300 rpm for 1 hour (with use of a cylindrical polypropylene container having a height of 21 cm and a diameter of 8 cm (capacity: approximately 1.14 L)).

After the stirring was finished, the resultant dispersion liquid was introduced into the center of a set of JIS standard sieves (having a diameter of 21 cm and having respective mesh sizes of 8 mm, 4 mm, 2 mm, 1 mm, 0.60 mm, 0.30 mm, 0.15 mm, and 0.075 mm) which were placed on a rotary table in such a manner as to be stacked on top of each other. After the entire particulate hydrogel was washed out onto the sieves with use of 100 g of an EMAL aqueous solution, the particulate hydrogel was classified by uniformly spraying 6000 g of an EMAL aqueous solution onto the sieves from 30 cm above with use of a shower (with 72 holes, flow rate: 6.0 L/min) in a manner such that the spraying area (50 cm²) entirely covered the sieve, while rotating the sieve by hand (20 rpm). The particulate hydrogel, which had been subjected to the classification, on the first sieve from the top was drained for approximately 2 minutes, and was then weighed. For the second sieve from the top and the subsequent sieves, classification was carried out by the same operation. After the draining, the particulate hydrogel remaining on each of the sieves was weighed.

From the mass of the particulate hydrogel remaining on each sieve, a mass percentage X (unit: mass %) in the entire particulate hydrogel was calculated by use of Formula (8) below. A mesh size R(α) (unit: mm) of the sieve used for the particulate hydrogel remaining on the sieve and having a solid content of a mass % was calculated in accordance with Formula (9) below. X and R(α) of the particulate hydrogel remaining on each of the sieves were plotted on a logarithmic probability paper, so that a graph (particle size distribution) showing a relationship between a cumulative weight ratio of X and R(α) was made. From this graph, a particle diameter at which a residual percentage corresponds to 50 mass % was read as the mass average particle diameter (D50) of the particulate hydrogel.

$$X=(w/W)\times 100 \qquad \text{Formula (8)}$$

$$R(\alpha)=(20/W)^{1/3}\times r \qquad \text{Formula (9)}$$

Note here that X, w, W, R(α), and r mean the following values.

X represents a percentage by mass (unit: mass %) of a particulate hydrogel remaining on each sieve after classification and draining.

w represents a mass (unit: g) of each particulate hydrogel remaining on each sieve after classification and draining.

W represents a total mass (unit: g) of particulate hydrogels remaining on the respective sieves after classification and draining.

R(α) represents a mesh size (unit: mm; calculated value) of a sieve used to classify a particulate hydrogel having a mass % on a solid content basis.

r represents a mesh size (unit: mm; measured value) of a JIS standard sieve with which a particulate hydrogel swollen in a 20 mass % aqueous sodium chloride solution containing 0.08 mass % EMAL 20C (surfactant, manufactured by Kao Corporation) is classified.

[Specific Surface Area]

The specific surface area of a water-absorbing resin is a value found by analyzing, with use of high-speed three-dimensional analysis software (TRI/3D-VOL-FCS64; manufactured by Ratoc System Engineering Co., Ltd.), three-dimensional image data obtained with use of Micro-focus X-ray CT system (inspeXio SMX-100CT; manufactured by Shimadzu Corporation).

The three-dimensional image data obtained with use of the inspeXio SMX-100CT was obtained by producing a sample in which a glass vial having a body diameter of 1 cm and a total length of 4 cm was filled with 1 g of the water-absorbing resin, affixing a double-sided tape to a bottom surface of the vial, and carrying out measurement under the following conditions while the sample is fixed onto a sample stage of the inspeXio SMX-100CT.

X-ray tube voltage (kV): 50
X-ray tube current (pA): 40
Inch size (inch): 4.0
X-ray filter: None
SDD (mm): 500
SRD (mm): 40
Z (mm): 108
X (mm): 0
Y (mm): 0
CT mode 1: CBCT
CT mode 2: Normal scan
Scan angle: Full scan
Number of views: 1200
Average number: 5
Number of times of multi-rotation: None
Smoothing: YZ
Slice thickness (mm): 0.008
Distance between slices (mm): 0.010
Scaling coefficient: 50
BHC data: None Fine mode: Available
FOV XY (mm): 5.0
FOV Z (mm): 4.0
Voxel size (mm/voxel): 0.010

In image analysis carried out with use of TRI/3D-VOL-FCS64, the analysis was carried out in accordance with the following procedures (1) to (6):

(1) an L value was set to 37580, and all particles (water-absorbing resin particles) in a measurement target region were extracted; (2) a process for removing particles having a size of 10 voxels or less and considered to be a noise was carried out; (3) a closed cell inside each particle was extracted; (4) a process for combining particles that were originally a single particle but was regarded as a plurality of particles, or a process for separating a particle that was originally a plurality of particles but was regarded as a single particle was carried out; (5) a process for removing edge particles was carried out; and (6) a unit was set to a voxel, and a total surface area and an apparent total volume of all the particles in the measurement target region, and a total volume of closed cells were calculated. Note that the apparent total volume refers to a total volume of all particles calculated assuming that there is no closed cell inside a particle.

A value obtained by the image analysis was used to calculate a specific surface area of a water-absorbing resin from Formula (10) below. A true density of the water-absorbing resin in Formula (10) below was fixed to 1.7 kg/m$^3$ in the present invention so that the specific surface area was calculated. The true density was measured by a method disclosed in Japanese Patent No. 6093751. Thus, in a case where the true density is unknown, a dry density of the water-absorbing resin having been pulverized to have a particle diameter of less than 45 μm was measured, and the dry density was regarded as the true density.

Specific surface area (m$^2$/kg)=total surface area (m$^2$)/{apparent total volume (m$^3$)−total volume (m$^3$) of closed cells×true density (kg/m$^3$) of water-absorbing resin     Formula (10)

[Moisture Content, Solid Content]

The moisture content (unit: mass %) of a water-absorbing resin was measured in conformity with NWSP 230.0.R2 (15). Note that, for the present invention, out of the measurement conditions defined in NWSP 230.0.R2 (15), the amount of a water-absorbing resin (sample) was changed to 1.0 g, and the drying temperature was changed to 180° C.

A value of the moisture content measured as above was used to calculate the solid content (unit: mass %) of a water-absorbing resin from Formula (11) below.

Solid content (mass %)=100−moisture content (mass %)     Formula (11)

[Evaluation of Odor]
(Production of Absorbent Body)

Two pieces of nonwoven fabric (Heat-Ron paper LFPWTF, manufactured by Daio Paper Corporation) cut into a rectangle measuring 10 cm×16 cm were stacked on top of another, and a heat sealer was used to thermally weld three sides of the stacked pieces, so that a nonwoven bag with one side open was produced. Next, after 10 parts by mass of a water-absorbing resin was placed in the nonwoven bag, the remaining one side of the nonwoven bag was closed by thermal welding so that the water-absorbing resin would not leak. Thus, an absorbent body for evaluation was obtained.

(Evaluation of Odor of Absorbent Body)

Figure 2:
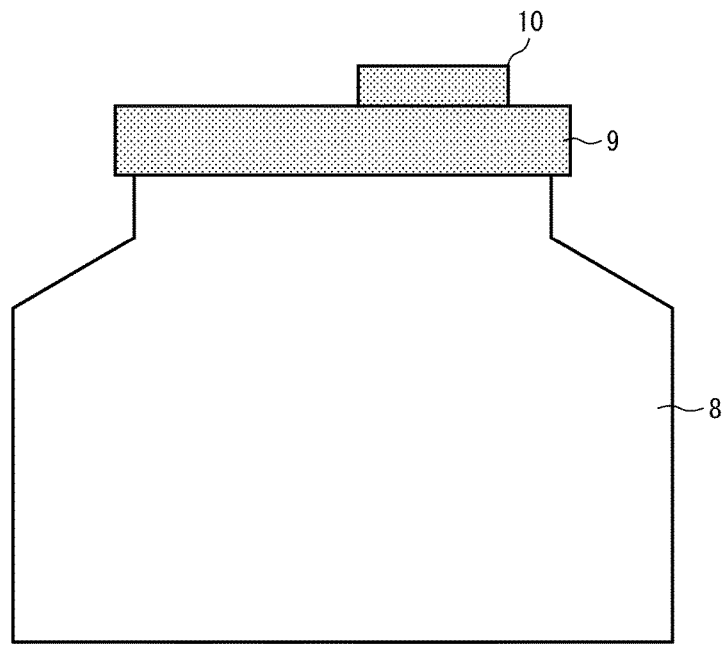
FIG. 2 is a view illustrating a closed vessel that is used to measure a volatile component concentration.

An odor of an absorbent body was evaluated through the following procedures (1) to (4):

(1) first, the absorbent body was placed in the lid 9 (made of polyethylene and provided with the cap 10 having a diameter of 2.2 cm) of the glass bottle 8 (Mamemaru-kun (2 L), low storage bottle manufactured by ISHIZUKA GLASS CO., LTD.) with an internal capacity of 2 L (see FIG. 2); (2) 50 g of the physiological saline at 23.5±0.5° C. was poured into the glass bottle 8; (3) the lid 9 was quickly closed, and the glass bottle 8 was sealed and allowed to stand in a room at a room temperature of 24° C.; and (4) after the elapse of 10 minutes since the sealing of the glass bottle 8, the lid 9 was opened, and 10 adult panelists smelled an odor of air above the absorbent body so that odor evaluation was carried out. Thus, the glass bottle 8 was prepared for each of the panelists.

An evaluation method was a method in which an evaluation on a scale of 1 to 6 where: 0 indicates that no odor is perceived; and 5 indicates that an unpleasant odor is strongly perceived was carried out in accordance with unpleasantness felt by a subject. Such an odor point that is lower shows that less unpleasant odor is perceived.

<Determination Criteria>

0: Same as ambient air.

1: An odor is slightly perceived, but it is impossible to express what the odor is like (note, however, that the odor is neither unpleasant nor annoying).

2: An odor is perceived but is not unpleasant.

3: An odor is perceived and is unpleasant.

4: An odor is strongly perceived but is not unpleasant.

5: An odor is strongly perceived and is unpleasant.

The panelists each carried out the odor evaluation in accordance with the above determination criteria so that an average (with decimals rounded to the nearest whole number) was found. The average thus found was regarded as an evaluation of an odor of a swollen gel obtained by swelling of a water-absorbing resin. The reason why "An odor is strongly perceived but is not unpleasant." is evaluated worse than "An odor is perceived and is unpleasant." in the determination criteria is that since it varies between individuals whether odor quality is comfortable or uncomfortable, a case where an odor is strongly perceived is higher in risk when a water-absorbing resin is used as a hygienic material.

[Acrylic Acid]

A p-methoxyphenol content, a protoanemonin content, and an aldehyde content in an acrylic acid used in Examples was 70 ppm, ND (less than 1 ppm), and ND (less than 1 ppm), respectively. Furthermore, the acrylic acid had an acetic acid content of 1470 ppm, a propionic acid content of 270 ppm, and an acrylic acid dimer content of 90 ppm.

Production Example 1

First, 1.8 g of polyethylene glycol acrylate (average addition mole number of ethylene oxide: 9) was dissolved into 2000 g of an aqueous sodium acrylate solution (monomer concentration: 39 mass %, Fe content: 0.28 ppm) having a neutralization rate of 75 mol %, so that a reaction solution (1) was obtained. The reaction solution (1) thus obtained was poured into a stainless steel vat-type vessel containing a magnetic stirrer and having a size of 320 mm in length, 220 mm in width, and 50 mm in height. In this case, the reaction solution had a depth of 23 mm. An upper part of the vat-type vessel was sealed with a polyethylene film provided with a nitrogen gas inlet, an outlet, and a polymerization initiator inlet. Thereafter, the vat-type vessel was immersed in a water bath at a water temperature of 25° C. While the temperature of the reaction solution was maintained at 25° C., nitrogen gas was introduced into the reaction solution so that dissolved oxygen in the reaction solution was removed. Subsequently, nitrogen gas continued to be introduced into and discharged from a space in an upper part of the reaction solution in the vat-type vessel. That is, an atmosphere in the space was nitrogen gas.

Thereafter, as a polymerization initiator, 10.5 g of a 10 mass % aqueous sodium persulfate solution and 1.4 g of a 1 mass % aqueous L-ascorbic acid solution were poured and sufficiently mixed with the magnetic stirrer. A polymerization reaction commenced 2 minutes after the introduction of the polymerization initiator. Thus, an operation to immerse the vat-type vessel in a water bath at a water temperature of 12° C. up to a height of 10 mm from a bottom of the vat-type vessel was intermittently repeatedly carried out so that a polymerization temperature was controlled. The polymerization temperature reached 85° C. (peak temperature) 15 minutes after the commencement of the polymerization reaction. Thus, in order that a generated hydrogel polymer would be matured, the vat-type vessel was immersed in a water bath at a water temperature of 60° C. up to a height of 10 mm from the bottom of the vat-type vessel and maintained for 20 minutes. Thereafter, the hydrogel polymer thus obtained was subjected to gel-crushing with use of a meat chopper provided with a die with 18 holes each having a diameter of 11 mm (model number: HL-G22SN, manufactured by Remacom Co., Ltd.) so that a crosslinked particulate hydrogel polymer (1) was obtained. The crosslinked particulate hydrogel polymer (1) had a mass average particle diameter of 2500 μm.

The crosslinked particulate hydrogel polymer (1) was spread onto a 50-mesh metal gauze (mesh size: 300 μm) and then dried with hot air at a temperature of 180° C. for 30 minutes with use of a batch-type ventilation dryer (type: 71-S6, manufactured by Satake Chemical Equipment Mfg Ltd.). Next, a resultant dried material was subjected to a pulverizing step of carrying out pulverization with use of a roll mill, and a pulverized substance was classified with use of metal gauzes having respective mesh sizes of 710 μm and 150 μm. In this way, particulate crosslinked polymer powder (a) having a particle diameter of 150 μm to 710 μm and having a non-uniformly pulverized shape and crosslinked polymer powder (b) in fine powder form having a particle diameter of less than 150 μm were obtained.

The above-described procedure was repeatedly carried out, so that 500 g of the crosslinked polymer powder (b) was obtained. Into a 5-liter mortar mixer (manufactured by Nishinihon Shikenki Seisakusho) kept warm in a water bath at a water temperature of 80° C., 300 g of the crosslinked polymer powder (b) was put. While a stirring blade of the mortar mixer was rotated at a high speed with 60 Hz/100 V, 450 g of water for granulation of fine particles, adjusted to 80° C., was introduced at once into the mortar mixer. Within 10 seconds of the introduction of the water, the crosslinked polymer powder (b) and the water were mixed together so as to be a granulated material. The granulated material was taken out 10 minutes after the introduction of the water, so that a granulated gel having a particle diameter of 3 mm to 10 mm was obtained. Furthermore, 600 g of the granulated gel thus obtained and 600 g of the crosslinked particulate hydrogel polymer (1) obtained by repeatedly carrying out the above-described procedure were lightly mixed together. Thereafter, a resultant mixture was spread onto a 50-mesh metal gauze (mesh size: 300 μm) and then dried with hot air at a temperature of 180° C. for 30 minutes with use of a batch-type ventilation dryer (type: 71-S6, manufactured by Satake Chemical Equipment Mfg Ltd.). Next, a resultant dried material was subjected to a pulverizing step of carrying out pulverization with use of a roll mill, and a pulverized substance was classified with use of metal gauzes having respective mesh sizes of 710 μm and 150 μm. In this way, crosslinked polymer powder (c) having a particle diameter of 150 μm to 710 μm and having a non-uniformly pulverized shape was obtained. Physical properties of the crosslinked polymer powder (c) together with those of the crosslinked polymer powder (a) are shown in Table 2.

Production Example 2

Into a 2-liter polypropylene container were introduced 400 parts by mass of acrylic acid, 185 parts by mass of a 48 mass % aqueous sodium hydroxide solution, 2.3 parts by mass of polyethyleneglycol diacrylate (average addition mole number of ethylene oxide: 9), 1.3 parts by mass of a 2 mass % aqueous diethylenetriamine pentaacetic acid/trisodium solution, 5 parts by mass of a 10 mass % aqueous polyoxyethylene oleyl ether (manufactured by Kao Corporation) solution, and 368 parts by weight of deionized water. These substances were mixed so that an aqueous solution (1) was prepared. The deionized water had been preheated to 40° C.

Next, while the aqueous solution (1) was stirred, 185 parts by mass of a 48 mass % aqueous sodium hydroxide solution was added to and mixed with the aqueous solution (1) under atmospheric pressure over a period of approximately 30 seconds. In this way, an aqueous monomer solution (1) was prepared. Note that a temperature of the aqueous monomer solution (1) increased to approximately 84° C. due to heat of neutralization and heat of dissolution which were generated during the mixing.

Thereafter, when the temperature of the aqueous monomer solution (1) reached 83° C., 13 parts by mass of a 5 mass % aqueous sodium persulfate solution was added as a polymerization initiator, and a resultant mixture was stirred for approximately 5 seconds so that a reaction solution (2) was obtained.

Next, the reaction solution (2) was poured into a stainless steel vat-type vessel (with a bottom surface of 340 mm×340 mm and a height of 25 mm; inner surface: Teflon (registered trademark) coating) under atmospheric pressure. Note that the vat-type vessel was preheated with use of a hot plate so as to have a surface temperature of 40° C.

After the reaction solution (2) was poured into the vat-type vessel, a polymerization reaction commenced within 1 minute. As the polymerization reaction proceeded, the polymerization reaction caused the reaction solution (2) to expand and foam upward in various directions while water vapor was generated. Thereafter, the reaction solution (2) contracted to a size slightly larger than the bottom surface of the vat-type vessel. The polymerization reaction ended within approximately 1 minute. Through this polymerization reaction, a crosslinked hydrogel polymer (2) was obtained.

Next, the crosslinked hydrogel polymer (2) was cut into an appropriate size and then subjected to gel-crushing with use of a meat chopper provided with a die with 33 holes each having a diameter of 8 mm (model number: HL-G22SN, manufactured by Remacom Co., Ltd.) so that a crosslinked particulate hydrogel polymer (2) was obtained. The crosslinked particulate hydrogel polymer (2) had a mass average particle diameter of 700 μm.

The crosslinked particulate hydrogel polymer (2) was spread onto a 50-mesh metal gauze (mesh size: 300 μm) and then dried with hot air at a temperature of 180° C. for 30 minutes with use of a batch-type ventilation dryer (type: 71-S6, manufactured by Satake Chemical Equipment Mfg Ltd.). Next, a resultant dried material was subjected to a pulverizing step of carrying out pulverization with use of a roll mill, and a pulverized substance was classified with use of metal gauzes having respective mesh sizes of 710 μm and 150 μm. In this way, crosslinked polymer powder (d) having a particle diameter of 150 μm to 710 μm and having a non-uniformly pulverized shape (being particulate) was obtained. Physical properties of the crosslinked polymer powder (d) are shown in Table 2.

Production Example 3

Into a 2-liter polypropylene container were introduced 400 parts by mass of acrylic acid, 185 parts by mass of a 48 mass % aqueous sodium hydroxide solution, 2.5 parts by mass of polyethyleneglycol diacrylate (average addition mole number of ethylene oxide: 9), 1.3 parts by mass of a 2 mass % aqueous diethylenetriamine pentaacetic acid/trisodium solution, and 373 parts by weight of deionized water. These substances were mixed so that an aqueous solution (2) was prepared. The deionized water had been preheated to 40° C.

Next, while the aqueous solution (2) was stirred, 185 parts by mass of a 48 mass % aqueous sodium hydroxide solution was added to and mixed with the aqueous solution (2) under atmospheric pressure over a period of approximately 30 seconds. In this way, an aqueous monomer solution (2) was prepared. Note that a temperature of the aqueous monomer solution (2) increased to approximately 84° C. due to heat of neutralization and heat of dissolution which were generated during the mixing.

Thereafter, when the temperature of the aqueous monomer solution (2) reached 83° C., 13 parts by mass of a 5 mass % aqueous sodium persulfate solution was added as a polymerization initiator, and a resultant mixture was stirred for approximately 5 seconds so that a reaction solution (3) was obtained.

Next, the reaction solution (3) was poured into a stainless steel vat-type vessel (with a bottom surface of 340 mm×340 mm and a height of 25 mm; inner surface: Teflon (registered trademark) coating) under atmospheric pressure. Note that the vat-type vessel was preheated with use of a hot plate so as to have a surface temperature of 40° C.

After the reaction solution (3) was poured into the vat-type vessel, a polymerization reaction commenced within 1 minute. As the polymerization reaction proceeded, the polymerization reaction caused the reaction solution (3) to expand and foam upward in various directions while water vapor was generated. Thereafter, the reaction solution (3) contracted to a size slightly larger than the bottom surface of the vat-type vessel. The polymerization reaction ended within approximately 1 minute. Through this polymerization reaction, a crosslinked hydrogel polymer (3) was obtained.

Next, the crosslinked hydrogel polymer (3) was cut into an appropriate size and then subjected to gel-crushing with use of a meat chopper provided with a die with 52 holes each having a diameter of 6 mm (model number: HL-G22SN, manufactured by Remacom Co., Ltd.) so that a crosslinked particulate hydrogel polymer (3) was obtained. The crosslinked particulate hydrogel polymer (3) had a mass average particle diameter of 400 μm.

The crosslinked particulate hydrogel polymer (3) was spread onto a 50-mesh metal gauze (mesh size: 300 μm) and then dried with hot air at a temperature of 180° C. for 30 minutes with use of a batch-type ventilation dryer (type: 71-S6, manufactured by Satake Chemical Equipment Mfg Ltd.). Next, a resultant dried material was subjected to a pulverizing step of carrying out pulverization with use of a roll mill, and a pulverized substance was classified with use of metal gauzes having respective mesh sizes of 710 μm and 150 μm. In this way, crosslinked polymer powder (e) having a particle diameter of 150 μm to 710 μm and having a non-uniformly pulverized shape (being particulate) was obtained. Physical properties of the crosslinked polymer powder (e) are shown in Table 2.

Production Example 4

Into a 1-liter polypropylene container having an inner diameter of 80 mm and covered with styrene foam (heat insulating material) were introduced 291.0 parts by mass of acrylic acid, 0.43 parts by mass of polyethyleneglycol diacrylate (average addition mole number of ethylene oxide: 9), 3.6 parts by mass of an acrylic acid solution obtained by dissolving 1.0 mass % IRGACURE (registered trademark) 184 in acrylic acid, 0.61 parts by mass of 0.45 mass % diethylenetriamine sodium pentaacetate, and 255 parts by weight of deionized water. These substances were mixed so that an aqueous solution (3) was prepared. The deionized water had been preheated to 50° C.

Next, while the aqueous solution (3) was stirred, 247 parts by mass of a 48 mass % aqueous sodium hydroxide solution was added to and mixed with the aqueous solution (3) under atmospheric pressure over a period of approximately 30 seconds. In this way, an aqueous monomer solution (4) was prepared. Note that a temperature of the aqueous monomer solution (4) increased to approximately 100° C. due to heat of neutralization and heat of dissolution which were generated during the mixing.

Thereafter, when the temperature of the aqueous monomer solution (4) reached 98° C., 1.8 parts by mass of a 3 mass % aqueous sodium persulfate solution was added as a polymerization initiator, and a resultant mixture was stirred for approximately 1 second so that a reaction solution (4) was obtained.

Next, the reaction solution (4) was poured into a stainless steel vat-type vessel (with a bottom surface of 340 mm×340 mm and a height of 25 mm; inner surface: Teflon (registered trademark) coating) under atmospheric pressure. Further, while the reaction solution (4) was being poured into the stainless steel vat-type vessel, an ultraviolet ray was applied to the reaction solution (4).

After the reaction solution (4) was poured into the vat-type vessel, a polymerization reaction commenced within 1 minute. The application of the ultraviolet ray was stopped 3 minutes thereafter, so that a crosslinked hydrogel polymer (4) was obtained.

Next, the crosslinked hydrogel polymer (4) was cut into an appropriate size and then subjected to gel-crushing with use of a meat chopper provided with a die with 38 holes each having a diameter of 7.5 mm (model number: HL-G22SN, manufactured by Remacom Co., Ltd.) so that a crosslinked particulate hydrogel polymer (4) was obtained. The crosslinked particulate hydrogel polymer (4) had a mass average particle diameter of 1000 μm.

The crosslinked particulate hydrogel polymer (4) was spread onto a 50-mesh metal gauze (mesh size: 300 μm) and then dried with hot air at a temperature of 180° C. for 30 minutes with use of a batch-type ventilation dryer (type: 71-S6, manufactured by Satake Chemical Equipment Mfg Ltd.). Next, a resultant dried material was subjected to a pulverizing step of carrying out pulverization with use of a roll mill, and a pulverized substance was classified with use of metal gauzes having respective mesh sizes of 710 μm and 150 μm. In this way, crosslinked polymer powder (f) having a particle diameter of 150 μm to 710 μm and having a non-uniformly pulverized shape (being particulate) was obtained. Physical properties of the crosslinked polymer powder (f) are shown in Table 2.

Production Example 5

Into a reactor formed by providing a lid to a twin-armed jacketed stainless steel kneader having two sigma type blades and a capacity of 10 L were introduced 425.2 parts by mass of acrylic acid, 4499.5 parts by mass of a 37 mass % aqueous sodium acrylate solution, 538.5 parts by mass of deionized water, and 4.3 parts by mass of polyethyleneglycol diacrylate (average addition mole number of ethylene oxide: 9), so that a reaction solution (5) was prepared. The reaction solution (5) was degassed in a nitrogen atmosphere for 30 minutes.

Next, while the reaction solution (5) was stirred, 28.3 parts by mass of a 10 mass % aqueous sodium persulfate solution and 1.5 parts by mass of a 1 mass % aqueous L-ascorbic acid solution were added thereto. Polymerization commenced approximately 1 minute thereafter. A temperature of the reaction solution (5) reached a polymerization peak temperature of 86° C. 17 minutes after the commencement of polymerization. A crosslinked hydrogel polymer (5) was removed from the reactor 60 minutes after the commencement of polymerization. The crosslinked hydrogel polymer (5) thus obtained was a grain-refined crosslinked particulate hydrogel polymer. The crosslinked particulate hydrogel polymer (5) had a mass average particle diameter of 1500 μm.

The crosslinked particulate hydrogel polymer (5) was spread onto a 50-mesh metal gauze (mesh size: 300 μm) and then dried with hot air at a temperature of 170° C. for 65 minutes with use of a batch-type ventilation dryer (type: 71-S6, manufactured by Satake Chemical Equipment Mfg Ltd.). Next, a resultant dried material was pulverized with use of a roll mill, and a resultant pulverized substance was classified with use of metal gauzes having respective mesh sizes of 710 μm and 150 μm. In this way, crosslinked polymer powder (g) having a particle diameter of 150 μm to 710 μm and having a non-uniformly pulverized shape (being particulate) was obtained. Physical properties of the crosslinked polymer powder (g) are shown in Table 2.

TABLE 2

| | | CRC | Specific surface area (m$^2$/kg) |
|---|---|---|---|
| Production Example 1 | Crosslinked polymer powder (a) | 40.5 | 20.6 |
| Production Example 1 | Crosslinked polymer powder (c) | 40.2 | 32.3 |
| Production Example 2 | Crosslinked polymer powder (d) | 36.3 | 31.9 |
| Production Example 3 | Crosslinked polymer powder (e) | 32.2 | 35.5 |
| Production Example 4 | Crosslinked polymer powder (f) | 52.0 | 28.0 |

TABLE 2-continued

| | | CRC | Specific surface area (m$^2$/kg) |
|---|---|---|---|
| Production Example 5 | Crosslinked polymer powder (g) | 42.0 | 23.8 |

Comparative Example 1

With 100 parts by mass of the crosslinked polymer powder (c), an aqueous surface-crosslinking agent solution (4.0 parts by mass) containing 0.3 parts by mass of ethylene carbonate, 0.7 parts by mass of propylene glycol, and 3 parts by mass of deionized water was spray-mixed with use of a spray. A mixer having a heating medium temperature of 210° C. was used to subject a resultant mixture to a heating treatment for 40 minutes and then crush the mixture until the mixture passed through a JIS standard sieve having a mesh size of 710 μm. Thus, a base water-absorbing resin (1) serving as a surface-crosslinked water-absorbing resin was obtained. Physical properties of the base water-absorbing resin (1) are shown in Table 3.

Comparative Example 2

Operations similar to those carried out in Comparative Example 1 were carried out except that with 100 parts by mass of the crosslinked polymer powder (c) obtained in Production Example 1, an aqueous surface-crosslinking agent solution (4.0 parts by mass) containing 1.0 part by mass of triethylene glycol and 3 parts by mass of deionized water was spray-mixed with use of a spray. Thus, a base water-absorbing resin (2) serving as a surface-crosslinked water-absorbing resin was obtained. Physical properties of the base water-absorbing resin (2) are shown in Table 3.

Comparative Example 3

Operations similar to those carried out in Comparative Example 1 were carried out except that with 100 parts by mass of the crosslinked polymer powder (c) obtained in Production Example 1, an aqueous surface-crosslinking agent solution (6.0 parts by mass) containing 1.0 part by mass of ethylene carbonate, 1.0 part by mass of propylene carbonate, and 4 parts by mass of deionized water was spray-mixed with use of a spray. Thus, a base water-absorbing resin (3) serving as a surface-crosslinked water-absorbing resin was obtained. Physical properties of the base water-absorbing resin (3) are shown in Table 3.

Comparative Example 4

Operations similar to those carried out in Comparative Example 1 were carried out except that with 100 parts by mass of the crosslinked polymer powder (d) obtained in Production Example 2, an aqueous surface-crosslinking agent solution (3.3 parts by mass) containing 0.8 parts by mass of ethylene glycol and 2.5 parts by mass of deionized water was spray-mixed with use of a spray. Thus, a base water-absorbing resin (4) serving as a surface-crosslinked water-absorbing resin was obtained. Physical properties of the base water-absorbing resin (4) are shown in Table 3.

Comparative Example 5

Operations similar to those carried out in Comparative Example 1 were carried out except that with 100 parts by mass of the crosslinked polymer powder (d) obtained in Production Example 2, an aqueous surface-crosslinking agent solution (4.0 parts by mass) containing 0.8 parts by mass of propylene glycol, 0.8 parts by mass of 1,6-hexanediol, and 2.4 parts by mass of deionized water was spray-mixed with use of a spray. Thus, a base water-absorbing resin (5) serving as a surface-crosslinked water-absorbing resin was obtained. Physical properties of the base water-absorbing resin (5) are shown in Table 3.

Comparative Example 6

Operations similar to those carried out in Comparative Example 1 were carried out except that with 100 parts by mass of the crosslinked polymer powder (d) obtained in Production Example 2, an aqueous surface-crosslinking agent solution (4.0 parts by mass) containing 0.5 parts by mass of triethylene glycol, 0.5 parts by mass of propylene glycol, and 3.0 parts by mass of deionized water was spray-mixed with use of a spray. Thus, a base water-absorbing resin (6) serving as a surface-crosslinked water-absorbing resin was obtained. Physical properties of the base water-absorbing resin (6) are shown in Table 3.

Comparative Example 7

Operations similar to those carried out in Comparative Example 1 were carried out except that with 100 parts by mass of the crosslinked polymer powder (e), an aqueous surface-crosslinking agent solution (3.8 parts by mass) containing 0.4 parts by mass of 1,4-butanediol, 0.6 parts by mass of propylene glycol, and 2.8 parts by mass of deionized water was spray-mixed with use of a spray. Thus, a base water-absorbing resin (7) serving as a surface-crosslinked water-absorbing resin was obtained. Physical properties of the base water-absorbing resin (7) are shown in Table 3.

Comparative Example 8

Operations similar to those carried out in Comparative Example 1 were carried out except that with 100 parts by mass of the crosslinked polymer powder (e), an aqueous surface-crosslinking agent solution (4.0 parts by mass) containing 0.3 parts by mass of triethylene glycol, 0.3 parts by mass of 1,6-hexanediol, and 3.4 parts by mass of deionized water was spray-mixed with use of a spray. Thus, a base water-absorbing resin (8) serving as a surface-crosslinked water-absorbing resin was obtained. Physical properties of the base water-absorbing resin (8) are shown in Table 3.

Comparative Example 9

Operations similar to those carried out in Comparative Example 1 were carried out except that with 100 parts by mass of the crosslinked polymer powder (e), an aqueous surface-crosslinking agent solution (4.0 parts by mass) containing 0.4 parts by mass of ethylene carbonate, 0.7 parts by mass of 1,6-hexanediol, and 2.9 parts by mass of deionized water was spray-mixed with use of a spray. Thus, a base water-absorbing resin (9) serving as a surface-crosslinked water-absorbing resin was obtained. Physical properties of the base water-absorbing resin (9) are shown in Table 3.

Comparative Example 10

Operations similar to those carried out in Comparative Example 1 were carried out except that with 100 parts by mass of the crosslinked polymer powder (a), an aqueous surface-crosslinking agent solution (5.0 parts by mass) containing 0.4 parts by mass of ethylene carbonate, 0.7 parts by mass of 1,6-hexanediol, and 3.9 parts by mass of deionized water was spray-mixed with use of a spray. Thus, a base water-absorbing resin (10) serving as a surface-crosslinked water-absorbing resin was obtained. Physical properties of the base water-absorbing resin (10) are shown in Table 3.

Comparative Example 11

With 100 parts by mass of the crosslinked polymer powder (f), an aqueous surface-crosslinking agent solution (5.03 parts by mass) containing 0.03 parts by mass of ethylene glycol diglycidyl ether, 1.50 parts by mass of propylene glycol, and 3.50 parts by mass of deionized water was spray-mixed with use of a spray. A mixer having a heating medium temperature of 100° C. was used to subject a resultant mixture to a heating treatment for 45 minutes and then crush the mixture until the mixture passed through a JIS standard sieve having a mesh size of 710 μm. Thus, a base water-absorbing resin (11) serving as a surface-crosslinked water-absorbing resin was obtained. Physical properties of the base water-absorbing resin (11) are shown in Table 3.

Comparative Example 12

Operations similar to those carried out in Comparative Example 1 were carried out except that with 100 parts by mass of the crosslinked polymer powder (g), an aqueous surface-crosslinking agent solution (3.8 parts by mass) containing 0.3 parts by mass of 1,4-butanediol, 0.5 parts by mass of propylene glycol, and 3.0 parts by mass of deionized water was spray-mixed with use of a spray. Thus, a base water-absorbing resin (12) serving as a surface-crosslinked water-absorbing resin was obtained. Physical properties of the base water-absorbing resin (12) are shown in Table 3.

TABLE 3

| | Surface-crosslinked water-absorbing resin | Base polymer | Surface-treating agent | Solid content (mass %) | CRC (g/g) | AAP (g/g) | SFC (sec/g) | Vortex (sec) |
|---|---|---|---|---|---|---|---|---|
| Comparative Example 1 | Base water-absorbing resin 1 | Crosslinked polymer powder (c) | EC/PG/PW = 0.3/0.7/3.0 | 97.9 | 31.0 | 23.7 | 30 | 27 |
| Comparative Example 2 | Base water-absorbing resin 2 | Crosslinked polymer powder (c) | TEG/PW = 1.0/3.0 | 98.2 | 31.5 | 24.0 | 28 | 30 |
| Comparative Example 3 | Base water-absorbing resin 3 | Crosslinked polymer powder (c) | EC/PC/PW = 1.0/1.0/4.0 | 98.1 | 33.2 | 23.2 | 10 | 31 |
| Comparative Example 4 | Base water-absorbing resin 4 | Crosslinked polymer powder (d) | EG/PW = 0.8/2.5 | 97.8 | 29.8 | 26.2 | 33 | 28 |

TABLE 3-continued

| | | | | | | | |
|---|---|---|---|---|---|---|---|
| Comparative Example 5 | Base water-absorbing resin 5 | Crosslinked polymer powder (d) | HD/PG/PW = 0.8/0.8/2.4 | 98.2 | 29.3 | 26.0 | 34 | 30 |
| Comparative Example 6 | Base water-absorbing resin 6 | Crosslinked polymer powder (d) | TEG/PG/PW = 0.5/0.5/3.0 | 98.2 | 30.5 | 25.0 | 23 | 29 |
| Comparative Example 7 | Base water-absorbing resin 7 | Crosslinked polymer powder (e) | BD/PG/PW = 0.4/0.6/2.8 | 97.9 | 27.0 | 24.5 | 60 | 24 |
| Comparative Example 8 | Base water-absorbing resin 8 | Crosslinked polymer powder (e) | TEG/HD/PW = 0.3/0.3/3.4 | 97.9 | 29.0 | 26.0 | 39 | 25 |
| Comparative Example 9 | Base water-absorbing resin 9 | Crosslinked polymer powder (e) | EC/HD/PW = 0.4/0.7/2.9 | 98.1 | 28.2 | 25.8 | 55 | 26 |
| Comparative Example 10 | Base water-absorbing resin 10 | Crosslinked polymer powder (a) | HD/EC/PW = 0.7/0.4/3.9 | 97.3 | 32.6 | 27.6 | 16 | 55 |
| Comparative Example 11 | Base water-absorbing resin 11 | Crosslinked polymer powder (f) | D/PG/PW = 0.03/1.5/3.5 | 96.5 | 40.2 | 22.0 | 4 | 40 |
| Comparative Example 12 | Base water-absorbing resin 12 | Crosslinked polymer powder (g) | BD/PG/PW = 0.3/0.5/3.0 | 97.8 | 35.0 | 21.5 | 21 | 45 |

| | PDAUP (g/g) | Specific surface area (m$^2$/kg) | Mass average particle diameter (μm) | Logarithmic standard deviation (σζ) | Percentage of particles of less than 150 μm (%) |
|---|---|---|---|---|---|
| Comparative Example 1 | 14.0 | 32.5 | 374 | 0.37 | 1.8 |
| Comparative Example 2 | 14.0 | 30.9 | 360 | 0.36 | 1.5 |
| Comparative Example 3 | 10.9 | 31.9 | 385 | 0.39 | 1.7 |
| Comparative Example 4 | 17.0 | 31.1 | — | — | — |
| Comparative Example 5 | 16.8 | 30.7 | — | — | — |
| Comparative Example 6 | 14.7 | 30.5 | — | — | — |
| Comparative Example 7 | 17.9 | 33.9 | — | — | — |
| Comparative Example 8 | 17.1 | 33.1 | — | — | — |
| Comparative Example 9 | 18.1 | 32.4 | — | — | — |
| Comparative Example 10 | 18.4 | 20.6 | — | — | — |
| Comparative Example 11 | 10.8 | 25.9 | — | — | — |
| Comparative Example 12 | 11 | 23.5 | — | — | — |

| | Volatile component concentration during 1.0-fold swelling (ppm) | Volatile component accumulated value during swelling at respective swelling capacities (ppm) | Maximum volatile component concentration during swelling overtime (ppm) | Volatile component accumulated value during swelling over time (ppm) | Evaluation of odor |
|---|---|---|---|---|---|
| Comparative Example 1 | 13.8 | 35.3 | 2.0 | 238.5 | 3 |
| Comparative Example 2 | 5.1 | 13.1 | 0.8 | 88.7 | 3 |
| Comparative Example 3 | 23.4 | 60.0 | 3.5 | 405.7 | 5 |
| Comparative Example 4 | 6.0 | 15.3 | 0.9 | 103.6 | 3 |
| Comparative Example 5 | 13.2 | 33.9 | 2.0 | 229.3 | 5 |
| Comparative Example 6 | 10.0 | 25.6 | 1.5 | 173.0 | 3 |
| Comparative Example 7 | 9.6 | 24.6 | 1.4 | 166.1 | 4 |
| Comparative Example 8 | 4.3 | 11.0 | 0.6 | 74.5 | 3 |
| Comparative Example 9 | 4.6 | 11.8 | 0.7 | 80.0 | 3 |
| Comparative Example 10 | 4.6 | 11.8 | 0.7 | 79.6 | 3 |
| Comparative Example 11 | 3.9 | 9.9 | 0.6 | 67.1 | 3 |
| Comparative Example 12 | 7.9 | 20.2 | 1.2 | 136.8 | 4 |

Example 1

The base water-absorbing resin (1) was heated to 150° C. and introduced, at a rate of 3.0 kg/hr, into a twin-screw indirect heating dryer (CD/80, manufactured by Kurimoto, Ltd.) in which the temperature was set to 150° C. and which serves as a stirring drying device, and deionized water was uniformly added at a rate of 2.0 kg/hr through a material feed opening with use of a spray. A rotation speed of a stirring blade of the twin-screw indirect heating dryer was set to 20 rpm, a barrier at an outlet was regulated so that an amount of powder (water-absorbing resin and deionized water) retained inside the dryer was 2.5 kg, and stirring drying was continuously carried out. A retention time of the powder inside the dryer, i.e., a drying time was 50 minutes. The powder was continuously dried and discharged, so that a water-absorbing resin (1) was obtained. Physical properties of the water-absorbing resin (1) are shown in Table 4.

Example 2

Operations similar to those carried out in Example 1 were carried out except that the base water-absorbing resin (2) was used instead of the base water-absorbing resin (1) to set a retention time of the base water-absorbing resin (2) inside the dryer, i.e., a drying time to 60 minutes by changing the temperature inside the dryer to 60° C., introducing the base water-absorbing resin (2) at a rate of 2.5 kg/hr, and adding tap water at a rate of 0.28 kg/hr. Thus, a water-absorbing resin (2) was obtained. Physical properties of the water-absorbing resin (2) are shown in Table 4.

Example 3

The base water-absorbing resin (3) was heated to 150° C. and introduced, at a rate of 3.00 kg/hr, into a twin-screw indirect heating dryer (CD/80, manufactured by Kurimoto, Ltd.) in which the temperature was set to 85° C. and which serves as a stirring drying device, and a 3.18 mass % aqueous sodium sesquicarbonate solution was uniformly added at a rate of 0.66 kg/hr through a material feed opening with use of a spray. A rotation speed of a stirring blade of the twin-screw indirect heating dryer was set to 20 rpm, a barrier at an outlet was regulated so that an amount of powder (water-absorbing resin and 3.18 mass % aqueous sodium sesquicarbonate solution) retained inside the dryer was 2.5 kg, and stirring drying was continuously carried out. A retention time of the powder inside the dryer, i.e., a drying time was 50 minutes. The powder was continuously dried and discharged, so that a water-absorbing resin (3) was obtained. Physical properties of the water-absorbing resin (3) are shown in Table 4.

Example 4

Operations similar to those carried out in Example 3 were carried out except that the base water-absorbing resin (4) was used instead of the base water-absorbing resin (3) to add a 0.4 mass % aqueous L-cysteine solution at a rate of 0.61 kg/hr instead of adding the aqueous sodium sesquicarbonate solution. Thus, a water-absorbing resin (4) was obtained. Physical properties of the water-absorbing resin (4) are shown in Table 4.

Example 5

Operations similar to those carried out in Example 3 were carried out except that the base water-absorbing resin (5) was used instead of the base water-absorbing resin (3) to add a 0.09 mass % aqueous glycerin fatty acid ester (product name: EXCEL 122V, manufactured by Kao Corporation) solution at a rate of 1.36 kg/hr instead of adding the aqueous sodium sesquicarbonate solution. Thus, a water-absorbing resin (5) was obtained. Physical properties of the water-absorbing resin (5) are shown in Table 4.

Example 6

Operations similar to those carried out in Example 3 were carried out except that the base water-absorbing resin (6) was used instead of the base water-absorbing resin (3) to add a 1.00 mass % aqueous sodium dihydrogenphosphate solution at a rate of 0.61 kg/hr instead of adding the aqueous sodium sesquicarbonate solution. Thus, a water-absorbing resin (6) was obtained. Physical properties of the water-absorbing resin (6) are shown in Table 4.

Example 7

Operations similar to those carried out in Example 3 were carried out except that the base water-absorbing resin (7) was used instead of the base water-absorbing resin (3) to add a 0.67 mass % aqueous dihydrazide adipate solution at a rate of 0.45 kg/hr instead of adding the aqueous sodium sesquicarbonate solution. Thus, a water-absorbing resin (7) was obtained. Physical properties of the water-absorbing resin (7) are shown in Table 4.

Example 8

In a 225 ml mayonnaise bottle, 30 parts by mass of the base water-absorbing resin (8) and 3 parts by mass of dihydrazide adipate were put and mixed by shaking (at room temperature for 3 minutes) with use of a paint shaker (manufactured by Toyo Seiki Seisaku-sho, Ltd.), so that a water-absorbing resin (8) was obtained. Physical properties of the water-absorbing resin (8) are shown in Table 4.

Example 9

A preparative stainless steel column (Cat. No. 6010-15023, manufactured by GL Sciences Inc.) was filled with 50 parts by mass of the base water-absorbing resin (9), and supercritical carbon dioxide was caused to flow at a flow rate of 7.0 g/min at 83.5° C. and 21.0 MPa for 24 hours. Thus, a water-absorbing resin (9) was obtained. Physical properties of the water-absorbing resin (9) are shown in Table 4.

Example 10

Operations similar to those carried out in Example 3 were carried out except that the base water-absorbing resin (10) was used instead of the base water-absorbing resin (3) to add a 0.50 mass % aqueous disodium polyoxyethylene dialkylsulfosuccinate-based anionic surfactant (product name: BEAULIGHT ESS, manufactured by Sanyo Chemical Industries, Ltd.) at a rate of 0.24 kg/hr instead of adding the aqueous sodium sesquicarbonate solution. Thus, a water-absorbing resin (10) was obtained. Physical properties of the water-absorbing resin (10) are shown in Table 4.

Example 11

Operations similar to those carried out in Example 3 were carried out except that the base water-absorbing resin (11) was used instead of the base water-absorbing resin (3) to add a 0.33 mass % aqueous glycerol monooleate (product name: RHEODOL MO-60, manufactured by Kao Corporation) solution at a rate of 0.37 kg/hr instead of adding the aqueous sodium sesquicarbonate solution. Thus, a water-absorbing resin (11) was obtained. Physical properties of the water-absorbing resin (11) are shown in Table 4.

Example 12

Operations similar to those carried out in Example 3 were carried out except that the base water-absorbing resin (12) was used instead of the base water-absorbing resin (3) to add a 1.00 mass % aqueous trisodium phosphate solution at a rate of 1.07 kg/hr instead of adding the aqueous sodium sesquicarbonate solution. Thus, a water-absorbing resin (12) was obtained. Physical properties of the water-absorbing resin (12) are shown in Table 4.

Example 13

Operations similar to those carried out in Example 1 were carried out except that the base water-absorbing resin (3) was used instead of the base water-absorbing resin (1) to set a retention time of the base water-absorbing resin (3) inside the dryer, i.e., a drying time to 60 minutes by introducing the base water-absorbing resin (3) at a rate of 2.5 kg/hr and adding deionized water at a rate of 1.67 kg/hr. Thus, a water-absorbing resin (13) was obtained. Physical properties of the water-absorbing resin (13) are shown in Table 4.

Example 14

Operations similar to those carried out in Example 1 were carried out except that the base water-absorbing resin (4) was used instead of the base water-absorbing resin (1) to change the temperature inside the dryer to 90° C., introduce the base water-absorbing resin (4) at a rate of 3.0 kg/hr, and add deionized water at a rate of 0.75 kg/hr. Thus, a water-absorbing resin (14) was obtained. Physical properties of the water-absorbing resin (14) are shown in Table 4.

Example 15

Operations similar to those carried out in Example 1 were carried out except that the base water-absorbing resin (5) was used instead of the base water-absorbing resin (1) to set a retention time of the base water-absorbing resin (5) inside the dryer, i.e., a drying time to 60 minutes by changing the temperature inside the dryer to 120° C., introducing the base water-absorbing resin (5) at a rate of 2.5 kg/hr, and adding deionized water at a rate of 1.07 kg/hr. Thus, a water-absorbing resin (15) was obtained. Physical properties of the water-absorbing resin (15) are shown in Table 4.

Example 16

Operations similar to those carried out in Example 1 were carried out except that the base water-absorbing resin (6) was used instead of the base water-absorbing resin (1) to set a retention time of the base water-absorbing resin (6) inside the dryer, i.e., a drying time to 60 minutes by changing the temperature inside the dryer to 120° C., introducing the base water-absorbing resin (6) at a rate of 2.5 kg/hr, and adding deionized water at a rate of 1.67 kg/hr. Thus, a water-absorbing resin (16) was obtained. Physical properties of the water-absorbing resin (16) are shown in Table 4.

Example 17

Operations similar to those carried out in Example 1 were carried out except that the base water-absorbing resin (7) was used instead of the base water-absorbing resin (1) to set a retention time of the base water-absorbing resin (7) inside the dryer, i.e., a drying time to 40 minutes by introducing the base water-absorbing resin (7) at a rate of 3.75 kg/hr and adding deionized water at a rate of 1.6 kg/hr. Thus, a water-absorbing resin (17) was obtained. Physical properties of the water-absorbing resin (17) are shown in Table 4.

Example 18

Operations similar to those carried out in Example 1 were carried out except that the base water-absorbing resin (8) was used instead of the base water-absorbing resin (1) to set a retention time of the base water-absorbing resin (8) inside the dryer, i.e., a drying time to 30 minutes by changing the temperature inside the dryer to 90° C., introducing the base water-absorbing resin (8) at a rate of 5.0 kg/hr, and adding deionized water at a rate of 0.55 kg/hr. Thus, a water-absorbing resin (18) was obtained. Physical properties of the water-absorbing resin (18) are shown in Table 4.

Example 19

Operations similar to those carried out in Example 1 were carried out except that the base water-absorbing resin (9) was used instead of the base water-absorbing resin (1) to change the temperature inside the dryer to 100° C., introduce the base water-absorbing resin (9) at a rate of 3.0 kg/hr, and add deionized water at a rate of 0.75 kg/hr. Thus, a water-absorbing resin (19) was obtained. Physical properties of the water-absorbing resin (19) are shown in Table 4.

Example 20

Operations similar to those carried out in Example 3 were carried out except that the base water-absorbing resin (2) was used instead of the base water-absorbing resin (3) to add a 1.5 mass % aqueous aminooxyacetic acid hemihydrochloride solution at a rate of 0.30 kg/hr instead of adding the aqueous sodium sesquicarbonate solution. Thus, a water-absorbing resin (20) was obtained. Physical properties of the water-absorbing resin (20) are shown in Table 4.

Comparative Example 13

With 100 parts by mass of the base water-absorbing resin (4), a water-based liquid containing 0.03 parts by mass of a copolymer of 73 mol % methacrylic acid and 27 mol % methoxypolyethylene glycol methacrylate and 6 parts by mass of deionized water was spray-mixed with use of a spray. Note that an addition number of ethylene glycol of the methoxypolyethylene glycol methacrylate was n=25, and a mass average molecular weight (Mw) of the copolymer was 20000. A resultant mixture was put in a mixer having a heating medium temperature of 98° C., a pressure was reduced to 700 mm $H_2O$, and stirring was carried out for 60 minutes. Thus, a comparative water-absorbing resin (13) was obtained. Various conditions etc. are collectively shown in Table 4, and physical properties of the comparative water-absorbing resin (13) are shown in Table 4.

Comparative Example 14

A comparative water-absorbing resin (14) was obtained in conformity with Example 4 of WO2012/108253. The following description shows a specific preparation method.
(Preparation of First Aqueous Solution)
Into a 500 ml Erlenmeyer flask, 92 g of a 80.5 mass % aqueous acrylic acid solution was measured out. While the Erlenmeyer flask was cooled from the outside, 156.2 g of a 23.7 mass % aqueous sodium hydroxide solution was added dropwise to the aqueous acrylic acid solution for neutralization of 90 mol % of 100 mol % of the acrylic acid. Thereafter, the mixture was stirred at room temperature to dissolve completely. In the mixture, 0.11 g of potassium persulfate and 9.2 mg of ethylene glycol diglycidyl ether were added and dissolved so that a first monomer aqueous solution was prepared.
(Preparation of Second Aqueous Solution)
Into a 500 ml Erlenmeyer flask, 128.8 g of a 80.5 mass % aqueous acrylic acid solution was measured out. While the Erlenmeyer flask was cooled from the outside, 150.2 g of a 23.0 mass % aqueous sodium hydroxide solution was added dropwise to the aqueous acrylic acid solution for neutralization of 60 mol % of 100 mol % of the acrylic acid. In the mixture, 0.15 g of potassium persulfate and 12.9 mg of N,N'-methylenebisacrylamide were added and dissolved so that a second monomer aqueous solution was prepared. This second aqueous solution maintained its temperature at approximately 23° C.
(Step 1)
A cylindrical round bottom separable flask having an inner diameter of 100 mm and provided with a reflux condenser, a dropping funnel, a nitrogen gas inlet tube, and a stirrer (a stirring blade having, in two stages, four inclined paddle blades each having a diameter of 50 mm) was prepared. In this flask, 500 ml of n-heptane was placed, and 0.92 g of a maleic anhydride modified ethylene-propylene copolymer (trade name "High Wax 1105A" of Mitsui Chemicals, Inc.) was added thereto. Then, a resultant mixture was heated to 80° C. to dissolve and then cooled to 60° C.

A rotation speed of the stirrer was set to 300 rpm, and a funnel was used to add the first aqueous solution to the separable flask at a time. Then, the temperature in the flask was set to 40° C. so that a resultant mixture was dispersed while being stirred for 10 minutes. Next, a solution prepared by dissolving, under heating, 0.92 g of sucrose stearic acid ester (surfactant, trade name "Ryoto sugar ester S-370" of MITSUBISHI-CHEMICAL FOODS CORPORATION) of HLB 3 in 8.5 g of n-heptane was added to the separable flask with use of the funnel, and a stirring speed was changed to 500 rpm so that the first aqueous solution was further dispersed.

Subsequently, the rotation speed of the stirrer was set to 450 rpm, and the temperature inside the separable flask was maintained at 40° C. for 30 minutes while air in the separable flask was being replaced with nitrogen. Thereafter, the flask was immersed in a water bath at 70° C. so as to be heated, and was subjected to polymerization. Then, a slurry of spherical primary particles was obtained. An oil bath at 120° C. was used to subject water and n-heptane to azeotropy so as to remove water only from part of the slurry to the outside of the system. Next, the spherical primary particles obtained by drying the slurry by evaporation of n-heptane had a median particle diameter of 80 μm.

(Step 2)

The number of stirring revolutions of the slurry obtained in the step 1 was changed to 1000 rpm so that the slurry was cooled to 23° C. Then, the second aqueous solution was added to the slurry. Then, the temperature inside the flask was maintained for 30 minutes while air in the flask was being replaced with nitrogen. Thereafter, the flask was immersed again in the water bath at 70° C. so as to be heated, and was subjected to polymerization. Thus, a slurry containing secondary particles, which are an agglomeration of primary particles, was obtained.

(Postcrosslinking Step)

After the step 2, the oil bath at 120° C. was used to heat the flask and subject water and n-heptane to azeotropy, so that 251.7 g of water was removed to the outside of the system while n-heptane was being refluxed. Then, 8.83 g of a 2% aqueous ethylene glycol diglycidyl ether solution (post-crosslinking agent) was added to contents of the flask. A resultant mixture was maintained at 80° C. for 2 hours, and then n-heptane was evaporated so that the mixture was dried. Thus, 230.9 g of a comparative water-absorbing resin (4) containing surface-crosslinked secondary particles was obtained.

TABLE 4

| | Surface-crosslinked water-absorbing resin | Surface-treating agent | Solid content (mass %) | CRC (g/g) | AAP (g/g) | SFC (sec/g) | Vortex (sec) | PDAUP (g/g) | Specific surface area (m²/kg) | Mass average particle diameter (μm) |
|---|---|---|---|---|---|---|---|---|---|---|
| Example 1 | Base water-absorbing resin 1 | EC/PG/PW = 0.3/0.7/3.0 | 95.5 | 30.0 | 23.1 | 29 | 27 | 13.3 | 31.7 | 388 |
| Example 2 | Base water-absorbing resin 2 | TEG/PW = 1.0/3.0 | 96.2 | 30.8 | 23.7 | 25 | 28 | 13.4 | 31.1 | 355 |
| Example 3 | Base water-absorbing resin 3 | EC/PC/PW = 1.0/1.0/4.0 | 95.1 | 32.2 | 22.5 | 10 | 32 | 11.5 | 28.9 | 398 |
| Example 4 | Base water-absorbing resin 4 | EG/PW = 0.8/2.5 | 95.5 | 29.1 | 25.6 | 32 | 29 | 16.2 | 30.7 | — |
| Example 5 | Base water-absorbing resin 5 | HD/PG/PW = 0.8/0.8/2.4 | 90.5 | 27.0 | 24.0 | 31 | 33 | 14.4 | 28.7 | — |
| Example 6 | Base water-absorbing resin 6 | TEG/PG/PW = 0.5/0.5/3.0 | 95.5 | 29.7 | 24.3 | 22 | 30 | 13.7 | 30.0 | — |
| Example 7 | Base water-absorbing resin 7 | BD/PG/PW = 0.4/0.6/2.8 | 96.5 | 27.1 | 23.6 | 55 | 27 | 17.0 | 31.7 | — |
| Example 8 | Base water-absorbing resin 8 | TEG/HD/PW = 0.3/0.3/3.4 | 98.1 | 29.1 | 24.1 | 34 | 30 | 14.8 | 29.9 | — |
| Example 9 | Base water-absorbing resin 9 | EC/HD/PW = 0.4/0.7/2.9 | 98.6 | 28.3 | 25.9 | 55 | 26 | 18.2 | 32.4 | — |
| Example 10 | Base water-absorbing resin 10 | HD/EC/PW = 0.7/0.4/2.9 | 97.9 | 32.8 | 27.8 | 16 | 52 | 18.7 | 21.2 | — |
| Example 11 | Base water-absorbing resin 11 | D/PG/PW = 0.03/1.5/3.5 | 97.1 | 40.4 | 22.1 | 4 | 40 | 11.0 | 26.0 | — |

| | Logarithmic standard deviation (σζ) | Percentage of particles of less than 150 μm (%) | Volatile component concentration during 1.0-fold swelling (ppm) | Volatile component accumulated value during swelling at respective swelling capacities (ppm) | Maximum volatile component concentration during swelling overtime (ppm) | Volatile component accumulated value during swelling overtime (ppm) | Evaluation of odor |
|---|---|---|---|---|---|---|---|
| Example 1 | 0.38 | 1.4 | 0.0 | 0.0 | 0.0 | 0.0 | 0 |
| Example 2 | 0.36 | 1.2 | 1.7 | 4.3 | 0.2 | 28.9 | 1 |
| Example 3 | 0.37 | 1.5 | 2.5 | 6.4 | 0.4 | 43.0 | 1 |
| Example 4 | — | — | 0.8 | 2.0 | 0.1 | 13.5 | 0 |
| Example 5 | — | — | 0.1 | 0.2 | 0.0 | 0.0 | 0 |
| Example 6 | — | — | 1.3 | 3.3 | 0.2 | 22.5 | 0 |
| Example 7 | — | — | 1.1 | 2.8 | 0.2 | 18.7 | 0 |
| Example 8 | — | — | 2.3 | 5.9 | 0.3 | 39.8 | 1 |
| Example 9 | — | — | 2.4 | 6.1 | 0.4 | 41.6 | 1 |
| Example 10 | — | — | 2.0 | 5.2 | 0.3 | 35.2 | 1 |
| Example 11 | — | — | 1.1 | 2.9 | 0.2 | 19.7 | 0 |

TABLE 4-continued

| | Surface-crosslinked water-absorbing resin | Surface-treating agent | Solid content (mass %) | CRC (g/g) | AAP (g/g) | SFC (sec/g) | Vortex (sec) | PDAUP (g/g) | Specific surface area (m²/kg) |
|---|---|---|---|---|---|---|---|---|---|
| Example 12 | Base water-absorbing resin 12 | BD/PG/PW = 0.3/0.5/3.0 | 92.5 | 31.2 | 23.6 | 20 | 48 | 13 | 23.8 |
| Example 13 | Base water-absorbing resin 3 | EC/PC/PW = 1.0/1.0/4.0 | 96.6 | 32.4 | 22.8 | 10 | 30 | 10.4 | 30.1 |
| Example 14 | Base water-absorbing resin 4 | EG/PW = 0.8/2.5 | 94.8 | 29.1 | 25.8 | 31 | 29 | 16.4 | 30.5 |
| Example 15 | Base water-absorbing resin 5 | HD/PG/PW = 0.8/0.8/2.4 | 94.4 | 28.3 | 25.6 | 32 | 30 | 16.2 | 30.2 |
| Example 16 | Base water-absorbing resin 6 | TEG/PG/PW = 0.5/0.5/3.0 | 93.3 | 29.3 | 24.4 | 20 | 28 | 13.5 | 31.1 |
| Example 17 | Base water-absorbing resin 7 | BD/PG/PW = 0.4/0.6/2.8 | 95.3 | 26.1 | 24.0 | 57 | 24 | 17.4 | 33.9 |
| Example 18 | Base water-absorbing resin 8 | TEG/HD/PW = 0.3/0.3/3.4 | 97.0 | 28.7 | 25.9 | 39 | 26 | 17.0 | 32.4 |
| Example 19 | Base water-absorbing resin 9 | EC/HD/PW = 0.4/0.7/2.9 | 96.3 | 27.8 | 25.6 | 52 | 26 | 17.7 | 32.4 |
| Example 20 | Base water-absorbing resin 2 | TEG/PW = 1.0/3.0 | 97.5 | 31.2 | 24.0 | 26 | 28 | 13.6 | 31.5 |
| Comparative Example 13 | Base water-absorbing resin 4 | EG/PW = 0.8/2.5 | 98.2 | 30.5 | 25.0 | 23 | 29 | 16.4 | 30.9 |
| Comparative Example 14 | — | — | 92.4 | — | — | — | — | — | — |

| | Mass average particle diameter (μm) | Logarithmic standard deviation (σζ) | Percentage of particles of less than 150 μm (%) | Volatile component concentration during 1.0-fold swelling (ppm) |
|---|---|---|---|---|
| Example 12 | — | — | — | 0.2 |
| Example 13 | — | — | — | 0.1 |
| Example 14 | — | — | — | 0.5 |
| Example 15 | — | — | — | 0.2 |
| Example 16 | — | — | — | 0.0 |
| Example 17 | — | — | — | 0.1 |
| Example 18 | — | — | — | 1.4 |
| Example 19 | — | — | — | 0.4 |
| Example 20 | — | — | — | 1.3 |
| Comparative Example 13 | — | — | — | 6.4 |
| Comparative Example 14 | — | — | — | 31.6 |

| | Volatile component accumulated value during swelling at respective swelling capacities (ppm) | Maximum volatile component concentration during swelling over time (ppm) | Volatile component accumulated value during swelling over time (ppm) | Evaluation of odor |
|---|---|---|---|---|
| Example 12 | 0.4 | 0.0 | 0.0 | 0 |
| Example 13 | 0.3 | 0.1 | 1.7 | 1 |
| Example 14 | 1.2 | 0.1 | 8.1 | 2 |
| Example 15 | 0.4 | 0.1 | 2.9 | 2 |
| Example 16 | 0.0 | 0.0 | 0.0 | 1 |
| Example 17 | 0.3 | 0.1 | 2.1 | 1 |
| Example 18 | 3.6 | 0.2 | 24.2 | 0 |
| Example 19 | 0.9 | 0.1 | 6.2 | 1 |
| Example 20 | 3.3 | 0.2 | 22.5 | 1 |
| Comparative Example 13 | 16.4 | 0.9 | 110.8 | 4 |
| Comparative Example 14 | 80.9 | 4.7 | 547.2 | 5 |

SUMMARY

As is clear from Table 4, the water-absorbing resins 1 to 20 obtained in respective Examples 1 to 20 each has a volatile component concentration during 1.0-fold swelling of 3.5 ppm or less and an odor evaluation score of 0 to 2, so that no or little unpleasant odor is perceived.

As is clear from Tables 3 and 4, the base water-absorbing resins 1 to 12 obtained in respective Comparative Examples 1 to 12, and the comparative water-absorbing resins (13) and (14) each has a volatile component concentration during 1.0-fold swelling of 3.9 ppm or more and an odor evaluation score of 3 or more, so that an unpleasant odor is clearly perceived.

As is clear from a comparison between Examples 1 to 20 and Comparative Examples 1 to 14, it has been found that in a case where a water-absorbing resin has a volatile component concentration during 1.0-fold swelling of 3.5 ppm or less, it is possible to obtain a water-absorbing resin that has a sufficiently reduced odor produced during swelling. It has also been found that the water-absorbing resins 1 to 20 maintain physical properties and meet a request for, for example, water absorption performance that recent hygienic materials are required to exhibit.

INDUSTRIAL APPLICABILITY

A water-absorbing resin according to an embodiment of the present invention can be used to produce a water-absorbing resin that while maintaining water-absorbing resin physical properties such as water absorption performance, has a sufficiently reduced odor produced during swelling, and a hygienic material containing the water-absorbing resin.

REFERENCE SIGNS LIST

1 Carbon dioxide cylinder
2 Pressure regulating valve
3 High pressure liquid feed pump
4 Cooling device
5 Pressure-resistant extraction tank
6 Pressure reducing valve
7 Flowmeter
8 Glass bottle
9 Polyethylene lid
10 Polyethylene cap

The invention claimed is:

1. A water-absorbing resin which is a surface-crosslinked water-absorbing resin, said water-absorbing resin comprising a volatile component concentration of 3.5 ppm or less as measured when said water-absorbing resin is caused to stand still for 15 minutes under a condition that said water-absorbing resin has a swelling capacity of 1.0-fold, where the volatile component concentration as measured when said water-absorbing resin is caused to stand still for 15 minutes under the condition that said water-absorbing resin has a swelling capacity of 1.0-fold is a numerical value obtained by adding together concentrations of all substances that are detected by a photoion detector (PID) of a 10.6 eV lamp and that are included in a volatile component which is present in a closed vessel when 10.0 g of a physiological saline at 23.5±0.5° C. is uniformly added, under room temperature and atmospheric pressure, to 10.0 g of said water-absorbing resin contained in a 2-liter closable glass vessel and said water-absorbing resin to which the physiological saline has been added is caused to stand still in a closed state for 15 minutes, the volatile component concentration being a value represented by a detection value in terms of isobutylene, which is a calibration gas.

2. The water-absorbing resin according to claim 1, wherein a sum of volatile component concentrations as measured when said water-absorbing resin is caused to stand still for 15 minutes under conditions that said water-absorbing resin has respective swelling capacities of 0.0-fold, 0.5-fold, 1.0-fold, 2.5-fold, 5.0-fold, 10.0-fold, and 20.0-fold is 9.5 ppm or less.

3. The water-absorbing resin according to claim 1, wherein a maximum value of volatile component concentrations measured every five seconds, under a condition that said water-absorbing resin has a swelling capacity of 5.0-fold, until 900 seconds have passed since initiation of swelling of said water-absorbing resin is 0.4 ppm or less.

4. The water-absorbing resin according to claim 1, wherein a sum of volatile component concentrations measured every five seconds, under a condition that said water-absorbing resin has a swelling capacity of 5.0-fold, until 900 seconds have passed since initiation of swelling of said water-absorbing resin is 50.0 ppm or less.

5. The water-absorbing resin according to claim 1, wherein said water-absorbing resin has an absorption capacity without load (CRC) of 23 g/g or more and an absorption capacity under load (AAP) of 15 g/g or more.

6. The water-absorbing resin according to claim 1, wherein said water-absorbing resin has a mass average particle diameter (D50) of 300 μm to 600 μm, a proportion of particles having a particle diameter of less than 150 μm in said water-absorbing resin is 5 mass % or less, and said water-absorbing resin has a logarithmic standard deviation (σζ) of a particle size distribution of 0.20 to 0.50.

7. The water-absorbing resin according to claim 1, wherein said water-absorbing resin contains a volatile component reducing agent.

8. The water-absorbing resin according to claim 1, wherein said water-absorbing resin has a specific surface area of 25 $m^2$/kg or more.

9. An absorbent article comprising a water-absorbing resin recited in claim 1.

10. The absorbent article according to claim 9, wherein said absorbent article includes an absorbent body, which is a composite containing said water-absorbing resin and a hydrophilic fiber, and said water-absorbing resin is contained in an amount of 60 mass % or more relative to a total mass of the absorbent body.

11. A method for producing a water-absorbing resin recited in claim 1, successively comprising: a polymerization step of polymerizing an acrylic acid (salt)-based monomer-containing monomer composition so as to obtain a crosslinked hydrogel polymer; a drying step of drying the crosslinked hydrogel polymer that has been obtained in the polymerization step; and a surface-crosslinking step, said method further comprising, at or after an end of the polymerization step, the step of adding an amino group-containing reducing agent.

12. The method according to claim 11, wherein said method includes, at or after an end of the surface-crosslinking step, the step of adding the amino group-containing reducing agent.

13. The method according to claim 11, wherein said method includes the step of adding the amino group-containing reducing agent as an aqueous solution.

14. The method according to claim 11, wherein the amino group-containing reducing agent contains a hydrazide group-containing compound.

15. A method for producing a water-absorbing resin, comprising the step of adding a water-based liquid in a droplet state to a surface-crosslinked water-absorbing resin so that the surface-crosslinked water-absorbing resin to which the water-based liquid has been added has a moisture content of 7.5 mass % or more, and then drying the surface-crosslinked water-absorbing resin, to which the water-based liquid has been added, so that the moisture content is reduced by an amount of 7.5 mass % or more within one hour.

16. A method recited in claim 15, further comprising at least one of the following steps (A) and (B):
(A) adding a water-based liquid in a droplet state to the surface-crosslinked water-absorbing resin that has a specific surface area of 25 $m^2$/kg or more; and
(B) successively including a polymerization step, a drying step of drying a hydrogel having been obtained in the polymerization step, and a surface-crosslinking step, and adding a volatile component reducing agent at or after an end of the polymerization step.

17. The method according to claim 16, wherein said method includes the step (A) of adding a water-based liquid in a droplet state to the surface-crosslinked water-absorbing resin that has a specific surface area of 25 $m^2$/kg or more, and in a case where the water-based liquid is added so that the surface-crosslinked water-absorbing resin to which the water-based liquid has been added has a moisture content of 27.5 mass % or more, the surface-crosslinked water-absorbing resin, to which the water-based liquid has been added, is dried so that the surface-crosslinked water-absorbing resin has a moisture content of 20 mass % or less within one hour.

18. The method according to claim 16, wherein said method includes the step (B) of successively including a polymerization step, a drying step of drying a hydrogel having been obtained in the polymerization step, and a surface-crosslinking step, and adding a volatile component reducing agent at or after an end of the polymerization step.

19. A method for producing a water-absorbing resin, comprising the step of bringing the water-absorbing resin into contact with a supercritical solvent so as to remove a volatile component from the water-absorbing resin, the water-absorbing resin containing a polyacrylic acid (salt)-based resin as a main component, the water-absorbing resin being internally crosslinked, and the water-absorbing resin being surface-crosslinked.

\* \* \* \* \*